US012076037B2

(12) United States Patent
Brady et al.

(10) Patent No.: US 12,076,037 B2
(45) Date of Patent: Sep. 3, 2024

(54) SYSTEMS AND METHODS TO RESTORE PERFUSION TO A VESSEL

(71) Applicant: Neuravi Limited, Galway (IE)

(72) Inventors: Eamon Brady, Loughrea (IE); Brendan Casey, Barna (IE); Michael Gilvarry, Headford (IE); David Hardiman, Dublin (IE); Kevin McArdle, Loughrea (IE); Mahmood K. Razavi, Irvine, CA (US); David Vale, Barna (IE); Patrick Griffin, Castlegar (IE); Jason McNamara, Knock (IE); Mairsil Claffey, Galway (IE)

(73) Assignee: Neuravi Limited, Galway (IE)

( * ) Notice: Subject to any disclaimer, the term of this patent is extended or adjusted under 35 U.S.C. 154(b) by 0 days.

(21) Appl. No.: 18/232,449

(22) Filed: Aug. 10, 2023

(65) Prior Publication Data

US 2023/0380851 A1 Nov. 30, 2023

Related U.S. Application Data

(63) Continuation of application No. 17/749,433, filed on May 20, 2022, now abandoned, and a
(Continued)

(51) Int. Cl.
*A61B 17/221* (2006.01)
*A61F 2/01* (2006.01)
(Continued)

(52) U.S. Cl.
CPC ............ *A61B 17/221* (2013.01); *A61F 2/013* (2013.01); *A61M 29/00* (2013.01);
(Continued)

(58) Field of Classification Search
CPC ............ A61B 17/221; A61B 17/22031; A61B 17/12118; A61B 17/1214; A61B 2017/2212; A61B 2017/2215; A61B 2017/2217; A61B 2017/22034; A61F 2/013
See application file for complete search history.

(56) References Cited

U.S. PATENT DOCUMENTS

| 4,455,717 A | 6/1984 | Gray |
| 4,611,594 A | 9/1986 | Grayhack et al. |

(Continued)

FOREIGN PATENT DOCUMENTS

| CN | 2557083 Y | 6/2003 |
| CN | 101172051 A | 5/2008 |

(Continued)

OTHER PUBLICATIONS

US 6,348,062 B1, 02/2002, Hopkins et al. (withdrawn)
(Continued)

*Primary Examiner* — Dianne Dornbusch
(74) *Attorney, Agent, or Firm* — Troutman Pepper Hamilton Sanders LLP

(57) ABSTRACT

Methods and systems for using a clot retrieval device for treating a clot in a blood vessel for use in the treatment of ischemic stroke to achieve a clinically effective revascularization or perfusion rate for clots comprising a higher ratio of red blood cells to fibrin.

8 Claims, 36 Drawing Sheets

Related U.S. Application Data continuation-in-part of application No. 17/207,011, filed on Mar. 19, 2021, said application No. 17/749,433 is a continuation-in-part of application No. 16/569,637, filed on Sep. 12, 2019, now abandoned, said application No. 17/207,011 is a continuation of application No. 15/997,335, filed on Jun. 4, 2018, now Pat. No. 10,952,760, said application No. 16/569,637 is a continuation-in-part of application No. 14/985,729, filed on Dec. 31, 2015, now Pat. No. 10,610,246, said application No. 15/997,335 is a continuation of application No. 14/986,357, filed on Dec. 31, 2015, now Pat. No. 10,034,680, said application No. 14/985,729 is a continuation of application No. 14/629,217, filed on Feb. 23, 2015, now Pat. No. 9,445,829, which is a continuation of application No. PCT/EP2014/054251, filed on Mar. 5, 2014, said application No. 14/986,357 is a continuation of application No. 13/823,060, filed as application No. PCT/IE2012/000011 on Mar. 9, 2012, now Pat. No. 9,301,769.

(60) Provisional application No. 63/190,892, filed on May 20, 2021, provisional application No. 62/844,502, filed on May 7, 2019, provisional application No. 62/822,467, filed on Mar. 22, 2019, provisional application No. 62/792,741, filed on Jan. 15, 2019, provisional application No. 62/772,006, filed on Nov. 27, 2018, provisional application No. 62/730,952, filed on Sep. 13, 2018, provisional application No. 61/785,213, filed on Mar. 14, 2013, provisional application No. 61/552,130, filed on Oct. 27, 2011, provisional application No. 61/450,810, filed on Mar. 9, 2011.

(51) Int. Cl.
*A61M 29/00* (2006.01)
*A61B 17/00* (2006.01)
*A61B 17/22* (2006.01)
*A61M 29/02* (2006.01)

(52) U.S. Cl.
CPC ............... *A61B 2017/00778* (2013.01); *A61B 2017/22034* (2013.01); *A61B 2017/2212* (2013.01); *A61B 2017/2215* (2013.01); *A61M 29/02* (2013.01)

(56) References Cited

U.S. PATENT DOCUMENTS

| | | |
|---|---|---|
| 4,612,931 A | 9/1986 | Dormia |
| 4,643,184 A | 2/1987 | Mobin-Uddin |
| 4,727,873 A | 3/1988 | Mobin-Uddin |
| 4,793,348 A | 12/1988 | Palmaz |
| 4,873,978 A | 10/1989 | Ginsburg |
| 5,011,488 A | 4/1991 | Ginsburg |
| 5,084,065 A | 1/1992 | MacGregor et al. |
| 5,092,839 A | 3/1992 | Kipperman |
| 5,100,423 A | 3/1992 | Fearnot |
| 5,102,415 A | 4/1992 | Guenther et al. |
| 5,108,419 A | 4/1992 | Reger et al. |
| 5,122,136 A | 6/1992 | Guglielmi et al. |
| 5,163,951 A | 11/1992 | Pinchuk et al. |
| 5,171,233 A | 12/1992 | Amplatz et al. |
| 5,171,259 A | 12/1992 | Inoue |
| 5,217,441 A | 6/1993 | Shichman |
| 5,234,437 A | 8/1993 | Sepetka |
| 5,236,447 A | 8/1993 | Kubo et al. |
| 5,330,482 A | 7/1994 | Gibbs et al. |
| 5,383,887 A | 1/1995 | Nadal |
| 5,387,219 A | 2/1995 | Rappe |
| 5,387,226 A | 2/1995 | Miraki |
| 5,449,372 A | 9/1995 | Schmaltz et al. |
| 5,499,985 A | 3/1996 | Hein et al. |
| 5,538,512 A | 7/1996 | Zenzon et al. |
| 5,538,515 A | 7/1996 | Kafry et al. |
| 5,549,626 A | 8/1996 | Miller et al. |
| 5,558,652 A | 9/1996 | Henke |
| 5,609,627 A | 3/1997 | Goicoechea et al. |
| 5,624,461 A | 4/1997 | Mariant |
| 5,639,277 A | 6/1997 | Mariant et al. |
| 5,639,278 A | 6/1997 | Dereume et al. |
| 5,645,558 A | 7/1997 | Horton |
| 5,653,605 A | 8/1997 | Woehl et al. |
| 5,658,296 A | 8/1997 | Bates et al. |
| 5,665,117 A | 9/1997 | Rhodes |
| 5,695,519 A | 12/1997 | Summers et al. |
| 5,709,704 A | 1/1998 | Nott et al. |
| 5,713,853 A | 2/1998 | Clark et al. |
| 5,733,325 A | 3/1998 | Robinson et al. |
| 5,769,871 A | 6/1998 | Mers Kelly et al. |
| 5,769,884 A | 6/1998 | Solovay |
| 5,779,686 A | 7/1998 | Sato et al. |
| 5,779,716 A | 7/1998 | Cano et al. |
| 5,800,519 A | 9/1998 | Sandock |
| 5,810,874 A | 9/1998 | Lefebvre |
| 5,814,064 A | 9/1998 | Daniel et al. |
| 5,824,041 A | 10/1998 | Lenker et al. |
| 5,827,304 A | 10/1998 | Hart |
| 5,853,422 A | 12/1998 | Huebsch et al. |
| 5,855,598 A | 1/1999 | Pinchuk |
| 5,893,869 A | 4/1999 | Barnhart et al. |
| 5,895,398 A | 4/1999 | Wensel et al. |
| 5,897,567 A | 4/1999 | Ressemann et al. |
| 5,904,698 A | 5/1999 | Thomas et al. |
| 5,911,702 A | 6/1999 | Romley et al. |
| 5,911,725 A | 6/1999 | Boury |
| 5,919,126 A | 7/1999 | Armini |
| 5,931,509 A | 8/1999 | Bartholomew |
| 5,935,139 A | 8/1999 | Bates |
| 5,947,995 A | 9/1999 | Samuels |
| 6,063,113 A | 5/2000 | Kavteladze et al. |
| 6,066,149 A | 5/2000 | Samson et al. |
| 6,066,158 A | 5/2000 | Engelson et al. |
| 6,093,196 A | 7/2000 | Okada |
| 6,093,199 A | 7/2000 | Brown et al. |
| 6,096,053 A | 8/2000 | Bates |
| 6,099,534 A | 8/2000 | Bates et al. |
| 6,099,559 A | 8/2000 | Nolting |
| 6,102,932 A | 8/2000 | Kurz |
| 6,106,548 A | 8/2000 | Roubin et al. |
| 6,129,739 A | 10/2000 | Khosravi |
| 6,143,022 A | 11/2000 | Shull et al. |
| 6,146,404 A | 11/2000 | Kim et al. |
| 6,156,064 A | 12/2000 | Chouinard |
| 6,165,194 A | 12/2000 | Denardo |
| 6,165,199 A | 12/2000 | Barbut |
| 6,168,604 B1 | 1/2001 | Cano |
| 6,168,622 B1 | 1/2001 | Mazzocchi |
| 6,174,318 B1 | 1/2001 | Bates et al. |
| 6,179,861 B1 | 1/2001 | Khosravi et al. |
| 6,203,561 B1 | 3/2001 | Ramee et al. |
| 6,214,026 B1 | 4/2001 | Lepak et al. |
| 6,221,006 B1 | 4/2001 | Dubrul et al. |
| 6,221,096 B1 | 4/2001 | Aiba et al. |
| 6,231,597 B1 | 5/2001 | Deem et al. |
| 6,238,412 B1 | 5/2001 | Dubrul et al. |
| 6,245,012 B1 | 6/2001 | Kleshinski |
| 6,245,087 B1 | 6/2001 | Addis |
| 6,251,122 B1 | 6/2001 | Tsukernik |
| 6,254,571 B1 | 7/2001 | Hart |
| 6,264,663 B1 | 7/2001 | Cano |
| 6,267,777 B1 | 7/2001 | Bosma et al. |
| 6,290,710 B1 | 9/2001 | Cryer et al. |
| 6,312,444 B1 | 11/2001 | Barbut |
| 6,315,778 B1 | 11/2001 | Gambale et al. |
| 6,325,815 B1 | 12/2001 | Kusleika et al. |
| 6,325,819 B1 | 12/2001 | Pavcnik et al. |

(56) References Cited

U.S. PATENT DOCUMENTS

| | | |
|---|---|---|
| 6,334,864 B1 | 1/2002 | Amplatz et al. |
| 6,336,934 B1 | 1/2002 | Gilson et al. |
| 6,346,116 B1 | 2/2002 | Brooks et al. |
| 6,348,056 B1 | 2/2002 | Bates et al. |
| 6,350,271 B1 | 2/2002 | Kurz et al. |
| 6,355,057 B1 | 3/2002 | DeMarais et al. |
| 6,361,545 B1 | 3/2002 | Macoviak et al. |
| 6,364,895 B1 | 4/2002 | Greenhalgh |
| 6,375,668 B1 | 4/2002 | Gifford et al. |
| 6,375,670 B1 | 4/2002 | Greenhalgh |
| 6,383,205 B1 | 5/2002 | Samson et al. |
| 6,383,206 B1 | 5/2002 | Gillick et al. |
| 6,391,037 B1 | 5/2002 | Greenhalgh |
| 6,402,771 B1 | 6/2002 | Palmer et al. |
| 6,416,541 B2 | 7/2002 | Denardo |
| 6,425,909 B1 | 7/2002 | Dieck et al. |
| 6,428,558 B1 | 8/2002 | Jones et al. |
| 6,432,122 B1 | 8/2002 | Gilson et al. |
| 6,436,112 B2 | 8/2002 | Wensel et al. |
| 6,458,139 B1 | 10/2002 | Palmer et al. |
| 6,485,497 B2 | 11/2002 | Wensel et al. |
| 6,485,501 B1 | 11/2002 | Green |
| 6,485,502 B2 | 11/2002 | Don Michael et al. |
| 6,488,701 B1 | 12/2002 | Nolting et al. |
| 6,511,492 B1 | 1/2003 | Rosenbluth et al. |
| 6,530,935 B2 | 3/2003 | Wensel et al. |
| 6,530,939 B1 | 3/2003 | Hopkins et al. |
| 6,540,768 B1 | 4/2003 | Diaz et al. |
| 6,544,279 B1 | 4/2003 | Hopkins et al. |
| 6,551,341 B2 | 4/2003 | Boylan et al. |
| 6,551,342 B1 | 4/2003 | Shen et al. |
| 6,575,996 B1 | 6/2003 | Denison et al. |
| 6,575,997 B1 | 6/2003 | Palmer et al. |
| 6,582,448 B1 | 6/2003 | Boyle et al. |
| 6,585,756 B1 | 7/2003 | Strecker |
| 6,589,265 B1 | 7/2003 | Palmer et al. |
| 6,592,607 B1 | 7/2003 | Palmer et al. |
| 6,592,614 B2 | 7/2003 | Lenker et al. |
| 6,592,616 B1 | 7/2003 | Stack et al. |
| 6,602,265 B2 | 8/2003 | Dubrul et al. |
| 6,602,271 B2 | 8/2003 | Adams et al. |
| 6,602,272 B2 | 8/2003 | Boylan et al. |
| 6,605,102 B1 | 8/2003 | Mazzocchi et al. |
| 6,610,077 B1 | 8/2003 | Hancock et al. |
| 6,616,679 B1 | 9/2003 | Khosravi et al. |
| 6,632,241 B1 | 10/2003 | Hancock et al. |
| 6,638,245 B2 | 10/2003 | Miller et al. |
| 6,638,293 B1 | 10/2003 | Makower et al. |
| 6,641,590 B1 | 11/2003 | Palmer et al. |
| 6,656,218 B1 | 12/2003 | Denardo et al. |
| 6,660,021 B1 | 12/2003 | Palmer et al. |
| 6,663,650 B2 | 12/2003 | Sepetka et al. |
| 6,673,089 B1 | 1/2004 | Yassour et al. |
| 6,685,722 B1 | 2/2004 | Rosenbluth et al. |
| 6,692,504 B2 | 2/2004 | Kurz et al. |
| 6,692,508 B2 | 2/2004 | Wensel et al. |
| 6,692,509 B2 | 2/2004 | Wensel et al. |
| 6,695,858 B1 | 2/2004 | Dubrul et al. |
| 6,702,782 B2 | 3/2004 | Miller et al. |
| 6,702,834 B1 | 3/2004 | Boylan et al. |
| 6,709,465 B2 | 3/2004 | Mitchell et al. |
| 6,712,834 B2 | 3/2004 | Yassour et al. |
| 6,726,701 B2 | 4/2004 | Gilson et al. |
| 6,726,703 B2 | 4/2004 | Broome et al. |
| 6,730,104 B1 | 5/2004 | Sepetka et al. |
| 6,783,528 B2 | 8/2004 | Vincent-Prestigiacomo |
| 6,783,538 B2 | 8/2004 | McGuckin, Jr. et al. |
| 6,824,545 B2 | 11/2004 | Sepetka et al. |
| 6,855,155 B2 | 2/2005 | Denardo et al. |
| 6,878,163 B2 | 4/2005 | Denardo et al. |
| 6,890,340 B2 | 5/2005 | Duane |
| 6,913,612 B2 | 7/2005 | Palmer et al. |
| 6,913,618 B2 | 7/2005 | Denardo et al. |
| 6,939,361 B1 | 9/2005 | Kleshinski |
| 6,953,472 B2 | 10/2005 | Palmer et al. |
| 6,989,019 B2 | 1/2006 | Mazzocchi et al. |
| 6,989,021 B2 | 1/2006 | Bosma et al. |
| 6,994,718 B2 | 2/2006 | Groothuis et al. |
| 7,004,954 B1 | 2/2006 | Voss et al. |
| 7,004,955 B2 | 2/2006 | Shen et al. |
| 7,004,956 B2 | 2/2006 | Palmer et al. |
| 7,008,434 B2 | 3/2006 | Kurz et al. |
| 7,033,376 B2 | 4/2006 | Tsukernik |
| 7,041,116 B2 | 5/2006 | Goto et al. |
| 7,048,758 B2 | 5/2006 | Boyle et al. |
| 7,052,500 B2 | 5/2006 | Bashiri et al. |
| 7,058,456 B2 | 6/2006 | Pierce |
| 7,063,707 B2 | 6/2006 | Bose et al. |
| 7,083,633 B2 | 8/2006 | Morrill et al. |
| 7,083,822 B2 | 8/2006 | Brightbill |
| 7,094,249 B1 | 8/2006 | Broome et al. |
| 7,097,653 B2 | 8/2006 | Freudenthal et al. |
| 7,101,380 B2 | 9/2006 | Khachin et al. |
| 7,172,614 B2 | 2/2007 | Boyle et al. |
| 7,175,655 B1 | 2/2007 | Molaei |
| 7,179,273 B1 | 2/2007 | Palmer et al. |
| 7,185,922 B2 | 3/2007 | Takayanagi et al. |
| 7,220,271 B2 | 5/2007 | Clubb et al. |
| 7,226,464 B2 | 6/2007 | Garner et al. |
| 7,229,472 B2 | 6/2007 | DePalma et al. |
| 7,241,304 B2 | 7/2007 | Boyle et al. |
| 7,241,308 B2 | 7/2007 | Andreas et al. |
| 7,288,112 B2 | 10/2007 | Denardo et al. |
| 7,300,458 B2 | 11/2007 | Henkes et al. |
| 7,306,618 B2 | 12/2007 | Demond et al. |
| 7,314,483 B2 | 1/2008 | Landau et al. |
| 7,316,692 B2 | 1/2008 | Huffmaster |
| 7,323,001 B2 | 1/2008 | Clubb et al. |
| 7,331,976 B2 | 2/2008 | McGuckin, Jr. et al. |
| 7,344,550 B2 | 3/2008 | Carrison et al. |
| 7,399,308 B2 | 7/2008 | Borillo et al. |
| 7,410,491 B2 | 8/2008 | Hopkins et al. |
| 7,425,215 B2 | 9/2008 | Boyle et al. |
| 7,452,496 B2 | 11/2008 | Brady et al. |
| 7,491,215 B2 | 2/2009 | Vale et al. |
| 7,491,216 B2 | 2/2009 | Brady |
| 7,510,565 B2 | 3/2009 | Gilson et al. |
| 7,534,252 B2 | 5/2009 | Sepetka et al. |
| 7,556,636 B2 | 7/2009 | Mazzocchi et al. |
| 7,582,111 B2 | 9/2009 | Krolik et al. |
| 7,594,926 B2 | 9/2009 | Linder et al. |
| 7,604,649 B2 | 10/2009 | McGuckin, Jr. et al. |
| 7,604,650 B2 | 10/2009 | Bergheim |
| 7,618,434 B2 | 11/2009 | Santra et al. |
| 7,662,165 B2 | 2/2010 | Gilson et al. |
| 7,670,356 B2 | 3/2010 | Mazzocchi et al. |
| 7,678,123 B2 | 3/2010 | Chanduszko |
| 7,691,121 B2 | 4/2010 | Rosenbluth et al. |
| 7,691,124 B2 | 4/2010 | Balgobin |
| 7,708,770 B2 | 5/2010 | Linder et al. |
| 7,717,929 B2 | 5/2010 | Fallman |
| 7,736,385 B2 | 6/2010 | Agnew |
| 7,749,246 B2 | 7/2010 | McGuckin, Jr. et al. |
| 7,758,606 B2 | 7/2010 | Streeter et al. |
| 7,758,611 B2 | 7/2010 | Kato |
| 7,766,934 B2 | 8/2010 | Pal et al. |
| 7,771,452 B2 | 8/2010 | Pal et al. |
| 7,780,694 B2 | 8/2010 | Palmer et al. |
| 7,780,700 B2 | 8/2010 | Frazier et al. |
| 7,811,305 B2 | 10/2010 | Balgobin et al. |
| 7,815,659 B2 | 10/2010 | Conlon et al. |
| 7,819,893 B2 | 10/2010 | Brady et al. |
| 7,828,815 B2 | 11/2010 | Mazzocchi et al. |
| 7,828,816 B2 | 11/2010 | Mazzocchi et al. |
| 7,833,240 B2 | 11/2010 | Okushi et al. |
| 7,842,053 B2 | 11/2010 | Chanduszko et al. |
| 7,846,175 B2 | 12/2010 | Bonnette et al. |
| 7,846,176 B2 | 12/2010 | Gilson et al. |
| 7,850,708 B2 | 12/2010 | Pal |
| 7,883,516 B2 | 2/2011 | Huang et al. |
| 7,887,560 B2 | 2/2011 | Kusleika |
| 7,901,426 B2 | 3/2011 | Gilson et al. |
| 7,914,549 B2 | 3/2011 | Morsi |
| 7,922,732 B2 | 4/2011 | Mazzocchi et al. |

(56) References Cited

U.S. PATENT DOCUMENTS

| | | |
|---|---|---|
| 7,927,784 B2 | 4/2011 | Simpson |
| 7,931,659 B2 | 4/2011 | Bose et al. |
| 7,998,165 B2 | 8/2011 | Huffmaster |
| 8,002,822 B2 | 8/2011 | Glocker et al. |
| 8,021,379 B2 | 9/2011 | Thompson et al. |
| 8,021,380 B2 | 9/2011 | Thompson et al. |
| 8,043,326 B2 | 10/2011 | Hancock et al. |
| 8,048,151 B2 | 11/2011 | OBrien et al. |
| 8,052,640 B2 | 11/2011 | Fiorella et al. |
| 8,057,497 B1 | 11/2011 | Raju et al. |
| 8,057,507 B2 | 11/2011 | Horan et al. |
| 8,066,757 B2 | 11/2011 | Ferrera et al. |
| 8,070,791 B2 | 12/2011 | Ferrera et al. |
| 8,088,140 B2 | 1/2012 | Ferrera et al. |
| 8,100,935 B2 | 1/2012 | Rosenbluth et al. |
| 8,109,941 B2 | 2/2012 | Richardson |
| 8,118,829 B2 | 2/2012 | Carrison et al. |
| 8,118,856 B2 | 2/2012 | Schreck et al. |
| 8,123,769 B2 | 2/2012 | Osborne |
| 8,137,376 B2 | 3/2012 | Clubb et al. |
| 8,137,377 B2 | 3/2012 | Palmer et al. |
| 8,142,422 B2 | 3/2012 | Makower et al. |
| 8,142,442 B2 | 3/2012 | Palmer et al. |
| 8,182,508 B2 | 5/2012 | Magnuson et al. |
| 8,187,298 B2 | 5/2012 | Pal |
| 8,197,493 B2 | 6/2012 | Ferrera et al. |
| 8,246,641 B2 | 8/2012 | Osborne et al. |
| 8,246,672 B2 | 8/2012 | Osborne |
| 8,252,017 B2 | 8/2012 | Paul, Jr. et al. |
| 8,252,018 B2 | 8/2012 | Valaie |
| 8,262,689 B2 | 9/2012 | Schneiderman et al. |
| 8,282,668 B2 | 10/2012 | McGuckin, Jr. et al. |
| 8,298,257 B2 | 10/2012 | Sepetka et al. |
| RE43,882 E | 12/2012 | Hopkins et al. |
| 8,357,178 B2 | 1/2013 | Grandfield et al. |
| 8,357,179 B2 | 1/2013 | Grandfield et al. |
| 8,357,180 B2 | 1/2013 | Feller, III et al. |
| 8,357,893 B2 | 1/2013 | Xu et al. |
| 8,361,095 B2 | 1/2013 | Osborne |
| 8,361,110 B2 | 1/2013 | Chanduszko |
| 8,366,663 B2 | 2/2013 | Fiorella et al. |
| 8,409,215 B2 | 4/2013 | Sepetka et al. |
| 8,414,482 B2 | 4/2013 | Belson |
| 8,414,543 B2 | 4/2013 | McGuckin, Jr. et al. |
| 8,419,748 B2 | 4/2013 | Valaie |
| 8,460,312 B2 | 6/2013 | Bose et al. |
| 8,460,313 B2 | 6/2013 | Huffmaster |
| 8,486,104 B2 | 7/2013 | Samson et al. |
| 8,512,352 B2 | 8/2013 | Martin |
| 8,529,596 B2 | 9/2013 | Grandfield et al. |
| 8,545,526 B2 | 10/2013 | Martin et al. |
| 8,574,262 B2 | 11/2013 | Ferrera et al. |
| 8,579,915 B2 | 11/2013 | French et al. |
| 8,585,713 B2 | 11/2013 | Ferrera et al. |
| 8,608,761 B2 | 12/2013 | Osborne et al. |
| 8,679,142 B2 | 3/2014 | Slee et al. |
| 8,690,907 B1 | 4/2014 | Janardhan et al. |
| 8,696,622 B2 | 4/2014 | Fiorella et al. |
| 8,702,652 B2 | 4/2014 | Fiorella et al. |
| 8,702,704 B2 | 4/2014 | Shelton, IV et al. |
| 8,702,724 B2 | 4/2014 | Olsen et al. |
| 8,777,976 B2 | 7/2014 | Brady et al. |
| 8,777,979 B2 | 7/2014 | Shrivastava et al. |
| 8,784,434 B2 | 7/2014 | Rosenbluth et al. |
| 8,784,441 B2 | 7/2014 | Rosenbluth et al. |
| 8,795,305 B2 | 8/2014 | Martin et al. |
| 8,795,317 B2 | 8/2014 | Grandfield et al. |
| 8,795,345 B2 | 8/2014 | Grandfield et al. |
| 8,814,892 B2 | 8/2014 | Galdonik et al. |
| 8,814,925 B2 | 8/2014 | Hilaire et al. |
| 8,852,205 B2 | 10/2014 | Brady et al. |
| 8,870,941 B2 | 10/2014 | Evans et al. |
| 8,900,265 B1 | 12/2014 | Ulm, III |
| 8,920,358 B2 | 12/2014 | Levine et al. |
| 8,939,991 B2 | 1/2015 | Krolik et al. |
| 8,940,003 B2 | 1/2015 | Slee et al. |
| 8,945,143 B2 | 2/2015 | Ferrera et al. |
| 8,945,160 B2 | 2/2015 | Krolik et al. |
| 8,945,169 B2 | 2/2015 | Pal |
| 8,945,172 B2 | 2/2015 | Ferrera et al. |
| 8,956,399 B2 | 2/2015 | Cam et al. |
| 8,968,330 B2 | 3/2015 | Rosenbluth et al. |
| 9,011,481 B2 | 4/2015 | Aggerholm et al. |
| 9,039,749 B2 | 5/2015 | Shrivastava et al. |
| 9,044,263 B2 | 6/2015 | Grandfield et al. |
| 9,072,537 B2 | 7/2015 | Grandfield et al. |
| 9,095,342 B2 | 8/2015 | Becking et al. |
| 9,113,936 B2 | 8/2015 | Palmer et al. |
| 9,119,656 B2 | 9/2015 | Bose et al. |
| 9,138,307 B2 | 9/2015 | Valaie |
| 9,155,552 B2 | 10/2015 | Ulm, III |
| 9,161,758 B2 | 10/2015 | Figulla et al. |
| 9,161,766 B2 | 10/2015 | Slee et al. |
| 9,173,668 B2 | 11/2015 | Ulm, III |
| 9,186,487 B2 | 11/2015 | Dubrul et al. |
| 9,198,687 B2 | 12/2015 | Fulkerson et al. |
| 9,204,887 B2 | 12/2015 | Cully et al. |
| 9,211,132 B2 | 12/2015 | Bowman |
| 9,232,992 B2 | 1/2016 | Heidner et al. |
| 9,254,371 B2 | 2/2016 | Martin et al. |
| 9,301,769 B2 | 4/2016 | Brady et al. |
| 9,320,532 B2 | 4/2016 | Ferrera et al. |
| 9,332,999 B2 | 5/2016 | Ray et al. |
| 9,387,098 B2 | 7/2016 | Ferrera et al. |
| 9,402,707 B2 | 8/2016 | Brady et al. |
| 9,445,829 B2 | 9/2016 | Brady et al. |
| 9,456,834 B2 | 10/2016 | Folk |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,104 B2 | 2/2017 | Beckham et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,639 B2 | 5/2017 | Brady et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Peterson et al. |

(56) References Cited

U.S. PATENT DOCUMENTS

| | | |
|---|---|---|
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,651 B2 | 10/2017 | Harrah et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,304 B2 | 12/2017 | Horan et al. |
| 9,833,604 B2 | 12/2017 | Lam et al. |
| 9,833,625 B2 | 12/2017 | Waldhauser et al. |
| 9,901,434 B2 | 2/2018 | Hoffman |
| 9,918,720 B2 | 3/2018 | Marchand et al. |
| 10,016,206 B1 | 7/2018 | Yang |
| 10,070,878 B2 | 9/2018 | Ma |
| 10,098,651 B2 | 10/2018 | Marchand et al. |
| 10,201,360 B2 | 2/2019 | Vale et al. |
| 10,231,751 B2 | 3/2019 | Sos |
| 10,292,723 B2 | 5/2019 | Brady et al. |
| 10,299,811 B2 | 5/2019 | Brady et al. |
| 10,363,054 B2 | 7/2019 | Vale et al. |
| 10,376,274 B2 | 8/2019 | Farin et al. |
| 10,390,850 B2 | 8/2019 | Vale et al. |
| 10,524,811 B2 | 1/2020 | Marchand et al. |
| 10,531,942 B2 | 1/2020 | Eggers |
| 10,617,435 B2 | 4/2020 | Vale et al. |
| 10,722,257 B2 | 7/2020 | Skillrud et al. |
| 11,439,418 B2 | 9/2022 | O'Malley |
| 11,517,340 B2 | 12/2022 | Casey |
| 2001/0001315 A1 | 5/2001 | Bates et al. |
| 2001/0016755 A1 | 8/2001 | Addis |
| 2001/0037141 A1 | 11/2001 | Yee et al. |
| 2001/0041909 A1 | 11/2001 | Tsugita et al. |
| 2001/0044632 A1 | 11/2001 | Daniel et al. |
| 2001/0049554 A1 | 12/2001 | Ruiz et al. |
| 2001/0051810 A1 | 12/2001 | Dubrul et al. |
| 2002/0004667 A1 | 1/2002 | Adams et al. |
| 2002/0016609 A1 | 2/2002 | Wensel et al. |
| 2002/0022859 A1 | 2/2002 | Hogendijk |
| 2002/0026211 A1 | 2/2002 | Khosravi et al. |
| 2002/0042627 A1 | 4/2002 | Brady et al. |
| 2002/0049468 A1 | 4/2002 | Streeter et al. |
| 2002/0052620 A1 | 5/2002 | Barbut |
| 2002/0058911 A1 | 5/2002 | Gilson et al. |
| 2002/0068954 A1 | 6/2002 | Foster |
| 2002/0072764 A1 | 6/2002 | Sepetka et al. |
| 2002/0082558 A1 | 6/2002 | Samson et al. |
| 2002/0091407 A1 | 7/2002 | Zando-Azizi et al. |
| 2002/0095171 A1 | 7/2002 | Belef |
| 2002/0123765 A1 | 9/2002 | Sepetka et al. |
| 2002/0128680 A1 | 9/2002 | Pavlovic |
| 2002/0138094 A1 | 9/2002 | Borillo et al. |
| 2002/0143349 A1 | 10/2002 | Gifford, III et al. |
| 2002/0143362 A1 | 10/2002 | Macoviak et al. |
| 2002/0156455 A1 | 10/2002 | Barbut |
| 2002/0161393 A1 | 10/2002 | Demond et al. |
| 2002/0165576 A1 | 11/2002 | Boyle et al. |
| 2002/0173819 A1 | 11/2002 | Leeflang et al. |
| 2002/0183787 A1 | 12/2002 | Wahr et al. |
| 2002/0188276 A1 | 12/2002 | Evans et al. |
| 2002/0188314 A1 | 12/2002 | Anderson et al. |
| 2002/0193824 A1 | 12/2002 | Boylan et al. |
| 2002/0198588 A1 | 12/2002 | Armstrong et al. |
| 2003/0004536 A1 | 1/2003 | Boylan et al. |
| 2003/0004538 A1 | 1/2003 | Secrest et al. |
| 2003/0004540 A1 | 1/2003 | Linder et al. |
| 2003/0004542 A1 | 1/2003 | Wensel et al. |
| 2003/0009146 A1 | 1/2003 | Muni et al. |
| 2003/0009191 A1 | 1/2003 | Wensel et al. |
| 2003/0038447 A1 | 2/2003 | Cantele |
| 2003/0040772 A1 | 2/2003 | Hyodoh et al. |
| 2003/0050663 A1 | 3/2003 | Khachin et al. |
| 2003/0069520 A1 | 4/2003 | Skujins et al. |
| 2003/0114879 A1 | 6/2003 | Euteneuer et al. |
| 2003/0125798 A1 | 7/2003 | Martin |
| 2003/0130682 A1 | 7/2003 | Broome et al. |
| 2003/0144687 A1 | 7/2003 | Brady et al. |
| 2003/0144688 A1 | 7/2003 | Brady et al. |
| 2003/0153943 A1 | 8/2003 | Michael et al. |
| 2003/0153944 A1 | 8/2003 | Phung et al. |
| 2003/0163064 A1 | 8/2003 | Vrba et al. |
| 2003/0163158 A1 | 8/2003 | White |
| 2003/0171769 A1 | 9/2003 | Barbut |
| 2003/0171771 A1 | 9/2003 | Anderson et al. |
| 2003/0176884 A1 | 9/2003 | Berrada et al. |
| 2003/0187495 A1 | 10/2003 | Cully et al. |
| 2003/0195537 A1 | 10/2003 | Dubrul et al. |
| 2003/0195554 A1 | 10/2003 | Shen et al. |
| 2003/0199917 A1 | 10/2003 | Knudson et al. |
| 2003/0204202 A1 | 10/2003 | Palmer et al. |
| 2003/0208224 A1 | 11/2003 | Broome |
| 2003/0212430 A1 | 11/2003 | Bose et al. |
| 2003/0236533 A1 | 12/2003 | Wilson et al. |
| 2004/0064179 A1 | 4/2004 | Linder et al. |
| 2004/0068288 A1 | 4/2004 | Palmer et al. |
| 2004/0073243 A1 | 4/2004 | Sepetka et al. |
| 2004/0079429 A1 | 4/2004 | Miller et al. |
| 2004/0082962 A1 | 4/2004 | Demarais et al. |
| 2004/0082967 A1 | 4/2004 | Broome et al. |
| 2004/0088001 A1 | 5/2004 | Bosma et al. |
| 2004/0093065 A1 | 5/2004 | Yachia et al. |
| 2004/0098050 A1 | 5/2004 | Foerster et al. |
| 2004/0133231 A1 | 7/2004 | Maitland et al. |
| 2004/0133232 A1 | 7/2004 | Rosenbluth et al. |
| 2004/0138692 A1 | 7/2004 | Phung et al. |
| 2004/0153117 A1 | 8/2004 | Clubb et al. |
| 2004/0153118 A1 | 8/2004 | Clubb et al. |
| 2004/0199201 A1 | 10/2004 | Kellett et al. |
| 2004/0204749 A1 | 10/2004 | Gunderson |
| 2004/0215318 A1 | 10/2004 | Kwitkin |
| 2004/0220663 A1 | 11/2004 | Rivelli |
| 2005/0010245 A1 | 1/2005 | Wasicek |
| 2005/0033348 A1 | 2/2005 | Sepetka et al. |
| 2005/0038447 A1 | 2/2005 | Huffmaster |
| 2005/0038468 A1 | 2/2005 | Panetta et al. |
| 2005/0043759 A1 | 2/2005 | Chanduszko |
| 2005/0049619 A1 | 3/2005 | Sepetka et al. |
| 2005/0049669 A1 | 3/2005 | Jones et al. |
| 2005/0049670 A1 | 3/2005 | Jones et al. |
| 2005/0055033 A1 | 3/2005 | Leslie et al. |
| 2005/0055047 A1 | 3/2005 | Greenhalgh |
| 2005/0059995 A1 | 3/2005 | Sepetka et al. |
| 2005/0085849 A1 | 4/2005 | Sepetka et al. |
| 2005/0090779 A1 | 4/2005 | Osypka |
| 2005/0090857 A1 | 4/2005 | Kusleika et al. |
| 2005/0125024 A1 | 6/2005 | Sepetka et al. |
| 2005/0171566 A1 | 8/2005 | Kanamaru |
| 2005/0192627 A1 | 9/2005 | Whisenant et al. |
| 2005/0215942 A1 | 9/2005 | Abrahamson et al. |
| 2005/0216030 A1 | 9/2005 | Sepetka et al. |
| 2005/0216050 A1 | 9/2005 | Sepetka et al. |
| 2005/0228417 A1 | 10/2005 | Teitelbaum et al. |
| 2005/0251206 A1 | 11/2005 | Maahs et al. |
| 2005/0251209 A1 | 11/2005 | Saadat et al. |
| 2005/0267491 A1 | 12/2005 | Kellett et al. |
| 2005/0273135 A1 | 12/2005 | Chanduszko et al. |
| 2005/0283186 A1 | 12/2005 | Berrada et al. |
| 2005/0288686 A1 | 12/2005 | Sepetka et al. |
| 2006/0009798 A1 | 1/2006 | Callister et al. |
| 2006/0009799 A1 | 1/2006 | Kleshinski et al. |
| 2006/0020285 A1 | 1/2006 | Niermann |
| 2006/0020286 A1 | 1/2006 | Niermann |
| 2006/0030877 A1 | 2/2006 | Martinez et al. |
| 2006/0041228 A1 | 2/2006 | Vo et al. |
| 2006/0058836 A1 | 3/2006 | Bose et al. |
| 2006/0058837 A1 | 3/2006 | Bose et al. |
| 2006/0058838 A1 | 3/2006 | Bose et al. |
| 2006/0064151 A1 | 3/2006 | Guterman et al. |
| 2006/0069424 A1 | 3/2006 | Acosta et al. |
| 2006/0074477 A1 | 4/2006 | Berthiaume et al. |
| 2006/0142838 A1 | 6/2006 | Molaei et al. |
| 2006/0149313 A1 | 7/2006 | Arguello et al. |
| 2006/0155305 A1 | 7/2006 | Freudenthal et al. |
| 2006/0161187 A1 | 7/2006 | Levine et al. |
| 2006/0195137 A1 | 8/2006 | Sepetka et al. |

(56) References Cited

U.S. PATENT DOCUMENTS

| | | |
|---|---|---|
| 2006/0224177 A1 | 10/2006 | Finitsis |
| 2006/0224179 A1 | 10/2006 | Kucharczyk et al. |
| 2006/0229638 A1 | 10/2006 | Abrams et al. |
| 2006/0235501 A1 | 10/2006 | Igaki |
| 2006/0241677 A1 | 10/2006 | Johnson et al. |
| 2006/0282111 A1 | 12/2006 | Morsi |
| 2006/0287668 A1 | 12/2006 | Fawzi et al. |
| 2006/0287701 A1 | 12/2006 | Pal |
| 2006/0293706 A1 | 12/2006 | Shimon |
| 2007/0010857 A1 | 1/2007 | Sugimoto et al. |
| 2007/0032879 A1 | 2/2007 | Levine et al. |
| 2007/0088382 A1 | 4/2007 | Bei et al. |
| 2007/0088383 A1 | 4/2007 | Pal et al. |
| 2007/0100348 A1 | 5/2007 | Cauthen, III et al. |
| 2007/0118173 A1 | 5/2007 | Magnuson et al. |
| 2007/0149997 A1 | 6/2007 | Muller |
| 2007/0156170 A1 | 7/2007 | Hancock et al. |
| 2007/0165170 A1 | 7/2007 | Fukuda |
| 2007/0179527 A1 | 8/2007 | Eskuri et al. |
| 2007/0191866 A1 | 8/2007 | Palmer et al. |
| 2007/0198028 A1 | 8/2007 | Miloslavski et al. |
| 2007/0198051 A1 | 8/2007 | Clubb et al. |
| 2007/0198075 A1 | 8/2007 | Levy |
| 2007/0208367 A1 | 9/2007 | Fiorella et al. |
| 2007/0208371 A1 | 9/2007 | French et al. |
| 2007/0225749 A1 | 9/2007 | Martin et al. |
| 2007/0233175 A1 | 10/2007 | Zaver et al. |
| 2007/0244505 A1 | 10/2007 | Gilson et al. |
| 2007/0270902 A1 | 11/2007 | Slazas et al. |
| 2007/0288054 A1 | 12/2007 | Tanaka et al. |
| 2008/0045881 A1 | 2/2008 | Teitelbaum et al. |
| 2008/0077227 A1 | 3/2008 | Ouellette et al. |
| 2008/0082107 A1 | 4/2008 | Miller et al. |
| 2008/0086190 A1 | 4/2008 | Ta |
| 2008/0091223 A1 | 4/2008 | Pokorney et al. |
| 2008/0097386 A1 | 4/2008 | Osypka |
| 2008/0109031 A1 | 5/2008 | Sepetka et al. |
| 2008/0109032 A1 | 5/2008 | Sepetka et al. |
| 2008/0119886 A1 | 5/2008 | Greenhalgh et al. |
| 2008/0125798 A1 | 5/2008 | Osborne et al. |
| 2008/0177296 A1 | 7/2008 | Sepetka et al. |
| 2008/0178890 A1 | 7/2008 | Townsend et al. |
| 2008/0183197 A1 | 7/2008 | Sepetka et al. |
| 2008/0183198 A1 | 7/2008 | Sepetka et al. |
| 2008/0183205 A1 | 7/2008 | Sepetka et al. |
| 2008/0188876 A1 | 8/2008 | Sepetka et al. |
| 2008/0188885 A1 | 8/2008 | Sepetka et al. |
| 2008/0188887 A1 | 8/2008 | Batiste |
| 2008/0200946 A1 | 8/2008 | Braun et al. |
| 2008/0200947 A1 | 8/2008 | Kusleika et al. |
| 2008/0215077 A1 | 9/2008 | Sepetka et al. |
| 2008/0221600 A1 | 9/2008 | Dieck et al. |
| 2008/0228209 A1 | 9/2008 | DeMello et al. |
| 2008/0234706 A1 | 9/2008 | Sepetka et al. |
| 2008/0243170 A1 | 10/2008 | Jenson et al. |
| 2008/0255596 A1 | 10/2008 | Jenson et al. |
| 2008/0262410 A1 | 10/2008 | Jenson et al. |
| 2008/0262528 A1 | 10/2008 | Martin |
| 2008/0262532 A1 | 10/2008 | Martin |
| 2008/0262590 A1 | 10/2008 | Murray |
| 2008/0269871 A1 | 10/2008 | Eli |
| 2008/0275488 A1 | 11/2008 | Fleming |
| 2008/0275493 A1 | 11/2008 | Farmiga |
| 2008/0281350 A1 | 11/2008 | Sepetka et al. |
| 2008/0312681 A1 | 12/2008 | Ansel et al. |
| 2009/0005858 A1 | 1/2009 | Young et al. |
| 2009/0024157 A1 | 1/2009 | Anukhin |
| 2009/0030443 A1 | 1/2009 | Buser et al. |
| 2009/0062841 A1 | 3/2009 | Amplatz et al. |
| 2009/0069828 A1 | 3/2009 | Martin et al. |
| 2009/0076539 A1 | 3/2009 | Valaie |
| 2009/0088793 A1 | 4/2009 | Bagaoisan et al. |
| 2009/0088795 A1 | 4/2009 | Cahill |
| 2009/0105722 A1 | 4/2009 | Fulkerson et al. |
| 2009/0105737 A1 | 4/2009 | Fulkerson et al. |
| 2009/0105747 A1 | 4/2009 | Chanduszko et al. |
| 2009/0149881 A1 | 6/2009 | Vale et al. |
| 2009/0163851 A1 | 6/2009 | Holloway et al. |
| 2009/0177206 A1 | 7/2009 | Lozier et al. |
| 2009/0182336 A1 | 7/2009 | Brenzel et al. |
| 2009/0281610 A1 | 11/2009 | Parker |
| 2009/0281619 A1 | 11/2009 | Le et al. |
| 2009/0287229 A1 | 11/2009 | Ogdahl |
| 2009/0292297 A1 | 11/2009 | Ferrere |
| 2009/0292307 A1 | 11/2009 | Razack |
| 2009/0299393 A1 | 12/2009 | Martin et al. |
| 2009/0299403 A1 | 12/2009 | Chanduszko et al. |
| 2009/0306702 A1 | 12/2009 | Miloslavski et al. |
| 2009/0326636 A1 | 12/2009 | Hashimoto et al. |
| 2010/0004607 A1 | 1/2010 | Wilson et al. |
| 2010/0076482 A1 | 3/2010 | Shu et al. |
| 2010/0087850 A1 | 4/2010 | Razack |
| 2010/0087908 A1 | 4/2010 | Hilaire et al. |
| 2010/0114017 A1 | 5/2010 | Lenker et al. |
| 2010/0125326 A1 | 5/2010 | Kalstad et al. |
| 2010/0125327 A1 | 5/2010 | Agnew |
| 2010/0191272 A1 | 7/2010 | Keating |
| 2010/0211094 A1 | 8/2010 | Sargent, Jr. |
| 2010/0268264 A1 | 10/2010 | Bonnette et al. |
| 2010/0268265 A1 | 10/2010 | Krolik et al. |
| 2010/0274277 A1 | 10/2010 | Eaton |
| 2010/0318178 A1 | 12/2010 | Rapaport et al. |
| 2010/0324649 A1 | 12/2010 | Mattsson et al. |
| 2010/0331949 A1 | 12/2010 | Habib |
| 2011/0009875 A1 | 1/2011 | Grandfield et al. |
| 2011/0009940 A1 | 1/2011 | Grandfield et al. |
| 2011/0009950 A1 | 1/2011 | Grandfield et al. |
| 2011/0015718 A1 | 1/2011 | Schreck |
| 2011/0022149 A1 | 1/2011 | Cox et al. |
| 2011/0040319 A1 | 2/2011 | Fulton, III |
| 2011/0054287 A1 | 3/2011 | Schultz |
| 2011/0054504 A1 | 3/2011 | Porter |
| 2011/0054514 A1 | 3/2011 | Arcand et al. |
| 2011/0054516 A1 | 3/2011 | Keegan et al. |
| 2011/0060212 A1 | 3/2011 | Slee et al. |
| 2011/0060359 A1 | 3/2011 | Hannes et al. |
| 2011/0106137 A1 | 5/2011 | Shimon |
| 2011/0125181 A1 | 5/2011 | Brady et al. |
| 2011/0152920 A1 | 6/2011 | Eckhouse et al. |
| 2011/0160763 A1 | 6/2011 | Ferrera et al. |
| 2011/0166586 A1 | 7/2011 | Sepetka et al. |
| 2011/0184456 A1 | 7/2011 | Grandfield et al. |
| 2011/0196414 A1 | 8/2011 | Porter et al. |
| 2011/0202088 A1 | 8/2011 | Eckhouse et al. |
| 2011/0208233 A1 | 8/2011 | McGuckin, Jr. et al. |
| 2011/0213297 A1 | 9/2011 | Aklog et al. |
| 2011/0213393 A1 | 9/2011 | Aklog et al. |
| 2011/0213403 A1 | 9/2011 | Aboytes |
| 2011/0224707 A1 | 9/2011 | Miloslavski et al. |
| 2011/0270374 A1 | 11/2011 | Orr et al. |
| 2011/0276120 A1 | 11/2011 | Gilson et al. |
| 2011/0319917 A1 | 12/2011 | Ferrera et al. |
| 2012/0022572 A1 | 1/2012 | Braun et al. |
| 2012/0041449 A1 | 2/2012 | Eckhouse et al. |
| 2012/0041474 A1 | 2/2012 | Eckhouse et al. |
| 2012/0059356 A1 | 3/2012 | di Palma et al. |
| 2012/0065660 A1 | 3/2012 | Ferrera et al. |
| 2012/0083823 A1 | 4/2012 | Shrivastava et al. |
| 2012/0083868 A1 | 4/2012 | Shrivastava et al. |
| 2012/0089216 A1 | 4/2012 | Rapaport et al. |
| 2012/0101510 A1 | 4/2012 | Lenker et al. |
| 2012/0116440 A1 | 5/2012 | Leynov et al. |
| 2012/0123466 A1 | 5/2012 | Porter et al. |
| 2012/0143230 A1 | 6/2012 | Sepetka et al. |
| 2012/0143237 A1 | 6/2012 | Cam et al. |
| 2012/0143317 A1 | 6/2012 | Cam et al. |
| 2012/0150147 A1 | 6/2012 | Leynov et al. |
| 2012/0165858 A1 | 6/2012 | Eckhouse et al. |
| 2012/0165859 A1 | 6/2012 | Eckhouse et al. |
| 2012/0209312 A1 | 8/2012 | Aggerholm et al. |
| 2012/0215250 A1 | 8/2012 | Grandfield et al. |
| 2012/0277788 A1 | 11/2012 | Cattaneo |
| 2012/0283768 A1 | 11/2012 | Cox et al. |
| 2012/0296362 A1 | 11/2012 | Cam et al. |

(56) References Cited

U.S. PATENT DOCUMENTS

| | | |
|---|---|---|
| 2012/0316600 A1 | 12/2012 | Ferrera et al. |
| 2012/0330350 A1 | 12/2012 | Jones et al. |
| 2013/0030460 A1 | 1/2013 | Marks et al. |
| 2013/0030461 A1 | 1/2013 | Marks et al. |
| 2013/0046330 A1 | 2/2013 | McIntosh et al. |
| 2013/0046333 A1 | 2/2013 | Jones et al. |
| 2013/0046334 A1 | 2/2013 | Jones et al. |
| 2013/0116774 A1 | 5/2013 | Strauss et al. |
| 2013/0131614 A1 | 5/2013 | Hassan et al. |
| 2013/0144311 A1 | 6/2013 | Fung et al. |
| 2013/0144326 A1 | 6/2013 | Brady et al. |
| 2013/0158591 A1 | 6/2013 | Koehler |
| 2013/0158592 A1 | 6/2013 | Porter |
| 2013/0184739 A1 | 7/2013 | Brady et al. |
| 2013/0197567 A1 | 8/2013 | Brady et al. |
| 2013/0226146 A1 | 8/2013 | Tekulve |
| 2013/0268050 A1 | 10/2013 | Wilson et al. |
| 2013/0281788 A1 | 10/2013 | Garrison |
| 2013/0325051 A1 | 12/2013 | Martin et al. |
| 2013/0325055 A1 | 12/2013 | Eckhouse et al. |
| 2013/0325056 A1 | 12/2013 | Eckhouse et al. |
| 2013/0345739 A1 | 12/2013 | Brady et al. |
| 2014/0005712 A1 | 1/2014 | Martin |
| 2014/0005713 A1 | 1/2014 | Bowman |
| 2014/0046359 A1 | 2/2014 | Bowman et al. |
| 2014/0088678 A1 | 3/2014 | Wainwright et al. |
| 2014/0121672 A1 | 5/2014 | Folk |
| 2014/0128905 A1 | 5/2014 | Molaei |
| 2014/0134654 A1 | 5/2014 | Rudel et al. |
| 2014/0135812 A1 | 5/2014 | Divino et al. |
| 2014/0142598 A1 | 5/2014 | Fulton, III |
| 2014/0163367 A1 | 6/2014 | Eskuri |
| 2014/0180122 A1 | 6/2014 | Stigall et al. |
| 2014/0180377 A1 | 6/2014 | Bose et al. |
| 2014/0180397 A1 | 6/2014 | Gerberding et al. |
| 2014/0194911 A1 | 7/2014 | Johnson et al. |
| 2014/0194919 A1 | 7/2014 | Losordo et al. |
| 2014/0200607 A1 | 7/2014 | Sepetka et al. |
| 2014/0200608 A1 | 7/2014 | Brady et al. |
| 2014/0236220 A1 | 8/2014 | Inoue |
| 2014/0243881 A1 | 8/2014 | Lees et al. |
| 2014/0257362 A1 | 9/2014 | Eidenschink |
| 2014/0276922 A1 | 9/2014 | McLain et al. |
| 2014/0277079 A1 | 9/2014 | Vale et al. |
| 2014/0303667 A1 | 10/2014 | Cox et al. |
| 2014/0309657 A1 | 10/2014 | Ben-Ami |
| 2014/0309673 A1 | 10/2014 | Dacuycuy et al. |
| 2014/0330302 A1 | 11/2014 | Tekulve et al. |
| 2014/0343585 A1 | 11/2014 | Ferrera et al. |
| 2014/0371769 A1 | 12/2014 | Vale et al. |
| 2014/0371779 A1 | 12/2014 | Vale et al. |
| 2014/0371780 A1 | 12/2014 | Vale et al. |
| 2014/0379023 A1 | 12/2014 | Brady et al. |
| 2015/0018859 A1 | 1/2015 | Quick et al. |
| 2015/0018860 A1 | 1/2015 | Quick et al. |
| 2015/0032144 A1 | 1/2015 | Holloway |
| 2015/0080937 A1 | 3/2015 | Davidson |
| 2015/0112376 A1 | 4/2015 | Molaei et al. |
| 2015/0133990 A1 | 5/2015 | Davidson |
| 2015/0150672 A1 | 6/2015 | Ma |
| 2015/0164523 A1 | 6/2015 | Brady et al. |
| 2015/0224133 A1 | 8/2015 | Ohri et al. |
| 2015/0250497 A1 | 9/2015 | Marks et al. |
| 2015/0257775 A1 | 9/2015 | Gilvarry et al. |
| 2015/0272716 A1 | 10/2015 | Pinchuk et al. |
| 2015/0297252 A1 | 10/2015 | Miloslavski et al. |
| 2015/0313617 A1 | 11/2015 | Grandfield et al. |
| 2015/0320431 A1 | 11/2015 | Ulm |
| 2015/0352325 A1 | 12/2015 | Quick |
| 2015/0359547 A1 | 12/2015 | Vale et al. |
| 2015/0366650 A1 | 12/2015 | Zi et al. |
| 2015/0374391 A1 | 12/2015 | Quick et al. |
| 2015/0374393 A1 | 12/2015 | Brady et al. |
| 2015/0374479 A1 | 12/2015 | Vale |
| 2016/0015402 A1 | 1/2016 | Brady et al. |
| 2016/0022296 A1 | 1/2016 | Brady et al. |
| 2016/0045298 A1 | 2/2016 | Thinnes, Jr. et al. |
| 2016/0066921 A1 | 3/2016 | Seifert et al. |
| 2016/0100928 A1 | 4/2016 | Lees et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113664 A1 | 4/2016 | Brady et al. |
| 2016/0113665 A1 | 4/2016 | Brady et al. |
| 2016/0120558 A1 | 5/2016 | Brady et al. |
| 2016/0143653 A1 | 5/2016 | Vale et al. |
| 2016/0192953 A1 | 7/2016 | Brady et al. |
| 2016/0192954 A1 | 7/2016 | Brady et al. |
| 2016/0192955 A1 | 7/2016 | Brady et al. |
| 2016/0192956 A1 | 7/2016 | Brady et al. |
| 2016/0256180 A1 | 9/2016 | Vale et al. |
| 2016/0303381 A1 | 10/2016 | Pierce et al. |
| 2016/0317168 A1 | 11/2016 | Brady et al. |
| 2017/0007264 A1 | 1/2017 | Cruise et al. |
| 2017/0007265 A1 | 1/2017 | Guo et al. |
| 2017/0020542 A1 | 1/2017 | Martin et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0056061 A1 | 3/2017 | Ogle et al. |
| 2017/0071614 A1 | 3/2017 | Vale et al. |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086862 A1 | 3/2017 | Vale et al. |
| 2017/0086863 A1 | 3/2017 | Brady et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Grandfield |
| 2017/0100183 A1 | 4/2017 | Iaizzo et al. |
| 2017/0105743 A1 | 4/2017 | Vale et al. |
| 2017/0112515 A1 | 4/2017 | Brady et al. |
| 2017/0112647 A1 | 4/2017 | Sachar et al. |
| 2017/0113023 A1 | 4/2017 | Steingisser et al. |
| 2017/0119409 A1 | 5/2017 | Ma |
| 2017/0143465 A1 | 5/2017 | Ulm, III |
| 2017/0147765 A1 | 5/2017 | Mehta |
| 2017/0150979 A1 | 6/2017 | Ulm |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0189041 A1 | 7/2017 | Cox et al. |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |

(56) References Cited

U.S. PATENT DOCUMENTS

| | | |
|---|---|---|
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2018/0140315 A1 | 5/2018 | Bowman et al. |
| 2018/0206865 A1 | 7/2018 | Martin et al. |
| 2018/0207399 A1 | 7/2018 | Chou et al. |
| 2018/0263650 A1 | 9/2018 | Iwanami et al. |
| 2018/0325537 A1 | 11/2018 | Shamay et al. |
| 2018/0326024 A1 | 11/2018 | Prochazka et al. |
| 2018/0344338 A1 | 12/2018 | Brady et al. |
| 2019/0000492 A1 | 1/2019 | Casey et al. |
| 2019/0015061 A1 | 1/2019 | Liebeskind et al. |
| 2019/0167284 A1 | 6/2019 | Friedman et al. |
| 2019/0239907 A1 | 8/2019 | Brady et al. |
| 2019/0292273 A1 | 9/2019 | Hanotin et al. |
| 2019/0374239 A1 | 12/2019 | Martin et al. |
| 2019/0380723 A1 | 12/2019 | Grandfield et al. |
| 2019/0388097 A1 | 12/2019 | Girdhar et al. |
| 2020/0000483 A1 | 1/2020 | Brady et al. |
| 2020/0009150 A1 | 1/2020 | Chamorro Sanchez |
| 2020/0085444 A1 | 3/2020 | Vale et al. |
| 2020/0100804 A1 | 4/2020 | Casey et al. |
| 2020/0297364 A1 | 9/2020 | Choe et al. |
| 2020/0390459 A1 | 12/2020 | Casey et al. |
| 2021/0005321 A1 | 1/2021 | Hwang |
| 2021/0007757 A1 | 1/2021 | Casey et al. |
| 2021/0228223 A1 | 7/2021 | Casey et al. |
| 2022/0192739 A1 | 6/2022 | Deen et al. |

FOREIGN PATENT DOCUMENTS

| | | |
|---|---|---|
| CN | 102307613 A | 1/2012 |
| CN | 102316809 A | 1/2012 |
| CN | 102596098 A | 7/2012 |
| CN | 103764049 A | 4/2014 |
| CN | 104042304 A | 9/2014 |
| CN | 105208950 A | 12/2015 |
| CN | 105662532 A | 6/2016 |
| CN | 205359559 U | 7/2016 |
| CN | 107530090 A | 1/2018 |
| CN | 208582467 U | 3/2019 |
| DE | 202009001951 U1 | 3/2010 |
| DE | 102009056450 A1 | 6/2011 |
| DE | 102010010849 A1 | 9/2011 |
| DE | 102010014778 A1 | 10/2011 |
| DE | 102010024085 A1 | 12/2011 |
| DE | 102011014586 B3 | 9/2012 |
| EP | 1153581 A1 | 11/2001 |
| EP | 2301450 A1 | 3/2011 |
| EP | 2438891 A1 | 4/2012 |
| EP | 2628455 A1 | 8/2013 |
| EP | 3156004 A1 | 4/2017 |
| EP | 3669802 A1 | 12/2019 |
| EP | 3593742 A1 | 1/2020 |
| EP | 3858291 A1 | 8/2021 |
| ES | 2210456 T3 | 7/2004 |
| GB | 2427554 A | 1/2007 |
| GB | 2494820 A | 3/2013 |
| JP | 09-19438 A | 1/1997 |
| JP | 2014-511223 A | 5/2014 |
| JP | 2014-525796 A | 10/2014 |
| JP | 2015-505250 A | 2/2015 |
| JP | 2016-513505 A | 5/2016 |
| JP | 2019-526365 A | 9/2019 |
| WO | WO 94/24926 A1 | 11/1994 |
| WO | WO 97/27808 A1 | 8/1997 |
| WO | WO 97/38631 A1 | 10/1997 |
| WO | WO 99/20335 A1 | 4/1999 |
| WO | WO 99/56801 A2 | 11/1999 |
| WO | WO 99/60933 A1 | 12/1999 |
| WO | WO 01/21077 A1 | 3/2001 |
| WO | WO 02/02162 A2 | 1/2002 |
| WO | WO 02/11627 A2 | 2/2002 |
| WO | WO 02/43616 A2 | 6/2002 |
| WO | WO 02/070061 A1 | 9/2002 |
| WO | WO 02/094111 A2 | 11/2002 |
| WO | WO 03/002006 A1 | 1/2003 |
| WO | WO 03/030751 A1 | 4/2003 |
| WO | WO 03/051448 A2 | 6/2003 |
| WO | WO 2004/028571 A2 | 4/2004 |
| WO | WO 2004/056275 A1 | 7/2004 |
| WO | WO 2005/000130 A1 | 1/2005 |
| WO | WO 2005/027779 A2 | 3/2005 |
| WO | WO 2006/021407 A2 | 3/2006 |
| WO | WO 2006/031410 A2 | 3/2006 |
| WO | WO 2006/107641 A2 | 10/2006 |
| WO | WO 2006/135823 A2 | 12/2006 |
| WO | WO 2007/054307 A2 | 5/2007 |
| WO | WO 2007/068424 A2 | 6/2007 |
| WO | WO 2008/034615 A2 | 3/2008 |
| WO | WO 2008/051431 A1 | 5/2008 |
| WO | WO 2008/131116 A1 | 10/2008 |
| WO | WO 2008/135823 A1 | 11/2008 |
| WO | WO 2009/031338 A1 | 3/2009 |
| WO | WO 2009/076482 A1 | 6/2009 |
| WO | WO 2009/086482 A1 | 7/2009 |
| WO | WO 2009/105710 A1 | 8/2009 |
| WO | WO 2010/010545 A1 | 1/2010 |
| WO | WO 2010/046897 A1 | 4/2010 |
| WO | WO 2010/075565 A2 | 7/2010 |
| WO | WO 2010/102307 A1 | 9/2010 |
| WO | WO 2010/146581 A1 | 12/2010 |
| WO | WO 2011/013556 A1 | 2/2011 |
| WO | WO 2011/066961 A1 | 6/2011 |
| WO | WO 2011/082319 A1 | 7/2011 |
| WO | WO 2011/095352 A1 | 8/2011 |
| WO | WO 2011/106426 A1 | 9/2011 |
| WO | WO 2011/110316 A1 | 9/2011 |
| WO | WO 2011/135556 A1 | 11/2011 |
| WO | WO 2012/052982 A1 | 4/2012 |
| WO | WO 2012/064726 A1 | 5/2012 |
| WO | WO 2012/081020 A1 | 6/2012 |
| WO | WO 2012/110619 A1 | 8/2012 |
| WO | WO 2012/120490 A2 | 9/2012 |
| WO | WO 2012/156924 A1 | 11/2012 |
| WO | WO 2013/016435 A1 | 1/2013 |
| WO | WO 2013/072777 A2 | 5/2013 |
| WO | WO 2013/105099 A2 | 7/2013 |
| WO | WO 2013/109756 A1 | 7/2013 |
| WO | WO 2013/187927 A1 | 12/2013 |
| WO | WO 2014/047650 A1 | 3/2014 |
| WO | WO 2014/081892 A1 | 5/2014 |
| WO | WO 2014/139845 A1 | 9/2014 |
| WO | WO 2014/169266 A1 | 10/2014 |
| WO | WO 2014/178198 A1 | 11/2014 |
| WO | WO 2015/061365 A1 | 4/2015 |
| WO | WO 2015/103547 A1 | 7/2015 |
| WO | WO 2015/134625 A1 | 9/2015 |
| WO | WO 2015/179324 A2 | 11/2015 |
| WO | WO 2015/189354 A1 | 12/2015 |
| WO | WO 2016/010995 A1 | 1/2016 |

(56) References Cited

FOREIGN PATENT DOCUMENTS

| | | |
|---|---|---|
| WO | WO 2016/089451 A1 | 6/2016 |
| WO | WO 2017/089424 A1 | 6/2017 |
| WO | WO 2017/090473 A1 | 6/2017 |
| WO | WO 2017/103686 A2 | 6/2017 |
| WO | WO 2017/161204 A1 | 9/2017 |
| WO | WO 2020/039082 A1 | 2/2020 |
| WO | WO 2021/113302 A1 | 6/2021 |

OTHER PUBLICATIONS

Loh Y, Jahan R, McArthur D. Recanalization rates decrease with increasing thrombectomy attempts. American Journal of Neuroradiology. May 2010;31(5):935-9.

Arai D, Ishii A, Chihara H, Ikeda H, Miyamoto S. Histological examination of vascular damage caused by stent retriever thrombectomy devices, J Neurointerv Surg. Oct. 2016;8(10):992-5.

Eugène F, Gauvrit J-Y, Ferré J-C, Gentric J-C, Besseghir A, Ronzière T, et al. One-year MR angiographic and clinical follow-up after intracranial mechanical thrombectomy using a stent retriever device, AJNR Am J Neuroradiol. Jan. 2015;36(1):126-32 (18).

Zaidat OO, Castonguay AC, Gupta R, Sun CJ, Martin C, Holloway WE, et al. The first pass effect: a new measure for stroke thrombectomy devices. Stroke. 2018; 49;660-666.

Chueh JY, Marosfoi MG, Brooks OW, King RM, Puri AS, Gounis MJ. Novel distal emboli protection technology: the EmboTrap. Interv Neurol. 2017;6:268-276. doi: 10.1159/000480668.

Nogueira RG, Lutsept HL, Gupta R, Jovin TG, Albers GW, Walker GA, Liebeskind DS, Smith WS. Trevo 2 Trialists. Trevo versus Merci retrievers for thrombectomy revascularisation of large vessel occlusions in acute ischaemic stroke (Trevo 2): a randomised trial. Lancet. 2012;380:1231-1240. doi: 10.1016/S0140-6736(12)61299-9.

Powers WJ, Derdeyn CP, Biller J, Coffey CS, Hoh BL, Jauch EC, et al; American Heart Association Stroke Council. 2015 American Heart Association/American Stroke Association focused update of the 2013 guidelines for the early management of patients with acute ischemic stroke regarding endovascular treatment: a guideline for healthcare professionals from the American Heart Association/American Stroke Association. Stroke. 2015; 46:3020-3035. doi: 10.1161/STR.0000000000000074.

Goyal M, Menon BK, van Zwam WH, Dippel DW, Mitchell PJ, Demchuk AM, et al; Hermes Collaborators. Endovascular thrombectomy after large-vessel ischaemic stroke: a meta-analysis of individual patient data from five randomised trials. Lancet. 2016; 387:1723-1731. doi: 10.1016/S0140-6736(16)00163-X.

Raoult H, Redjem H, Bourcier R, Gaultier-Lintia A, Daumas-Duport B, Ferre J-C, et al. Mechanical thrombectomy with the ERIC retrieval device: initial experience. Journal of NeuroInterventional Surgery. 2016; neurintsurg-2016-012379.

| | |
|---|---|
| Total Population, n | 80 |
| Age (year), median (range) | 72 (34-93) |
| Gender, n (%) | |
| Male | 44 (55.0) |
| Female | 36 (45.0) |
| Cardiovascular risk factors, n (%) | |
| Diabetes mellitus | 9 (11.2) |
| Obesity | 12 (15.0) |
| Smoking | 18 (22.5) |
| High blood pressure | 48 (60.0) |
| Hyperlipidemia<br>Occlusion site, n (%)<br>Tandem occlusion<br>ICA | 31 (38.7)<br>7 (8.7)<br>19 (23.7) |
| MCA (M1, M2) | 79 (98.7) |
| Side right – left | 35 (43.7) – 45 (56.2) |
| NIHSS at baseline, median (range) | 15 (5-30) |
| Initial ASPECT score, median (range)<br>Wake-up stroke, n (%)<br>IV tPA, n (%) | 8 (1-10)<br>19 (23.7)<br>45 (56.2) |

Fig. 5

| | |
|---|---|
| Use of device 200, n (%) | 80 (100.0) |
| As first line | 78 (97.5) |
| Only EmboTrap (- rescue) | 68 (85.0) |
| With second device (+ rescue) | 10 (12.5) |
| As second-line device | 2 (2.5) |
| Number of attempts, median (range) | 1 (1-9) |
| Symptom onset to revascularization time in min, median (range) | |
| Onset to groin puncture | 198 (60 – 230) |
| Puncture to revascularization | 35 (8 – 161) |
| Onset to revascularization | 238 (104 – 685) |

Fig. 6

| Recanalization rates (achieved with device 200), n (%) | |
|---|---|
| mTICI 2b or 3 | 65 (81.3) |
| mTICI 2b or 3 in 1 or 2 passes | 49 (61.3) |
| mTICI 3 | 45 (56.3) |
| mTICI 3 in 1 pass | 34 (42.5) |
| Recanalization rates (entire series), mTICI 2b or 3, n (%) | 72 (90.0) |
| Clinical outcome (entire series) | |
| mRS at 3 months, median (range) | 2 (0-6) |
| mRS ≤ 2 at 3 months, n (%) <br> mRS ≤ 2 at 3 months for all patients with mTICI 3 <br> Complications, n (%) | 49/78 (62.8) <br> 37/48 (77.1) |
| Embolus in new territory | 5 (6.3) |
| Vessel perforations | 0 (0.0) |
| Vasospasms | 3 (3.8) |
| Intracranial hemorrhage, at day 1, n (%) | 17 (21.3) |
| Subarachnoid hemorrhage <br> Symptomatic intracranial hemorrhage, n (%) | 0 (0.0) <br> 5 (6.3) |
| NIHSS at day 1, median (range) | 7 (0-26) |

Fig. 7

| | BGC group (n=37) | Non-BGC group (n=43) | p-value |
|---|---|---|---|
| Age (mean) | 73 | 69 | 0.093 |
| Female gender (n, %) | 21, 57% | 15, 35% | 0.071 |
| Tandem occlusions (n, %) | 3, 8% | 4, 9% | 1 |
| ICA occlusions (n, %) | 8, 22% | 11, 26% | 0.794 |
| IVT (n, %) | 19, 51% | 26, 60% | 0.5 |
| Initial NIHSS (median) | 15 | 15 | 0.817 |
| ASPECTS (median) | 10 | 7 | *0.0001 |
| Onset to groin puncture time, min (mean) | 175 | 244 | *0.001 |
| mTICI 3 (n, %) | 28, 76% | 21, 49% | *0.021 |
| Distal embolization in previously unaffected territory (n, %) | 0, 0% | 5, 12% | 0.058 |
| mRS 0-2 (n, %) | 29, 78% | 20, 47% | *0.004 |
| Groin to revascularization time, min (mean) | 26.7 | 54.7 | *<0.0001 |
| Number of passes (median) | 2 | 1 | 0.912 |

Fig. 9

|  | Device 200 of this Disclosure | TREVO 2 | SWIFT |
|---|---|---|---|
|  | Treated (n=227) | Trevo Arm (n=88) | Solitaire Arm (n=58) |
| Age, y; mean (SD) | 68.0 (13.0) | 67.4 (13.9) | 67.1 (12.0) |
| Male sex, n (%) | 104 (45.8) | 40.0 (45.0) | 280 (48.0) |
| NIHSS score |  |  |  |
| Mean (SD) | 15.8 (5) | 18.3 (5.3) | 17.3 (4.5) |
| Median (IQR) | 16.0 (12.0–19.0)† | 19 (14.0–21.3) | 18.0 (9.0–28.0)‡ |
| Baseline CT ASPECT score |  |  |  |
| Mean (SD) | 9.2 (1.5) |  |  |
| Median (IQR) | 10.0 (9–10) |  |  |
| Prestroke mRS, n (%) | 217.0 (100.0) | 88.0 (100.0) | 56.0 (96.0) |
| 0–2 | 177.0 (78.0) | 67 (76.0) | NA |
| 0 | 49.0 (21.6) | 21 (24.0) | NA |
| 1 | 1.0 (0.4) | 0 | NA |
| 2 | 0 | 0 | 2.0 (4.0) |
| >2 |  |  |  |
| Body mass index, median (IQR) | 27.4 (24.1–31.1) | 30 (25.7–33.5) | 29.3 (6.8)* |
| Medical history, n (%) |  |  |  |
| Hypertension | 155.0 (68.3) | 67.0 (76.0) | 42.0 (72.0) |
| Diabetes mellitus | 45.0 (19.8) | 33.0 (38.0) | 14.0 (24.0) |
| Atrial fibrillation | 90.0 (39.6) | 42.0 (48.0) | 26.0 (45.0) |
| Dyslipidemia | 98.0 (43.2) | 55.0 (63.0) | 31.0 (53.0) |
| Smoking | 56.0 (24.7) | 37.0 (42.0) | 21.0 (36.0) |
| Previous MI/CAD | 45.0 (19.8) | 29.0 (33.0) | 19.0 (33.0) |
| Neurological history, n (%) |  |  |  |
| Previous ischemic stroke/transient ischemic attack | 43.0 (18.9) | 25.0 (28.0) | 12.0 (20.0) |
| Intravenous tPA failure | 120.0 (52.9) | 52.0 (58.0) | 19.0 (33.0) |
| Balloon guide catheter use | 167.0 (73.6) |  |  |
| Intermediate catheter use | 93.0 (41.0) |  |  |
| Proximal occlusion location, n (%) |  |  |  |
| Internal carotid artery | 35.0 (15.4) | 14.0 (16.0) | 12.0 (21.0) |
| M1 middle cerebral artery | 126.0 (55.5) | 53.0 (60.0) | 38.0 (66.0) |
| M2 middle cerebral artery | 57.0 (25.1) | 14.0 (16.0) | 6.0 (10.0) |
| Posterior circulation | 9.0 (4.0) | 7.0 (8.0) | 1.0 (2.0) |
| Occlusion side (left) | 103.0 (45.4) | 43.0 (53.0) | 27.0 (47.0) |
| Symptom onset or LKW to arterial puncture, min; median (IQR) | 214.0 (155.0–266.0) | 282.0 (210.0–342.0) | 293.5 (85.6) |

*Body mass index is reported as mean (SD) for SWIFT.
†One protocol violation in the treated subject with NIHSS <8.
‡SWIFT NIHSS reported as median (range).

Fig. 13

| | |
|---|---|
| Primary efficacy end point, n=227 | |
| Successful reperfusion (mTICI ≥2b within 3 passes without rescue),† n (%) | 182.0 (80.2) |
| Angiographic outcomes within 3 passes, n=227 | |
| Substantial reperfusion (mTICI ≥2c within 3 passes without rescue),† n (%) | 147.0 (64.8) |
| 0 | 24.0 (10.6) |
| 1 | 6.0 (2.6) |
| 2a | 12.0 (5.3) |
| 2b | 35.0 (15.4) |
| 2c | 48.0 (21.1) |
| 3 | 99.0 (43.6) |
| Other angiographic and procedural outcomes, n=227 | |
| Final successful reperfusion (mTICI ≥2b)‡ | 210.0 (92.5) |
| Final successful reperfusion (mTICI ≥2c), n (%) | 172.0 (75.8) |
| 0 | 7.0 (3.1) |
| 1 | 3.0 (1.3) |
| 2a | 7.0 (3.1) |
| 2b | 38.0 (16.7) |
| 2c | 54.0 (23.8) |
| 3 | 118.0 (52.0) |
| First-pass effect (mTICI), n=227 | |
| ≥2b§ | 117.0 (51.5) |
| ≥2c§ | 91.0 (40.1) |
| Use of rescue therapy | 44.0 (19.4) |
| Embolization into new territory | 15.0 (6.6) |
| Procedure time, median (IQR) | 35.0 (24.0–58.0) |
| Time to treat, median (IQR) | 24.0 (13.0–45.0) |
| 90-d good outcome (mRS, 0–2), n (%) | 146/217 (at least approximately 67) |

\* Three patients were treated with rescue therapy before the clot retrieval device made three passes and were counted as failures.
† No missing angiographic data.
‡ Final successful reperfusion was mTICI score of ≥2b in the target vessel on final angiogram.
§ First-pass effect is defined as achieving n mTICI score of ≥2c and mofified FPE as ≥2b on the first pass of the clot retrieval device, 1 of 3 rescue cases treated with the clot retrieval device and pump used aspiration and was counted as success

Fig. 14

|  | Treated (n=227) |
|---|---|
| Primary safety composite end point, n (%) | |
|    Symptomatic intracranial hemorrhage within 24 h or serious adverse device events* | 12/227 (5.3) |
| Secondary safety outcomes, n (%) | |
|    Symptomatic intracranial hemorrhage within 24 h | 12/227 (5.3) |
|    All-cause mortality rate at 90 d | 20/222 (9.0)† |
|    Procedure-related mortality (day 7 post-procedure) | 0 (0) |
|    Neurological deterioration (24 h post-procedure) | 8/178 (4.5)† |
|    Procedure-related serious adverse events | 11/227 (4.8) |
|    Serious adverse device events | 0 (0) |

\* Unknown or missing data are excluded from the demonitator
†The denominator included those with available data, for mortality, 5 patients completely lost for follow-up, and for neurological deterioration, it was only documented in 178 patients

Fig. 15

delivering a clot retrieval device to a blood vessel of the patient for retrieving a clot
310
restoring perfusion to the blood vessel by passing the clot retrieval device by, though, or about the clot and then removing the clot retrieval device to achieve at least a 90 % final revascularization rate (mTICI of 2b-3)
320
Fig. 22

400 

```
┌─────────────────────────────────────────────┐
│ delivering a clot retrieval device to a blood vessel of the │
│                    patient                  │
│                     410                     │
└─────────────────────────────────────────────┘
```

```
┌─────────────────────────────────────────────┐
│ restoring perfusion to the blood vessel by passing the │
│ clot retrieval device by, through, or about a clot of the │
│ blood vessel and then removing the clot retrieval device │
│    with a clinically effective outcome of at least │
│ approximately 67% where the patient has an mRS of 0- │
│                      2.                     │
│                     420                     │
└─────────────────────────────────────────────┘
```

Fig. 23

500 

```
┌─────────────────────────────────────────────┐
│ administering a clot retrieval device to a  │
│ blood vessel of the patient for retrieving  │
│ the clot                                    │
│                     510                     │
└─────────────────────────────────────────────┘
```

```
┌─────────────────────────────────────────────┐
│ restoring perfusion to the blood vessel to  │
│ achieve at least a 50 % final               │
│ revascularization rate (mTICI of 3) after   │
│ one or more passes of the clot retrieval    │
│ device by, through, or about the clot and   │
│ then removing the clot retrieval device     │
│                     520                     │
└─────────────────────────────────────────────┘
```

Fig. 24

delivering a clot retrieval device to a blood vessel of the patient for retrieving a clot
610
restoring perfusion to the blood vessel after two passes of the clot retrieval device by, though, or about the clot and then removing the clot retrieval device to achieve at least a 69 % final revascularization rate (mTICI of 2b-3)
620
<u>Fig. 25</u>

700 delivering a clot retrieval device to a blood vessel of the patient for retrieving a clot
710 restoring perfusion to the blood vessel by passing the clot retrieval device by, though, or about the clot and retracting the clot retrieval device to achieve
- at least a 90 % final revascularization rate (mTICI of 2b-3);
- a clinically effective outcome of at least approximately 67%, the clinically effective outcome being an mRS of 0-2; and/or
- at least a 50 % final revascularization rate (mTICI of 3) after one or more passes of the clot retrieval device by, through, or about the clot
720

Fig. 26

| Primary Efficacy Endpoint | FDA ITT Cohort (N=191) |
|---|---|
| Successful Revascularization[1] | 72% (137[b]/191) |
| [95% Conf. Interval][2] | [65%, 78%] |
| p-value | <0.0001[a] |
| Primary Safety Endpoint | |
| Occurrence of sICH within 24h and/or SADE | 5% (9[c]/191) |
| [Unadjusted 95% Conf. Interval*] | [2%, 9%] |
| Key Secondary Endpoints | |
| Good clinical outcome[3] | 55% (102[b]/187[d]) |
| [Unadjusted 95% Conf. Interval*] | [47%, 62%] |
| Procedure-related mortality at 7 days post-procedure | 0% (0/191) |
| [Unadjusted 95% Conf. Interval*] | [0%, 2%] |
| All-cause mortality at 90 days post-procedure | 9% (16/186[d]) |
| [Unadjusted 95% Conf. Interval*] | [5%, 14%] |
| Neurological deterioration[4] | 5% (10/183[d]) |
| [Unadjusted 95% Conf. Interval*] | [3%, 10%] |
| Procedure Related Serious Adverse Events (PRSAE) | 5% (9/191) |
| [Unadjusted 95% Conf. Interval*] | [2%, 9%] |

1. Successful revascularization was defined as achieving an mTICI rating of 2b or greater, in 3 or less passes.
2. All confidence intervals reported for binary variables are Clopper-Pearson Exact binomial confidence intervals, and those for continuous variables are based on a normal distribution assumption for the parameter of interest
3. Modified Rankin Scale score of ≤2 at 90 days post-procedure
4. Increase of ≥4 points on the NIHSS score at 24 hours post-procedure.

*The confidence intervals are calculated without multiplicity adjustment. As such, the confidence intervals are provided to show the variability only and should not be used to draw any statistical inferences.* a. One-sided Exact test at the two-sided 5% significance level for the revascularization rate against a performance goal of 56%;
    b. Use of rescue therapy at any point in the procedure was imputed as a failure to achieve the endpoint
    c. No occurrence of SADE;
    d. Unknown/Missing data excluded.

Fig. 27

| Population: FDA ITT Cohort (N=191) Primary Efficacy Endpoint | US cohort (N=94) | EU cohort (N=97) |
|---|---|---|
| Successful Revascularization[1,2] | 67% (63/94) | 76% (74/97) |
| [95% Conf. Interval][3] | [57%, 76%] | [67%, 84%] |

1. Successful revascularization was defined as achieving an mTICI rating of 2b or greater, in 3 or less passes of the study device.
2. Use of rescue therapy at any point in the procedure was imputed as a failure to achieve the endpoint;
3. All confidence intervals reported for binary variables are Clopper-Pearson Exact binomial confidence intervals, and those for continuous variables are based on a normal distribution assumption for the parameter of interest.

Fig. 28

| MedDRA Preferred Term | % pts w/ SAE [Number of SAE] FDA ITT Cohort (N=191) |
|---|---|
| Cardiac disorders | |
| Myocardial infarction | 1.57% [3] |
| Atrial fibrillation | 1.05% [2] |
| Cardiac failure | 1.05% [2] |
| Gastrointestinal disorders | |
| Gastrointestinal haemorrhage | 1.05% [2] |
| Infections and infestations | |
| Septic shock | 2.09% [4] |
| Urinary tract infection | 1.57% [3] |
| Pneumonia | 1.57% [3] |
| Sepsis | 1.05% [2] |
| Nervous system disorders | |
| Ischaemic stroke | 6.81% [13] |
| Haemorrhagic transformation stroke | 6.28% [12] |
| Brain oedema | 3.66% [7] |
| Neurological decompensation | 2.09% [4] |
| Seizure | 1.57% [3] |
| Subarachnoid haemorrhage | 1.57% [3] |
| Carotid artery stenosis | 1.05% [2] |
| Respiratory, thoracic and mediastinal disorders | |
| Pneumonia aspiration | 1.57% [3] |
| Respiratory distress | 1.05% [2] |
| Bronchospasm | 1.05% [2] |
| Respiratory failure | 1.05% [2] |
| Surgical and medical procedures | |
| Coronary arterial stent insertion | 1.05% [2] |
| Vascular disorders | |
| Vessel perforation | 1.05% [2] |
| Deep vein thrombosis | 1.05% [2] |

Fig. 29

| Angiographic reasons for exclusion from treatment | Number of Subjects (N=16)* |
|---|---|
| No angiographic confirmation of an occlusion of an ICA (including T or L occlusions), M1 or M2 MCA, VA, or BA with mTICI flow of 0 – 1. | 7 |
| The patient is indicated for neurothrombectomy treatment by the interventionalist and it is confirmed by diagnostic angiography that the device will not be able to reach the target lesion proximally. | 7 |
| Stenosis, or any occlusion, in a proximal vessel that requires treatment or prevents access to the site of occlusion. | 4 |
| Evidence of dissection in the extra or intracranial cerebral arteries. | 2 |
| Occlusions in multiple vascular territories (e.g., bilateral anterior circulation, or anterior/posterior circulation). | 2 |
| Other reasons for exclusion from treatment | Number of Subjects (N=1) |
| Severe agitation | 1 |

Fig. 30

| mRS | % Achieving mRS Level | | Cost/mRS Level | Cost/Patient | | |
|---|---|---|---|---|---|---|
| | FPE (n=91) | Not Achieving FPE (n=81) | | FPE | Not Achieving FPE | Difference |
| 0 | 41.38% | 19.48% | $11,466.92 | $14,531.19 | $18,407.35 | -$3,876.16 |
| 1 | 21.84% | 27.27% | $11,807.59 | | | |
| 2 | 17.24% | 14.29% | $13,659.62 | | | |
| 3 | 9.20% | 7.79% | $23,454.61 | | | |
| 4 | 2.30% | 11.69% | $47,472.32 | | | |
| 5 | 2.30% | 5.19% | $69,792.07 | | | |
| 6 | 5.75% | 14.29% | - | | | |

Fig. 31A

| Procedural healthcare resource | Cost/patient | | |
|---|---|---|---|
| | FPE (n=91) | Not Achieving FPE (n=81) | Difference |
| LOS* | | | |
| Days in ICU | $6,467.74 | $7,040.14 | -$572.40 |
| Standard bed days | $2,791.39 | $5,782.63 | -$2,991.25 |
| Devices/methods used | $7,886.35 | $10,677.66 | -$2,791.31 |
| Total | $17,145.48 | $23,500.43 | -$6,354.95 |

Fig. 31B

| Subsequent Passes | Number of Patients | Patients with Improved mTICI Score |
|---|---|---|
| Pass 1 to 2 | 123 | 52 (42.3%) |
| Pass 2 to 3 | 79 | 40 (50.6%) |
| Pass 3 to 4 | 35 | 20 (57.1%) |
| Pass 4 to 5 | 16 | 4 (25.0%) |
| Pass 5 to 6 | 14 | 5 (35.7%) |
| Pass 6 to 7 | 9 | 2 (22.2%) |
| Pass 7 to 8 | 4 | 3 (75.0%) |
| Pass 8 to 9 to 10 | 1 | 0 (0.0%) |

Fig. 36A

| Subsequent Passes | Patients mTICI 2c-3 | Patients with mTICI 2c-3 and 90 Day mRS 0-2 |
|---|---|---|
| Pass 1 | 80 | 64 (80.0%) |
| Pass 2 | 25 | 20 (80.0%) |
| Pass 3 | 31 | 17 (54.8%) |
| Pass 4 | 9 | 6 (66.7%) |
| Pass 5 | 3 | 1 (33.3%) |
| Pass 6 | 2 | 2 (100%) |
| Pass 7 | 0 | 0 |
| Pass 8 | 1 | 1 (100%) |
| Pass 9/10 | 0 | 0 |

Fig. 36B

SYSTEMS AND METHODS TO RESTORE PERFUSION TO A VESSEL

CROSS-REFERENCE TO RELATED APPLICATIONS

The present application is a continuation of U.S. application Ser. No. 17/749,433, filed May 20, 2022, which claims the benefit of priority of U.S. Provisional Application No. 63/190,892, filed May 20, 2021, which is also a continuation-in-part of U.S. application Ser. No. 16/569,637, filed Sep. 12, 2019, which claims the benefit of priority of U.S. Provisional Application Nos. 62/844,502, filed May 7, 2019, 62/822,467, filed Mar. 22, 2019, 62/792,741, filed Jan. 15, 2019, 62/772,006, filed Nov. 27, 2018, and 62/730,952, filed Sep. 13, 2018, and which is a continuation-in-part of U.S. application Ser. No. 14/985,729, filed Dec. 31, 2015, now U.S. Pat. No. 10,610,246, issued Apr. 7, 2020, which is a continuation of U.S. application Ser. No. 14/629,217, filed Feb. 23, 2015, now U.S. Pat. No. 9,445,829, issued Sep. 20, 2016, which is a continuation of International Application No. PCT/EP2014/054251, filed Mar. 5, 2014, which claims the benefit of priority of U.S. Provisional Application No. 61/785,213, filed Mar. 14, 2013. The present application is also a continuation-in-part of U.S. application Ser. No. 17/207,011, filed Mar. 19, 2021, which is a continuation of U.S. application Ser. No. 15/997,335 filed Jun. 4, 2018, now U.S. Pat. No. 10,952,760 issued Mar. 21, 2021, which is a continuation of U.S. application Ser. No. 14/986,357 filed Dec. 31, 2015, now U.S. Pat. No. 10,034,680 issued Jul. 31, 2018, which is a continuation of U.S. application Ser. No. 13/823,060, filed Mar. 13, 2013, now U.S. Pat. No. 9,301,769 issued Apr. 5, 2016, which is a National Stage Entry of PCT/IE2012/000011, filed Mar. 9, 2012, which claims priority to U.S. Provisional Application Nos. 61/450,810, filed Mar. 9, 2011 and 61/552,130, filed Oct. 27, 2011.

The contents of these applications are incorporated herein by reference in their entirety as if set forth verbatim.

FIELD

This disclosure relates to devices and methods of removing acute blockages from blood vessels.

BACKGROUND

The World Health Organization estimates that 15,000,000 blood clots occur annually. Clots may develop and block vessels locally without being released in the form of an embolus—this mechanism is common in the formation of coronary blockages. Acute obstructions may include blood clots, misplaced devices, migrated devices, large emboli and the like. Thromboembolism occurs when part or all of a thrombus breaks away from the blood vessel wall. This clot is then carried in the direction of blood flow. The large vessels of the brain include the Internal Carotid Artery (ICA), Middle Cerebral Artery (MCA), Vertebral Artery (VA), and the Basilar Artery (BA). Clots can include a range of morphologies and consistencies. Long strands of softer clot material may tend to lodge at bifurcations or trifurcations, resulting in multiple vessels being simultaneously occluded over significant lengths. Older clot material can also be less compressible than softer fresher clots, and under the action of blood pressure it may distend the compliant vessel in which it is lodged. Clots also may vary greatly in length, even in any one given area of the anatomy. For example, clots occluding the middle cerebral artery of an ischemic stroke patient may range from just a few millimeters to several centimeters in length.

Of the 15,000,000 clots that occur annually, one-third of patients die and another one-third are disabled. Two of the primary factors associated with mortality in these patients are the occlusion location and the time to treatment. Large-vessel occlusions present in 46% of unselected acute stroke patients presenting in academic medical centers, are associated with higher stroke severity. These more proximal vessels feed a large volume of brain tissue, ergo clinicians use the presenting NIHSS (National Institute of Health Stroke Scale) score as an indicator of large-vessel occlusion.

With this, it is understood that an ischemic stroke may result if the clot lodges in the cerebral vasculature. It is estimated that 87% of stroke cases are acute ischemic stroke (AIS). In the United States alone, roughly 700,000 AIS cases occur every year and this number is expected to increase with an ageing population. Occlusion of these large arteries in ischemic stroke is associated with significant disability and mortality. Revascularization of intracranial artery occlusions is the therapeutic goal in stroke therapy. Endovascular mechanical revascularization (thrombectomy) is an increasingly used method for intracranial large vessel recanalization in acute stroke. Currently, a number of mechanical recanalization devices are in clinical use. First generation devices included the Merci Retriever device. Newer devices based on stent-like technology, referred to as "stentrievers" or "stent-retrievers", are currently displacing these first generation thrombectomy devices for recanalization in acute ischemic stroke.

There are significant challenges associated with designing clot removal devices that can deliver high levels of performance. There are also a number of access challenges that make it difficult to deliver devices. For example, the vasculature in the area in which the clot may be lodged is often fragile and delicate and neurovascular vessels are more fragile than similarly sized vessels in other parts of the body and are in a soft tissue bed. Excessive tensile forces applied on these vessels could result in perforations and hemorrhage. Pulmonary vessels are larger than those of the cerebral vasculature, but are also delicate in nature, particularly those more distal vessels.

Stent-like clot retriever devices are being increasingly used to remove clots from cerebral vessels of acute stroke patients but such devices are not without disadvantages. A stent-like clot retriever relies on its outward radial force to grip the clot. If the radial force is too low, the device will lose its grip on the clot. If the radial force is too high, the device may damage the vessel wall and may require too much force to withdraw. Such devices that have sufficient radial force to deal with all clot types may therefore cause vessel trauma and serious patient injury, and retrievers that have appropriate radial force to remain atraumatic may not be able to effectively handle all clot types. In this respect, retriever devices may differ in size, shape, and physical properties, such as radial force, as discussed above, ease of deployment, friction, radiopacity and interaction with vessel wall. See, Loh Y, Jahan R, McArthur D. *Recanalization rates decrease with increasing thrombectomy attempts.* American Journal of Neuroradiology. 2010 May; 31(5):935-9; and Arai D, Ishii A, Chihara H, Ikeda H, Miyamoto S. *Histological examination of vascular damage caused by stent retriever thrombectomy devices*, J Neurointerv Surg. 2016 October; 8(10):992-5. Some designs have also been based on in-vitro stroke models that incorporate realistic clot analogs derived from animal blood that represent the wide range of human clots retrieved from stroke patients. See, Eugène F, Gauvrit J Y, Ferré J C, Gentric J C, Besseghir A, Ronzière T, et al. *One-year MR angiographic and clinical follow-up after intracranial mechanical thrombectomy using a stent retriever device*, AJNR Am J Neuroradiol. 2015 January; 36(1):126-32 (18), each of which are incorporated by reference herein in their entirety.

Currently, intravenous (IV) lytics are used for patients presenting up to 4.5 hours after symptom onset. Current guidelines recommend administering IV lytics in the 3-4.5 hour window to those patients who meet the ECASS 3 (European Cooperative Acute Stroke Study 3) trial inclusion/exclusion criteria. Since a large percentage of strokes presenting at hospitals are large vessel occlusions, this is an important clinical challenge to address. Additionally, not all patients may be treated with thrombolytic therapy, and so mechanical thrombectomy is a valuable alternative in patients contraindicated to t-PA (tissue plasminogen activator) or where t-PA treatment was not effective.

Further, acute stroke treatment protocols vary by hospital center. Often, CT is used to exclude hemorrhagic stroke, and CT Angiography is used. Additional imaging assessment, such as MRI or CT Perfusion, varies by center. Recent AIS trials have demonstrated the clinical benefit and reperfusion efficacy of endovascular therapy using stent-retriever devices. See, Zaidat O O, Castonguay A C, Gupta R, Sun C J, Martin C, Holloway W E, et al. *The first pass effect: a new measure for stroke thrombectomy devices*. Stroke. 2018; 49; 660-666; Chueh J Y, Marosfoi M G, Brooks O W, King R M, Puri A S, Gounis M J. *Novel distal emboli protection technology: the EmboTrap*. Interv Neurol. 2017; 6:268-276. doi: 10.1159/000480668; Nogueira R G, Lutsept H L, Gupta R, Jovin T G, Albers G W, Walker G A, Liebeskind D S, Smith W S, *TREVO 2 Trialists. Trevo versus Merci retrievers for thrombectomy revascularisation of large vessel occlusions in acute ischaemic stroke (TREVO 2): a randomised trial*. Lancet. 2012; 380:1231-1240. doi: 10.1016/S0140-6736(12)61299-9. There are several FDA approved stent retriever devices indicated for neuro-thrombectomy, including Merci®, Trevo®, and Solitaire®. These devices are generally described in U.S. Pat. Nos. 8,066,757; 8,088,140; 8,945,172; 9,320,532; 8,585,713; 8,945,143; 8,197,493; 8,940,003; 9,161,766; 8,679,142; 8,070,791; 8,574,262; 9,387,098; 9,072,537; 9,044,263; 8,795,317; 8,795,345; 8,529,596; and 8,357,179. The results of these trials provide a valid scientific basis for the establishment of a composite performance goal derived using a Bayesian meta-analysis. Presently, these devices are now considered the standard of care for treatment of AIS secondary to large-vessel occlusion. See, Powers W J, Derdeyn C P, Biller J, Coffey C S, Hoh B L, Jauch E C, et al; *American Heart Association Stroke Council*. 2015 *American Heart Association/American Stroke Association focused update of the 2013 guidelines for the early management of patients with acute ischemic stroke regarding endovascular treatment: a guideline for healthcare professionals from the American Heart Association/American Stroke Association*. Stroke. 2015; 46:3020-3035. doi: 10.1161/STR.0000000000000074

In a pooled, individual participant data meta-analyses of these trials, the rate of successful reperfusion (mTICI≥2b) was 71%, whereas the rate of final complete reperfusion (mTICI=3) was only 33%. The modified treatment in cerebral ischemia (mTICI) score categorizes the amount of flow restoration after endovascular revascularization. Specifically, the mTICI score was developed from the original Thrombolysis in Cerebral Infarction (TICI) scale by a consensus group in 2013. The recommendations included a name change to better reflect the increasing use of endovascular therapy for stroke, and simplification of the TICI 2 component to less than half of the target vascular territory (mTICI 2a) or more than half (mTICI 2b). Classification: Grade 0: no perfusion; Grade 1: antegrade reperfusion past the initial occlusion, but limited distal branch filling with little or slow distal reperfusion; Grade 2; Grade 2a: antegrade reperfusion of less than half of the occluded target artery previously ischemic territory (e.g. in one major division of the middle cerebral artery (MCA) and its territory); Grade 2b: antegrade reperfusion of more than half of the previously occluded target artery ischemic territory (e.g. in two major divisions of the MCA and their territories); Grade 3: complete antegrade reperfusion of the previously occluded target artery ischemic territory, with absence of visualized occlusion in all distal branches.

It is understood that mention of percentages in this disclosure refer to averages, unless otherwise specified. In other words, there was a 30% rate of failed reperfusion and only one third of patients achieving final complete reperfusion after all interventions. There was also a limited rate of final near complete or complete (mTICI≥2c) with reported rates up to 50%. The first past attempts for each device for near complete or complete reperfusion was also still relatively low only being up to 30%. Opportunities also exist to increase the rate of near-complete reperfusion (mTICI≥2c) from a single pass of a device which to improve patient outcomes. For example, for these earlier devices 90-day functional independence rates of 61.3% versus 35.3% in non-FP success have been observed.

In view of these clear performance disadvantages, further reperfusion and patient outcomes advances in AIS treatment are warranted. The solution of this disclosure resolves these and other issues of the art.

SUMMARY

The subject of this disclosure is the use of a clot retrieval device to treat ischemic stroke for restoring perfusion and/or removing a clot and other obstructions from the neurovascular arteries and veins as well as other vascular beds.

An example of treating an ischemic stroke can include delivering and passing at least one clot retrieval device at least one time through an occluded blood vessel to achieve a clinically effective revascularization rate.

One example can be a method of treating an occluded blood vessel in a human by restoring a clinically effective perfusion rate to the tissue distal of the occluded blood vessel by passing at least one clot retrieval device at least one time through the occluded blood vessel.

In some examples, a method of treating ischemic stroke is disclosed. The method can include delivering a clot retrieval device to a blood vessel of the patient for retrieving a clot; and restoring perfusion to the blood vessel by passing the clot retrieval device by, through, or about the clot and then removing the clot retrieval device to achieve at least a 90% final revascularization rate mTICI≥2b.

In some examples, a method of treating ischemic stroke is disclosed. The method can include delivering a clot retrieval device to a blood vessel of the patient; and restoring perfusion to the blood vessel by passing the clot retrieval device by, through, or about a clot of the blood vessel and then removing the clot retrieval device with a clinically effective outcome of at least approximately 67%, the clinically effective outcome being a modified Rankin Scale [mRS] of 0-2. In some examples, the clinically effective outcome is 60% or greater, 65% or greater, or 70% or greater.

In some examples, the clinically effective outcome is measured at 90-days following restoration of perfusion to the vessel.

In some examples, a method of treating ischemic stroke is disclosed. The method can include administering a clot retrieval device to a blood vessel of the patient for retrieving the clot; and restoring perfusion to the blood vessel to achieve at least a 50% final revascularization rate mTICI=3 after one or more passes of the clot retrieval device by, through, or about the clot.

In some examples, a method of treating ischemic stroke is disclosed. The method includes delivering a clot retrieval device to a blood vessel of the patient for retrieving a clot; and restoring perfusion to the blood vessel after two passes of the clot retrieval device by, through, or about the clot to achieve at least a 69% revascularization rate mTICI≥2b.

In some examples, a device for treating ischemic stroke is disclosed. The device can include a first stent partially inside a second stent, each stent comprising a proximal end and a distal end. The first and the second stents may only be connected at their proximal and distal ends. The clot retrieval device can be capable of being delivered to a blood vessel and restoring perfusion to the blood vessel by passing the clot retrieval device by, through, or about the clot to achieve at least a 90% final revascularization rate mTICI≥2b; a clinically effective outcome of at least approximately 67% wherein the clinically effective outcome is an mRS of 0-2; or to achieve at least a 50% final revascularization rate mTICI=3 after three passes of the clot retrieval device by, through, or about the clot.

In some examples, a device for restoring perfusion to a blood vessel is disclosed. The device can include a collapsed delivery configuration and an expanded deployed configuration. The device can also include a framework of struts forming a porous outer body radially surrounding a porous inner body during both the collapsed delivery configuration and the expanded deployed configuration, the outer body being expandable to a radial extent to define a clot reception space. A distal end of the inner body can be located within the outer body and adjacent a distal end of the outer body and extending in the deployed configuration towards the outer body to a greater extent than the inner body. The clot retrieval device is capable of being delivered to a blood vessel and restoring perfusion to the blood vessel by passing the clot retrieval device by, through, or about the clot to achieve at least a 90% final revascularization rate mTICI≥2b; a clinically effective outcome of at least approximately 67%, wherein the clinically effective outcome is defined as an mRS of 0-2; or to achieve at least a 50% final revascularization rate mTICI=3 after three passes of the clot retrieval device by, through, or about the clot.

In some examples, the device and/or method can achieve at least a 93% final revascularization rate mTICI≥2b in the blood vessel by passing the clot retriever device by, through, or about the clot one or more times and retracting proximally the clot retriever device.

In some examples, a population size for the final revascularization rate is at least 150 patients.

In some examples, a population size for the final revascularization rate is at least 80 patients.

In some examples, the clinically effective outcome being an mRS≤1, the device and/or method can achieve at least a 50% final revascularization rate mTICI=3 in the blood vessel after three passes of the clot retrieval device by, through, or about the clot and retracting proximally the clot retriever device.

In some examples, the clinically effective outcome being an mRS≤1, the device and/or method can achieve at least a 51.5% final revascularization rate mTICI=3 in the blood vessel after three passes of the clot retrieval device by, through, or about the clot and retracting proximally the clot retriever device.

In some examples, the clinically effective outcome being an mRS≤2, the device and/or method can achieve at least a 60% revascularization rate mTICI≥2b in the blood vessel after three passes of the clot retrieval device by, through, or about the clot and retracting proximally the clot retriever device.

In some examples, the device and/or method can achieve at least a 60% revascularization rate mTICI≥2c in the blood vessel by passing the clot retriever device by, through, or about the clot one or more times and retracting proximally the clot retriever device.

In some examples, the device and/or method can achieve at least a 65% revascularization rate mTICI≥2c in the blood vessel by passing the clot retriever device by, through, or about the clot one or more times and retracting proximally the clot retriever device.

In some examples, the device and/or method can achieve at least a 50% revascularization rate mTICI≥2b in the blood vessel after one pass of the clot retrieval device by, through, or about the clot and retracting proximally the clot retriever device.

In some examples, the device and/or method can achieve at least a 51.5% revascularization rate mTICI≥2b after one pass of the clot retrieval device by, through, or about the clot and removing the clot retriever device.

In some examples, the device and/or method can achieve at least a 10% revascularization rate mTICI≥2b in the blood vessel after one pass of the clot retrieval device by, through, or about the clot and removing the clot retriever device.

In some examples, the device and/or method can achieve at least a 30% revascularization rate mTICI≥2b in the blood vessel after one pass of the clot retrieval device by, through, or about the clot and removing the clot retriever device.

In some examples, the device and/or method can achieve at least an 80% revascularization rate mTICI≥2b after three passes of the clot retrieval device by, through, or about the clot and removing the clot retriever device.

In some examples, the device and/or method can achieve at least a 75% final revascularization rate mTICI≥2c in the blood vessel after procedure completion with the clot retrieval device by, through, or about the clot and removing the clot retriever device.

In some examples, the device and/or method can achieve at least a 90% final revascularization rate mTICI≥2b in the blood vessel after procedure completion with the clot retrieval device by, through, or about the clot and removing the clot retriever device.

In some examples, the device and/or method can achieve at least a 92.5% final revascularization rate mTICI≥2b in the blood vessel after procedure completion with the clot retrieval device by, through, or about the clot and removing the clot retriever device.

In some examples, the device and/or method can achieve at least a 43% revascularization rate mTICI=3 in the blood vessel after three passes of the clot retrieval device by, through, or about the clot and removing the clot retriever device.

In some examples, the device and/or method can achieve at least a 50% revascularization rate mTICI=3 in the blood vessel by passing the clot retriever device by, through, or about the clot one or more times and removing the clot retriever device.

In some examples, the device and/or method can achieve at least a 52% revascularization rate mTICI=3 in the blood vessel by passing the clot retriever device by, through, or about the clot one or more times and removing the clot retriever device.

In some examples, the method can include determining whether inclusion criteria for the patient consists of pre-stroke modified Rankin Scale (mRS) ≤2; baseline National Institutes of Health stroke scale (NIHSS) score ≥8 and ≤25; Alberta Stroke Program early computed tomography (AS-PECT) score ≥6; core infarct volume ≤50 mL on magnetic resonance imaging or computed tomography based imaging (for anterior circulation strokes); and treatment with intravenous tissue-type plasminogen activator (tPA); if yes, administering the clot retrieval device to the blood vessel of the patient.

In some examples, inclusion criteria for the patient consists of—prestroke modified Rankin Scale (mRS) ≤2; baseline National Institutes of Health stroke scale (NIHSS) score ≥8 and ≤25; Alberta Stroke Program early computed tomography (ASPECT) score ≥6; core infarct volume <50 mL on magnetic resonance imaging or computed tomography based imaging (for anterior circulation strokes); and treatment with intravenous tissue-type plasminogen activator (tPA).

In some examples, the patient is within 8 hours of stroke onset when the device is used or method performed.

In some examples, the patient is within 12 hours of stroke onset when the device is used or method performed.

In some examples, the patient is within 24 hours of stroke onset when the device is used or method performed.

In some examples, the patient is within 3 hours of stroke onset when the device is used or method performed.

In some examples, the clot retrieval device is delivered through the femoral artery of the patient.

In some examples, wherein the age of the patient is at least 68.

In some examples, the risk factor of the patient is the NIHSS is at least 15.8.

In some examples, the group of risk factors further consists of hypertension, diabetes mellitus, atrial fibrillation, a previous stroke, a previous MI, a dyslipidaemia, smoking, a Stability and Workload Index for Transfer (SWIFT) score, The postoperative venous thromboembolism (TREVO) score.

In some examples, the method can include imaging the patient; determining whether the patient exhibits at least one risk factor of this disclosure; administering the clot retrieval device to the blood vessel; and retrieving the clot.

In some examples, a method of treating ischemic stroke is disclosed. The method can include delivering a clot retrieval device to a blood vessel of the patient for retrieving a clot; and restoring perfusion to the blood vessel by passing the clot retrieval device by, through, or about the clot and removing the clot retrieval device to achieve reduced healthcare costs.

In some examples, a method of treating ischemic stroke is disclosed. The method can include administering a clinically effective clot retrieval device to a blood vessel of the patient for retrieving the clot; and restoring perfusion to the blood vessel to achieve reduced healthcare costs.

In some examples, a clinically effective clot retrieval device for treating ischemic stroke is disclosed. The device can be capable of delivery to a blood vessel and restoring perfusion to the blood vessel by passing the clot retrieval device by, through, or about the clot and then removing to achieve reduced healthcare costs.

In some examples, a method of treating ischemic stroke is disclosed. The method can include delivering and passing at least one clot retrieval device at least one time through an occluded blood vessel to achieve reduced healthcare costs.

In some examples, a method of treating ischemic stroke is disclosed. The method can include determining inclusion criteria for a patient including: a prestroke modified Rankin Scale (mRS) ≤2; a baseline National Institutes of Health stroke scale (NIHSS) score ≥8 and ≤25; an Alberta Stroke Program early computed tomography (ASPECT) score ≥6; a core infarct volume <50 mL on magnetic resonance imaging or computed tomography-based imaging (for anterior circulation strokes); and a treatment with intravenous tissue-type plasminogen activator (tPA); if yes, passing a clinically effective clot retriever device of any preceding claim by, through, or about the clot one or more times and retracting proximally the clot retriever device to achieve reduced healthcare costs.

In some examples, method of treating an ischemic stroke is disclosed by delivering and passing at least one clot retrieval device at least one time through an occluded blood vessel; and achieving similar revascularization rates regardless of a patient time of admission to a patient time to groin puncture.

In some examples, a system for restoring perfusion to a blood vessel having an occlusion is disclosed. The system can include a reperfusion device comprising a collapsed delivery configuration and an expanded deployed configuration. The system can include an aspiration system in communication with the reperfusion device. The system can include a delivery system configured to deliver the reperfusion device to the occlusion and in communication with the aspiration system. The reperfusion device can be capable of being delivered to the blood vessel and restoring perfusion by passing the reperfusion device by, through, or about the clot and then proximally retracting the device to achieve at least one of at least a 90% final revascularization rate mTICI≥2b; a clinically effective outcome of at least approximately 67% (mRS of 0-2); and/or at least a 50% final revascularization rate mTICI=3 after three passes of the reperfusion device by, through, or about the clot. The aspiration system can be configured to restore perfusion to the blood vessel through a microcatheter of the delivery system.

In some examples, the clot retrieval device can have a collapsed delivery configuration and an expanded deployed configuration. The device can include a framework of struts forming a porous inner body flow channel and having a tubular main body portion and a closed distal portion and/or closed distal end; and a framework of struts forming an outer tubular body radially surrounding the tubular main body portion of the inner body during both the collapsed delivery configuration and the expanded deployed configuration.

In some examples, the device can include an inner tubular body having a plurality of openings, a collapsed delivery configuration, and an expanded deployed configuration; and an outer tubular body at least partially overlying the inner tubular body and having a plurality of closed cell.

In some examples, the clot retrieval device can have a shaft extending between a proximal end and a distal end; a self-expandable outer body coupled to the shaft, the expandable outer body comprising a plurality of longitudinally spaced clot scaffolding segments separated by voids forming a plurality of clot inlet mouths between the adjacent clot scaffolding segments, wherein each clot scaffolding segment includes a plurality of closed cells; and an inner expandable body including a plurality of struts. The outer expandable body may at least partially overlay the inner expandable body and being expandable to a radial extent which is greater than the radial extent of the inner expandable body in the deployed configuration to provide a clot reception space radially between the inner expandable body and the outer expandable body. The clot is located in one of the following locations: a carotid artery, a M1 middle cerebral artery, a M2 middle cerebral artery, a basilar artery, a vertebral artery, a balloon guide catheter.

In some examples, the clot retriever device is delivered to the clot using an intermediate catheter.

In some examples, the device and/or method can deliver the clot retrieval device through the blood vessel making between one and three passes by, through, or about the clot to achieve a modified treatment in cerebral infarction (mTICI) score of ≥2b.

In some examples, the device and/or method can be administered with rescue therapy after a third pass if the mTICI score is less than 2b. The rescue therapy can be another mechanical thrombectomy device; mechanical pump aspiration; intracranial stenting; or initiation of intra-arterial tPA during the procedure.

In some examples, the patient does not have stenosis in the vessel.

In some examples, the patient does not have any occlusion in a proximal vessel preventing access to the clot.

In some examples, the mTICI classification comprises Grade 0: in which there is no perfusion; Grade 1: in which there is antegrade reperfusion past the initial occlusion, but limited distal branch filling with little or slow distal reperfusion; Grade 2: in which there is incomplete antegrade reperfusion wherein the contrast passes the occlusion and opacifies the distal arterial bed but there are residual antegrade perfusion deficits; Grade 2a: in which there is antegrade reperfusion of less than half of the occluded target artery previously ischemic territory (e.g. in one major division of the middle cerebral artery (MCA) and its territory); Grade 2b: in which there is antegrade reperfusion of more than half of the previously occluded target artery ischemic territory (e.g. in two major divisions of the MCA and their territories); Grade 2c: in which there is antegrade reperfusion of greater than 90% but less than TICI 3 or near complete reperfusion Grade 3: in which there is complete antegrade reperfusion of the previously occluded target artery ischemic territory, with absence of visualized occlusion in all distal branches.

In some examples, the clot retrieval device is capable of being delivered to a blood vessel and restoring perfusion to the blood vessel by passing the clot retrieval device by, through, or about the clot to achieve at least a final revascularization rate mTICI≥2c in the blood vessel after three passes of the clot retrieval device by, through, or about the clot that is approximately a 5% improvement from the closest comparable clinical data.

In some examples, the clot retrieval device is capable of being delivered to a blood vessel and restoring perfusion to the blood vessel by passing the clot retrieval device by, through, or about the clot to achieve a final complete revascularization rate mTICI=3 in the blood vessel after three passes of the clot retrieval device by, through, or about the clot that is approximately a 10% improvement from the closest comparable clinical data.

In some embodiments of the herein disclosed methods, the step of restoring perfusion to the blood vessel is caused by withdrawing some or all of the clot after passing the clot retrieval device by, through, or about the clot.

In some embodiments of the herein disclosed methods, the step of restoring perfusion to the blood vessel is caused by retracting the clot retrieval device after the clot has embedded with the clot retrieval device.

In some embodiments of the herein disclosed methods, a pass of the clot retrieval device comprises: positioning the clot retrieval device distal of the clot; and retracting proximally the clot retrieval device to a distal end of a microcatheter.

In some examples, the clot is disposed in the internal carotid artery.

In some examples, the clot is disposed in the M1 segment of the middle cerebral artery.

In some examples, the clot is disposed in the M2 segment of the middle cerebral artery.

In some examples, the clot is disposed in the vertebral artery.

In some examples, the clot is disposed in the basilar arteries.

In some examples, the method can include embedding the clot retrieval device with the clot for one minute or less and retracting the clot retrieval device.

In some examples, method can include embedding the clot retrieval device with the clot for two minutes or less and retracting the clot retrieval device.

In some examples, method can include embedding the clot retrieval device with the clot for three minutes or less and retracting the clot retrieval device.

In some examples, method can include embedding the clot retrieval device with the clot for four minutes or less and retracting the clot retrieval device.

In some examples, the method can include passing the clot retrieval device two (2) or fewer passes by, through, or about the clot and retracting the clot retrieval device; and restoring perfusion in 54 minutes or less time from initial delivery of the clot retrieval device.

In some examples, the method can include advancing the clot retrieval device so that a distal end of a microcatheter is positioned distal of the occlusion and then passing the clot retrieval device by, through, or about the clot and retracting the clot retrieval device.

In some examples, the clot retrieval device is clinically effective.

In some examples, a method of treating ischemic stroke is disclosed. The method can include delivering a clinically effective clot retrieval device to a blood vessel of the patient for retrieving a clot; and restoring perfusion to the blood vessel by passing the clot retrieval device by, through, or about the clot and removing the clot retrieval device to achieve at least a 90% final clinically effective revascularization rate under the modified treatment in cerebral infarction score of equal to or greater than a grade of 2b mTICI≥2b; and/or at least a 50% final revascularization rate mTICI=3 after one or more passes of the clinically effective clot retrieval device by, through, or about the clot; and/or at least a 69% clinically effective revascularization rate mTICI≥2b after two passes of the clinically effective clot retrieval device by, through, or about the clot.

In some examples, a clinically effective clot retrieval device for treating ischemic stroke is disclosed, the device, the clinically effective clot retrieval device being capable delivery to a blood vessel and restoring perfusion to the blood vessel by passing the clot retrieval device by, through, or about the clot and then removing to achieve at least one of at least a 90% final revascularization rate mTICI≥2b; a clinically effective outcome of at least approximately 67%, the clinically effective outcome being mRS of 0-2; and at least a 75% final revascularization rate mTICI=3 after procedure completion using the clinically effective clot retrieval device with the clot.

In some examples, the step of restoring perfusion to the blood vessel further includes applying aspiration to the blood vessel through one or more catheters of a delivery system used to deliver the clot retrieval device to the blood vessel.

In some examples, the final revascularization rate is achieved with rescue therapy.

In some examples, the final revascularization rate is achieved by using the clot retrieval device without rescue therapy.

In some examples, a clinically effective clot retrieval device is disclosed for treating ischemic stroke and restoring perfusion to the blood vessel. The device can have a collapsed delivery configuration and an expanded deployed configuration. The device can include a framework of struts forming a porous inner body flow channel and having a tubular main body portion and a distal portion; and a framework of struts forming an outer tubular body radially surrounding the tubular main body portion of the inner body during the collapsed delivery configuration and the expanded deployed configuration, wherein the outer tubular body is expandable to a radial extent to define a clot reception space. The clot retrieval device can be configured to restore perfusion to the blood vessel by passing the clot retrieval device by, through, or about the clot and removing the clot retrieval device to achieve at least a 90% final clinically effective revascularization rate mTICI≥2b.

In some examples, a clinically effective clot retrieval device is disclosed for treating ischemic stroke and restoring perfusion to the blood vessel. The device can have a collapsed delivery configuration and an expanded deployed configuration. The device can include a framework of struts forming a porous inner body flow channel and having a tubular main body portion and a distal portion; and a framework of struts forming an outer tubular body radially surrounding the tubular main body portion of the inner body during the collapsed delivery configuration and the expanded deployed configuration, wherein the outer tubular body is expandable to a radial extent to define a clot reception space. The clot retrieval device can be configured to restore perfusion to the blood vessel by passing the clot retrieval device by, through, or about the clot and removing the clot retrieval device to achieve at least at least a 69% clinically effective revascularization rate mTICI≥2b after two passes of the clinically effective clot retrieval device by, through, or about the clot.

In some examples, a clinically effective clot retrieval device is disclosed for treating ischemic stroke and restoring perfusion to the blood vessel. The device can have a collapsed delivery configuration and an expanded deployed configuration. The device can include a framework of struts forming a porous inner body flow channel and having a tubular main body portion and a distal portion; and a framework of struts forming an outer tubular body radially surrounding the tubular main body portion of the inner body during the collapsed delivery configuration and the expanded deployed configuration, wherein the outer tubular body is expandable to a radial extent to define a clot reception space. The clot retrieval device can be configured to restore perfusion to the blood vessel by passing the clot retrieval device by, through, or about the clot and removing the clot retrieval device to achieve at least a clinically effective outcome of at least approximately 67%, the clinically effective outcome being mRS of 0-2.

In some examples, a clinically effective clot retrieval device is disclosed for treating ischemic stroke and restoring perfusion to the blood vessel. The device can have a collapsed delivery configuration and an expanded deployed configuration. The device can include a framework of struts forming a porous inner body flow channel and having a tubular main body portion and a distal portion; and a framework of struts forming an outer tubular body radially surrounding the tubular main body portion of the inner body during the collapsed delivery configuration and the expanded deployed configuration, wherein the outer tubular body is expandable to a radial extent to define a clot reception space. The clot retrieval device can be configured to restore perfusion to the blood vessel by passing the clot retrieval device by, through, or about the clot and removing the clot retrieval device to achieve at least a 75% final clinically effective revascularization rate mTICI=3 after procedure completion using the clinically effective clot retrieval device with the clot.

In some examples, a clinically effective clot retrieval device is disclosed for treating ischemic stroke and restoring perfusion to the blood vessel. The device can have a collapsed delivery configuration and an expanded deployed configuration. The device can include a framework of struts forming a porous inner body flow channel and having a tubular main body portion and a distal portion; and a framework of struts forming an outer tubular body radially surrounding the tubular main body portion of the inner body during the collapsed delivery configuration and the expanded deployed configuration, wherein the outer tubular body is expandable to a radial extent to define a clot reception space. The clot retrieval device can be configured to restore perfusion to the blood vessel by passing the clot retrieval device by, through, or about the clot and removing the clot retrieval device to achieve at least a 50% revascularization rate mTICI=3 in the blood vessel by passing the clot retriever device by, through, or about the clot one or more times and retracting proximally the clot retriever device.

In some examples, a clinically effective clot retrieval device is disclosed for treating ischemic stroke and restoring perfusion to the blood vessel. The device can have a collapsed delivery configuration and an expanded deployed configuration. The device can include a framework of struts forming a porous inner body flow channel and having a tubular main body portion and a distal portion; and a framework of struts forming an outer tubular body radially surrounding the tubular main body portion of the inner body during the collapsed delivery configuration and the expanded deployed configuration, wherein the outer tubular body is expandable to a radial extent to define a clot reception space. The clot retrieval device can be configured to restore perfusion to the blood vessel by passing the clot retrieval device by, through, or about the clot and removing the clot retrieval device to achieve a final revascularization rate mTICI≥2c in the blood vessel after three passes of the clot retrieval device by, through, or about the clot that is approximately a 5% improvement from the closest comparable clinical data.

In some examples, a clinically effective clot retrieval device is disclosed for treating ischemic stroke and restoring perfusion to the blood vessel. The device can have a collapsed delivery configuration and an expanded deployed configuration. The device can include a framework of struts forming a porous inner body flow channel and having a tubular main body portion and a distal portion; and a framework of struts forming an outer tubular body radially surrounding the tubular main body portion of the inner body during the collapsed delivery configuration and the expanded deployed configuration, wherein the outer tubular body is expandable to a radial extent to define a clot reception space. The clot retrieval device can be configured to restore perfusion to the blood vessel by passing the clot retrieval device by, through, or about the clot and removing the clot retrieval device to achieve a final revascularization rate mTICI≥2c in the blood vessel after three passes of the clot retrieval device by, through, or about the clot that is approximately a 5% clinically effective improvement from the closest comparable clinical data.

In some examples, a clinically effective clot retrieval device is disclosed for treating ischemic stroke and restoring perfusion to the blood vessel. The device can have a collapsed delivery configuration and an expanded deployed configuration. The device can include a framework of struts forming a porous inner body flow channel and having a tubular main body portion and a distal portion; and a framework of struts forming an outer tubular body radially surrounding the tubular main body portion of the inner body during the collapsed delivery configuration and the expanded deployed configuration, wherein the outer tubular body is expandable to a radial extent to define a clot reception space. The clot retrieval device can be configured to restore perfusion to the blood vessel by passing the clot retrieval device by, through, or about the clot and removing the clot retrieval device to achieve a final complete revascularization rate mTICI=3 in the blood vessel after three passes of the clot retrieval device by, through, or about the clot that is approximately a 10% improvement from the closest comparable clinical data.

In some examples, a clinically effective clot retrieval device is disclosed for treating ischemic stroke and restoring perfusion to the blood vessel. The device can have a collapsed delivery configuration and an expanded deployed configuration. The device can include a framework of struts forming a porous inner body flow channel and having a tubular main body portion and a distal portion; and a framework of struts forming an outer tubular body radially surrounding the tubular main body portion of the inner body during the collapsed delivery configuration and the expanded deployed configuration, wherein the outer tubular body is expandable to a radial extent to define a clot reception space. The clot retrieval device can be configured to restore perfusion to the blood vessel by passing the clot retrieval device by, through, or about the clot and removing the clot retrieval device to achieve a final complete revascularization rate mTICI=3 in the blood vessel after three passes of the clot retrieval device by, through, or about the clot that is approximately a 10% clinically effective improvement from the closest comparable clinical data.

In some examples, a clinically effective clot retrieval device is disclosed for treating ischemic stroke and restoring perfusion to the blood vessel. The device can have a collapsed delivery configuration and an expanded deployed configuration. The device can include a framework of struts forming a porous inner body flow channel and having a tubular main body portion and a distal portion; and a framework of struts forming an outer tubular body radially surrounding the tubular main body portion of the inner body during the collapsed delivery configuration and the expanded deployed configuration, wherein the outer tubular body is expandable to a radial extent to define a clot reception space. The clot retrieval device can be configured to restore perfusion to the blood vessel by passing the clot retrieval device by, through, or about the clot and removing the clot retrieval device to achieve a clinically effective outcome for a population size that is at least 200 patients.

In some examples, a clinically effective clot retrieval device is disclosed for treating ischemic stroke and restoring perfusion to the blood vessel. The device can have a collapsed delivery configuration and an expanded deployed configuration. The device can include a framework of struts forming a porous inner body flow channel and having a tubular main body portion and a distal portion; and a framework of struts forming an outer tubular body radially surrounding the tubular main body portion of the inner body. The distal portion of the inner body can be located within the outer tubular body and adjacent the distal end portion of the outer tubular body, and extending in the deployed configuration towards the outer tubular body to a greater extent than the tubular main body portion. The clot retrieval device can be configured to restore perfusion to the blood vessel by passing the clot retrieval device by, through, or about the clot and removing the clot retrieval device to achieve at least a 90% final clinically effective revascularization rate mTICI≥2b.

In some examples, a clinically effective clot retrieval device is disclosed for treating ischemic stroke and restoring perfusion to the blood vessel. The device can have a collapsed delivery configuration and an expanded deployed configuration. The device can include a framework of struts forming a porous inner body flow channel and having a tubular main body portion and a distal portion; and a framework of struts forming an outer tubular body radially surrounding the tubular main body portion of the inner body. The distal portion of the inner body can be located within the outer tubular body and adjacent the distal end portion of the outer tubular body, and extending in the deployed configuration towards the outer tubular body to a greater extent than the tubular main body portion. The clot retrieval device can be configured to restore perfusion to the blood vessel by passing the clot retrieval device by, through, or about the clot and removing the clot retrieval device to achieve at least a 69% clinically effective revascularization rate mTICI≥2b after two passes of the clinically effective clot retrieval device by, through, or about the clot.

In some examples, a clinically effective clot retrieval device is disclosed for treating ischemic stroke and restoring perfusion to the blood vessel. The device can have a collapsed delivery configuration and an expanded deployed configuration. The device can include a framework of struts forming a porous inner body flow channel and having a tubular main body portion and a distal portion; and a framework of struts forming an outer tubular body radially surrounding the tubular main body portion of the inner body. The distal portion of the inner body can be located within the outer tubular body and adjacent the distal end portion of the outer tubular body, and extending in the deployed configuration towards the outer tubular body to a greater extent than the tubular main body portion. The clot retrieval device can be configured to restore perfusion to the blood vessel by passing the clot retrieval device by, through, or about the clot and removing the clot retrieval device to achieve a clinically effective outcome of at least approximately 67%, the clinically effective outcome being mRS of 0-2.

In some examples, a clinically effective clot retrieval device is disclosed for treating ischemic stroke and restoring perfusion to the blood vessel. The device can have a collapsed delivery configuration and an expanded deployed configuration. The device can include a framework of struts forming a porous inner body flow channel and having a tubular main body portion and a distal portion; and a framework of struts forming an outer tubular body radially surrounding the tubular main body portion of the inner body. The distal portion of the inner body can be located within the outer tubular body and adjacent the distal end portion of the outer tubular body, and extending in the deployed configuration towards the outer tubular body to a greater extent than the tubular main body portion. The clot retrieval device can be configured to restore perfusion to the blood vessel by passing the clot retrieval device by, through, or about the clot and removing the clot retrieval device to achieve at least a 75% final clinically effective revascularization rate mTICI=3 after procedure completion using the clinically effective clot retrieval device with the clot.

In some examples, a clinically effective clot retrieval device is disclosed for treating ischemic stroke and restoring perfusion to the blood vessel. The device can have a collapsed delivery configuration and an expanded deployed configuration. The device can include a framework of struts forming a porous inner body flow channel and having a tubular main body portion and a distal portion; and a framework of struts forming an outer tubular body radially surrounding the tubular main body portion of the inner body. The distal portion of the inner body can be located within the outer tubular body and adjacent the distal end portion of the outer tubular body, and extending in the deployed configuration towards the outer tubular body to a greater extent than the tubular main body portion. The clot retrieval device can be configured to restore perfusion to the blood vessel by passing the clot retrieval device by, through, or about the clot and removing the clot retrieval device to achieve at least a 50% revascularization rate mTICI=3 in the blood vessel by passing the clot retriever device by, through, or about the clot one or more times and retracting proximally the clot retriever device.

In some examples, a clinically effective clot retrieval device is disclosed for treating ischemic stroke and restoring perfusion to the blood vessel. The device can have a collapsed delivery configuration and an expanded deployed configuration. The device can include a framework of struts forming a porous inner body flow channel and having a tubular main body portion and a distal portion; and a framework of struts forming an outer tubular body radially surrounding the tubular main body portion of the inner body. The distal portion of the inner body can be located within the outer tubular body and adjacent the distal end portion of the outer tubular body, and extending in the deployed configuration towards the outer tubular body to a greater extent than the tubular main body portion. The clot retrieval device can be configured to restore perfusion to the blood vessel by passing the clot retrieval device by, through, or about the clot and removing the clot retrieval device to achieve a final revascularization rate mTICI≥2c in the blood vessel after three passes of the clot retrieval device by, through, or about the clot that is approximately a 5% improvement from the closest comparable clinical data.

In some examples, a clinically effective clot retrieval device is disclosed for treating ischemic stroke and restoring perfusion to the blood vessel. The device can have a collapsed delivery configuration and an expanded deployed configuration. The device can include a framework of struts forming a porous inner body flow channel and having a tubular main body portion and a distal portion; and a framework of struts forming an outer tubular body radially surrounding the tubular main body portion of the inner body. The distal portion of the inner body can be located within the outer tubular body and adjacent the distal end portion of the outer tubular body, and extending in the deployed configuration towards the outer tubular body to a greater extent than the tubular main body portion. The clot retrieval device can be configured to restore perfusion to the blood vessel by passing the clot retrieval device by, through, or about the clot and removing the clot retrieval device to achieve a final revascularization rate mTICI≥2c in the blood vessel after three passes of the clot retrieval device by, through, or about the clot that is approximately a 5% clinically effective improvement from the closest comparable clinical data.

In some examples, a clinically effective clot retrieval device is disclosed for treating ischemic stroke and restoring perfusion to the blood vessel. The device can have a collapsed delivery configuration and an expanded deployed configuration. The device can include a framework of struts forming a porous inner body flow channel and having a tubular main body portion and a distal portion; and a framework of struts forming an outer tubular body radially surrounding the tubular main body portion of the inner body. The distal portion of the inner body can be located within the outer tubular body and adjacent the distal end portion of the outer tubular body, and extending in the deployed configuration towards the outer tubular body to a greater extent than the tubular main body portion. The clot retrieval device can be configured to restore perfusion to the blood vessel by passing the clot retrieval device by, through, or about the clot and removing the clot retrieval device to achieve a final complete revascularization rate mTICI=3 in the blood vessel after three passes of the clot retrieval device by, through, or about the clot that is approximately a 10% improvement from the closest comparable clinical data.

In some examples, a clinically effective clot retrieval device is disclosed for treating ischemic stroke and restoring perfusion to the blood vessel. The device can have a collapsed delivery configuration and an expanded deployed configuration. The device can include a framework of struts forming a porous inner body flow channel and having a tubular main body portion and a distal portion; and a framework of struts forming an outer tubular body radially surrounding the tubular main body portion of the inner body. The distal portion of the inner body can be located within the outer tubular body and adjacent the distal end portion of the outer tubular body, and extending in the deployed configuration towards the outer tubular body to a greater extent than the tubular main body portion. The clot retrieval device can be configured to restore perfusion to the blood vessel by passing the clot retrieval device by, through, or about the clot and removing the clot retrieval device to achieve a final complete revascularization rate mTICI=3 in the blood vessel after three passes of the clot retrieval device by, through, or about the clot that is approximately a 10% clinically effective improvement from the closest comparable clinical data.

In some examples, a clinically effective clot retrieval device is disclosed for treating ischemic stroke and restoring perfusion to the blood vessel. The device can have a collapsed delivery configuration and an expanded deployed configuration. The device can include a framework of struts forming a porous inner body flow channel and having a tubular main body portion and a distal portion; and a framework of struts forming an outer tubular body radially surrounding the tubular main body portion of the inner body. The distal portion of the inner body can be located within the outer tubular body and adjacent the distal end portion of the outer tubular body, and extending in the deployed configuration towards the outer tubular body to a greater extent than the tubular main body portion. The clot retrieval device can be configured to restore perfusion to the blood vessel by passing the clot retrieval device by, through, or about the clot and removing the clot retrieval device to achieve a clinically effective outcome for a population size that is at least 200 patients.

In some examples, the distal portion of the inner body includes a plurality of distal struts each having a first end coupled to the tubular main body portion of the inner body and a second end coupled to each other so as to form a connection point. In some examples, the plurality of distal struts of the distal portion are spiraled. In some examples, the plurality of distal struts of the distal portion are configured in a bulged or flared pattern.

In some examples, the distal portion of the inner body and the distal end portion of the outer tubular body together define a protective strut structure configured to prevent distal egress of clot or clot fragments from the device.

In some examples, a clinically effective clot retrieval device is disclosed for treating ischemic stroke and restoring perfusion to the blood vessel. The device can have a collapsed delivery configuration and an expanded deployed configuration. The device can include an inner tubular body having a plurality of openings, a collapsed delivery configuration, and an expanded deployed configuration; and an outer tubular body at least partially overlying the inner tubular body and having a plurality of closed cells. The outer tubular body can include a first scaffolding segment including a plurality of the closed cells, a second scaffolding segment including a plurality of the closed cells and located distally of the first scaffolding segment, the inner tubular body extending inside the first and second scaffolding segments; and a clot inlet mouth located between the first scaffolding segment and the second scaffolding segment for receiving the clot or fragments thereof. The clot retrieval device can be configured to restore perfusion to the blood vessel by passing the clot retrieval device by, through, or about the clot and removing the clot retrieval device to achieve at least a 90% final clinically effective revascularization rate mTICI≥2b.

In some examples, a clinically effective clot retrieval device is disclosed for treating ischemic stroke and restoring perfusion to the blood vessel. The device can have a collapsed delivery configuration and an expanded deployed configuration. The device can include an inner tubular body having a plurality of openings, a collapsed delivery configuration, and an expanded deployed configuration; and an outer tubular body at least partially overlying the inner tubular body and having a plurality of closed cells. The outer tubular body can include a first scaffolding segment including a plurality of the closed cells, a second scaffolding segment including a plurality of the closed cells and located distally of the first scaffolding segment, the inner tubular body extending inside the first and second scaffolding segments; and a clot inlet mouth located between the first scaffolding segment and the second scaffolding segment for receiving the clot or fragments thereof. The clot retrieval device can be configured to restore perfusion to the blood vessel by passing the clot retrieval device by, through, or about the clot and removing the clot retrieval device to achieve at least a 69% clinically effective revascularization rate mTICI≥2b after two passes of the clinically effective clot retrieval device by, through, or about the clot.

In some examples, a clinically effective clot retrieval device is disclosed for treating ischemic stroke and restoring perfusion to the blood vessel. The device can have a collapsed delivery configuration and an expanded deployed configuration. The device can include an inner tubular body having a plurality of openings, a collapsed delivery configuration, and an expanded deployed configuration; and an outer tubular body at least partially overlying the inner tubular body and having a plurality of closed cells. The outer tubular body can include a first scaffolding segment including a plurality of the closed cells, a second scaffolding segment including a plurality of the closed cells and located distally of the first scaffolding segment, the inner tubular body extending inside the first and second scaffolding segments; and a clot inlet mouth located between the first scaffolding segment and the second scaffolding segment for receiving the clot or fragments thereof. The clot retrieval device can be configured to restore perfusion to the blood vessel by passing the clot retrieval device by, through, or about the clot and removing the clot retrieval device to achieve a clinically effective outcome of at least approximately 67%, the clinically effective outcome being mRS of 0-2.

In some examples, a clinically effective clot retrieval device is disclosed for treating ischemic stroke and restoring perfusion to the blood vessel. The device can have a collapsed delivery configuration and an expanded deployed configuration. The device can include an inner tubular body having a plurality of openings, a collapsed delivery configuration, and an expanded deployed configuration; and an outer tubular body at least partially overlying the inner tubular body and having a plurality of closed cells. The outer tubular body can include a first scaffolding segment including a plurality of the closed cells, a second scaffolding segment including a plurality of the closed cells and located distally of the first scaffolding segment, the inner tubular body extending inside the first and second scaffolding segments; and a clot inlet mouth located between the first scaffolding segment and the second scaffolding segment for receiving the clot or fragments thereof. The clot retrieval device can be configured to restore perfusion to the blood vessel by passing the clot retrieval device by, through, or about the clot and removing the clot retrieval device to achieve at least a 75% final clinically effective revascularization rate mTICI=3 after procedure completion using the clinically effective clot retrieval device with the clot.

In some examples, a clinically effective clot retrieval device is disclosed for treating ischemic stroke and restoring perfusion to the blood vessel. The device can have a collapsed delivery configuration and an expanded deployed configuration. The device can include an inner tubular body having a plurality of openings, a collapsed delivery configuration, and an expanded deployed configuration; and an outer tubular body at least partially overlying the inner tubular body and having a plurality of closed cells. The outer tubular body can include a first scaffolding segment including a plurality of the closed cells, a second scaffolding segment including a plurality of the closed cells and located distally of the first scaffolding segment, the inner tubular body extending inside the first and second scaffolding segments; and a clot inlet mouth located between the first scaffolding segment and the second scaffolding segment for receiving the clot or fragments thereof. The clot retrieval device can be configured to restore perfusion to the blood vessel by passing the clot retrieval device by, through, or about the clot and removing the clot retrieval device to achieve at least a 50% revascularization rate mTICI=3 in the blood vessel by passing the clot retriever device by, through, or about the clot one or more times and retracting proximally the clot retriever device.

In some examples, a clinically effective clot retrieval device is disclosed for treating ischemic stroke and restoring perfusion to the blood vessel. The device can have a collapsed delivery configuration and an expanded deployed configuration. The device can include an inner tubular body having a plurality of openings, a collapsed delivery configuration, and an expanded deployed configuration; and an outer tubular body at least partially overlying the inner tubular body and having a plurality of closed cells. The outer tubular body can include a first scaffolding segment including a plurality of the closed cells, a second scaffolding segment including a plurality of the closed cells and located distally of the first scaffolding segment, the inner tubular body extending inside the first and second scaffolding segments; and a clot inlet mouth located between the first scaffolding segment and the second scaffolding segment for receiving the clot or fragments thereof. The clot retrieval device can be configured to restore perfusion to the blood vessel by passing the clot retrieval device by, through, or about the clot and removing the clot retrieval device to achieve a final revascularization rate mTICI≥2c in the blood vessel after three passes of the clot retrieval device by, through, or about the clot that is approximately a 5% improvement from the closest comparable clinical data.

In some examples, a clinically effective clot retrieval device is disclosed for treating ischemic stroke and restoring perfusion to the blood vessel. The device can have a collapsed delivery configuration and an expanded deployed configuration. The device can include an inner tubular body having a plurality of openings, a collapsed delivery configuration, and an expanded deployed configuration; and an outer tubular body at least partially overlying the inner tubular body and having a plurality of closed cells. The outer tubular body can include a first scaffolding segment including a plurality of the closed cells, a second scaffolding segment including a plurality of the closed cells and located distally of the first scaffolding segment, the inner tubular body extending inside the first and second scaffolding segments; and a clot inlet mouth located between the first scaffolding segment and the second scaffolding segment for receiving the clot or fragments thereof. The clot retrieval device can be configured to restore perfusion to the blood vessel by passing the clot retrieval device by, through, or about the clot and removing the clot retrieval device to achieve a final revascularization rate mTICI≥2c in the blood vessel after three passes of the clot retrieval device by, through, or about the clot that is approximately a 5% clinically effective improvement from the closest comparable clinical data.

In some examples, a clinically effective clot retrieval device is disclosed for treating ischemic stroke and restoring perfusion to the blood vessel. The device can have a collapsed delivery configuration and an expanded deployed configuration. The device can include an inner tubular body having a plurality of openings, a collapsed delivery configuration, and an expanded deployed configuration; and an outer tubular body at least partially overlying the inner tubular body and having a plurality of closed cells. The outer tubular body can include a first scaffolding segment including a plurality of the closed cells, a second scaffolding segment including a plurality of the closed cells and located distally of the first scaffolding segment, the inner tubular body extending inside the first and second scaffolding segments; and a clot inlet mouth located between the first scaffolding segment and the second scaffolding segment for receiving the clot or fragments thereof. The clot retrieval device can be configured to restore perfusion to the blood vessel by passing the clot retrieval device by, through, or about the clot and removing the clot retrieval device to achieve a final complete revascularization rate mTICI=3 in the blood vessel after three passes of the clot retrieval device by, through, or about the clot that is approximately a 10% improvement from the closest comparable clinical data.

In some examples, a clinically effective clot retrieval device is disclosed for treating ischemic stroke and restoring perfusion to the blood vessel. The device can have a collapsed delivery configuration and an expanded deployed configuration. The device can include an inner tubular body having a plurality of openings, a collapsed delivery configuration, and an expanded deployed configuration; and an outer tubular body at least partially overlying the inner tubular body and having a plurality of closed cells. The outer tubular body can include a first scaffolding segment including a plurality of the closed cells, a second scaffolding segment including a plurality of the closed cells and located distally of the first scaffolding segment, the inner tubular body extending inside the first and second scaffolding segments; and a clot inlet mouth located between the first scaffolding segment and the second scaffolding segment for receiving the clot or fragments thereof. The clot retrieval device can be configured to restore perfusion to the blood vessel by passing the clot retrieval device by, through, or about the clot and removing the clot retrieval device to achieve a final complete revascularization rate mTICI=3 in the blood vessel after three passes of the clot retrieval device by, through, or about the clot that is approximately a 10% clinically effective improvement from the closest comparable clinical data.

In some examples, a clinically effective clot retrieval device is disclosed for treating ischemic stroke and restoring perfusion to the blood vessel. The device can have a collapsed delivery configuration and an expanded deployed configuration. The device can include an inner tubular body having a plurality of openings, a collapsed delivery configuration, and an expanded deployed configuration; and an outer tubular body at least partially overlying the inner tubular body and having a plurality of closed cells. The outer tubular body can include a first scaffolding segment including a plurality of the closed cells, a second scaffolding segment including a plurality of the closed cells and located distally of the first scaffolding segment, the inner tubular body extending inside the first and second scaffolding segments; and a clot inlet mouth located between the first scaffolding segment and the second scaffolding segment for receiving the clot or fragments thereof. The clot retrieval device can be configured to restore perfusion to the blood vessel by passing the clot retrieval device by, through, or about the clot and removing the clot retrieval device to achieve a clinically effective outcome for a population size that is at least 200 patients.

In some examples, the clot inlet mouth is unscaffolded and includes an opening larger than any one of the plurality of cells of the first and second scaffolding segments.

In some examples, the second scaffolding segment includes more of the closed cells than the first scaffolding segment.

In some examples, the clot inlet mouth forms a disconnection between the first scaffolding segment and the second scaffolding segment over a circumferential arc of approximately 180 degrees.

In some examples, a longitudinal distance between the first scaffolding segment and the second scaffolding segment is the same in the expanded deployed configuration as during retrieval of the device.

In some examples, the clot inlet mouth is a first clot inlet mouth, the device further including a third scaffolding segment located distally of the second scaffolding segment and a second clot inlet mouth located between the second and third scaffolding segments for receiving the clot or fragments thereof. The first and second clot inlet mouths each can include an opening larger than any one of the cells of the first, second, and third scaffolding segments.

In some examples, a clinically effective clot retrieval device is disclosed for treating ischemic stroke and restoring perfusion to the blood vessel. The device can have a collapsed delivery configuration and an expanded deployed configuration. The device can include an inner tubular body having a plurality of closed cells that form an inner flow channel, a collapsed delivery configuration, and an expanded deployed configuration; and an outer tubular body at least partially overlying the inner tubular body and having a plurality of closed cells larger than the closed cells of the inner body. The clot retrieval device can be configured to restore perfusion to the blood vessel by passing the clot retrieval device by, through, or about the clot and removing the clot retrieval device to achieve at least a 90% final clinically effective revascularization rate mTICI≥2b.

In some examples, a clinically effective clot retrieval device is disclosed for treating ischemic stroke and restoring perfusion to the blood vessel. The device can have a collapsed delivery configuration and an expanded deployed configuration. The device can include an inner tubular body having a plurality of closed cells that form an inner flow channel, a collapsed delivery configuration, and an expanded deployed configuration; and an outer tubular body at least partially overlying the inner tubular body and having a plurality of closed cells larger than the closed cells of the inner body. The clot retrieval device can be configured to restore perfusion to the blood vessel by passing the clot retrieval device by, through, or about the clot and removing the clot retrieval device to achieve at least a 69% clinically effective revascularization rate mTICI≥2b after two passes of the clinically effective clot retrieval device by, through, or about the clot.

In some examples, a clinically effective clot retrieval device is disclosed for treating ischemic stroke and restoring perfusion to the blood vessel. The device can have a collapsed delivery configuration and an expanded deployed configuration. The device can include an inner tubular body having a plurality of closed cells that form an inner flow channel, a collapsed delivery configuration, and an expanded deployed configuration; and an outer tubular body at least partially overlying the inner tubular body and having a plurality of closed cells larger than the closed cells of the inner body. The clot retrieval device can be configured to restore perfusion to the blood vessel by passing the clot retrieval device by, through, or about the clot and removing the clot retrieval device to achieve a clinically effective outcome of at least approximately 67%, the clinically effective outcome being mRS of 0-2.

In some examples, a clinically effective clot retrieval device is disclosed for treating ischemic stroke and restoring perfusion to the blood vessel. The device can have a collapsed delivery configuration and an expanded deployed configuration. The device can include an inner tubular body having a plurality of closed cells that form an inner flow channel, a collapsed delivery configuration, and an expanded deployed configuration; and an outer tubular body at least partially overlying the inner tubular body and having a plurality of closed cells larger than the closed cells of the inner body. The clot retrieval device can be configured to restore perfusion to the blood vessel by passing the clot retrieval device by, through, or about the clot and removing the clot retrieval device to achieve at least a 75% final clinically effective revascularization rate mTICI=3 after procedure completion using the clinically effective clot retrieval device with the clot.

In some examples, a clinically effective clot retrieval device is disclosed for treating ischemic stroke and restoring perfusion to the blood vessel. The device can have a collapsed delivery configuration and an expanded deployed configuration. The device can include an inner tubular body having a plurality of closed cells that form an inner flow channel, a collapsed delivery configuration, and an expanded deployed configuration; and an outer tubular body at least partially overlying the inner tubular body and having a plurality of closed cells larger than the closed cells of the inner body. The clot retrieval device can be configured to restore perfusion to the blood vessel by passing the clot retrieval device by, through, or about the clot and removing the clot retrieval device to achieve at least a 50% revascularization rate mTICI=3 in the blood vessel by passing the clot retriever device by, through, or about the clot one or more times and retracting proximally the clot retriever device.

In some examples, a clinically effective clot retrieval device is disclosed for treating ischemic stroke and restoring perfusion to the blood vessel. The device can have a collapsed delivery configuration and an expanded deployed configuration. The device can include an inner tubular body having a plurality of closed cells that form an inner flow channel, a collapsed delivery configuration, and an expanded deployed configuration; and an outer tubular body at least partially overlying the inner tubular body and having a plurality of closed cells larger than the closed cells of the inner body. The clot retrieval device can be configured to restore perfusion to the blood vessel by passing the clot retrieval device by, through, or about the clot and removing the clot retrieval device to achieve a final revascularization rate mTICI≥2c in the blood vessel after three passes of the clot retrieval device by, through, or about the clot that is approximately a 5% improvement from the closest comparable clinical data.

In some examples, a clinically effective clot retrieval device is disclosed for treating ischemic stroke and restoring perfusion to the blood vessel. The device can have a collapsed delivery configuration and an expanded deployed configuration. The device can include an inner tubular body having a plurality of closed cells that form an inner flow channel, a collapsed delivery configuration, and an expanded deployed configuration; and an outer tubular body at least partially overlying the inner tubular body and having a plurality of closed cells larger than the closed cells of the inner body. The clot retrieval device can be configured to restore perfusion to the blood vessel by passing the clot retrieval device by, through, or about the clot and removing the clot retrieval device to achieve a final revascularization rate mTICI≥2c in the blood vessel after three passes of the clot retrieval device by, through, or about the clot that is approximately a 5% clinically effective improvement from the closest comparable clinical data.

In some examples, a clinically effective clot retrieval device is disclosed for treating ischemic stroke and restoring perfusion to the blood vessel. The device can have a collapsed delivery configuration and an expanded deployed configuration. The device can include an inner tubular body having a plurality of closed cells that form an inner flow channel, a collapsed delivery configuration, and an expanded deployed configuration; and an outer tubular body at least partially overlying the inner tubular body and having a plurality of closed cells larger than the closed cells of the inner body. The clot retrieval device can be configured to restore perfusion to the blood vessel by passing the clot retrieval device by, through, or about the clot and removing the clot retrieval device to achieve a final complete revascularization rate mTICI=3 in the blood vessel after three passes of the clot retrieval device by, through, or about the clot that is approximately a 10% improvement from the closest comparable clinical data.

In some examples, a clinically effective clot retrieval device is disclosed for treating ischemic stroke and restoring perfusion to the blood vessel. The device can have a collapsed delivery configuration and an expanded deployed configuration. The device can include an inner tubular body having a plurality of closed cells that form an inner flow channel, a collapsed delivery configuration, and an expanded deployed configuration; and an outer tubular body at least partially overlying the inner tubular body and having a plurality of closed cells larger than the closed cells of the inner body. The clot retrieval device can be configured to restore perfusion to the blood vessel by passing the clot retrieval device by, through, or about the clot and removing the clot retrieval device to achieve at least a 75% final clinically effective revascularization rate mTICI=3 after procedure completion using the clinically effective clot retrieval device with the clot.

In some examples, a clinically effective clot retrieval device is disclosed for treating ischemic stroke and restoring perfusion to the blood vessel. The device can have a collapsed delivery configuration and an expanded deployed configuration. The device can include an inner tubular body having a plurality of closed cells that form an inner flow channel, a collapsed delivery configuration, and an expanded deployed configuration; and an outer tubular body at least partially overlying the inner tubular body and having a plurality of closed cells larger than the closed cells of the inner body. The clot retrieval device can be configured to restore perfusion to the blood vessel by passing the clot retrieval device by, through, or about the clot and removing the clot retrieval device to achieve a final complete revascularization rate mTICI=3 in the blood vessel after three passes of the clot retrieval device by, through, or about the clot that is approximately a 10% clinically effective improvement from the closest comparable clinical data.

In some examples, a clinically effective clot retrieval device is disclosed for treating ischemic stroke and restoring perfusion to the blood vessel. The device can have a collapsed delivery configuration and an expanded deployed configuration. The device can include an inner tubular body having a plurality of closed cells that form an inner flow channel, a collapsed delivery configuration, and an expanded deployed configuration; and an outer tubular body at least partially overlying the inner tubular body and having a plurality of closed cells larger than the closed cells of the inner body. The clot retrieval device can be configured to restore perfusion to the blood vessel by passing the clot retrieval device by, through, or about the clot and removing the clot retrieval device to achieve a clinically effective outcome for a population size that is at least 200 patients.

In some examples, a clinically effective clot retrieval device is disclosed for treating ischemic stroke and restoring perfusion to the blood vessel. The device can have a collapsed delivery configuration and an expanded deployed configuration. The device can include an inner tubular body having a plurality of openings, a collapsed delivery configuration, and an expanded deployed configuration; and an outer tubular body at least partially overlying the inner tubular body and having a plurality of closed cells. The outer tubular body can include a first scaffolding segment including a plurality of the closed cells, a second scaffolding segment including a plurality of the closed cells and located distally of the first scaffolding segment, the inner tubular body extending inside the first and second scaffolding segments; and a hinge connecting the first and second scaffolding segments, the hinge including a pair of connecting elements, each connecting element connected at a proximal end to the first scaffolding segment and at a distal end to the second scaffolding segment. The clot retrieval device can be configured to restore perfusion to the blood vessel by passing the clot retrieval device by, through, or about the clot and removing the clot retrieval device to achieve at least a 90% final clinically effective revascularization rate mTICI≥2b.

In some examples, a clinically effective clot retrieval device is disclosed for treating ischemic stroke and restoring perfusion to the blood vessel. The device can have a collapsed delivery configuration and an expanded deployed configuration. The device can include an inner tubular body having a plurality of openings, a collapsed delivery configuration, and an expanded deployed configuration; and an outer tubular body at least partially overlying the inner tubular body and having a plurality of closed cells. The outer tubular body can include a first scaffolding segment including a plurality of the closed cells, a second scaffolding segment including a plurality of the closed cells and located distally of the first scaffolding segment, the inner tubular body extending inside the first and second scaffolding segments; and a hinge connecting the first and second scaffolding segments, the hinge including a pair of connecting elements, each connecting element connected at a proximal end to the first scaffolding segment and at a distal end to the second scaffolding segment. The clot retrieval device can be configured to restore perfusion to the blood vessel by passing the clot retrieval device by, through, or about the clot and removing the clot retrieval device to achieve at least a 69% clinically effective revascularization rate mTICI≥2b after two passes of the clinically effective clot retrieval device by, through, or about the clot.

In some examples, a clinically effective clot retrieval device is disclosed for treating ischemic stroke and restoring perfusion to the blood vessel. The device can have a collapsed delivery configuration and an expanded deployed configuration. The device can include an inner tubular body having a plurality of openings, a collapsed delivery configuration, and an expanded deployed configuration; and an outer tubular body at least partially overlying the inner tubular body and having a plurality of closed cells. The outer tubular body can include a first scaffolding segment including a plurality of the closed cells, a second scaffolding segment including a plurality of the closed cells and located distally of the first scaffolding segment, the inner tubular body extending inside the first and second scaffolding segments; and a hinge connecting the first and second scaffolding segments, the hinge including a pair of connecting elements, each connecting element connected at a proximal end to the first scaffolding segment and at a distal end to the second scaffolding segment. The clot retrieval device can be configured to restore perfusion to the blood vessel by passing the clot retrieval device by, through, or about the clot and removing the clot retrieval device to achieve a clinically effective outcome of at least approximately 67%, the clinically effective outcome being mRS of 0-2.

In some examples, a clinically effective clot retrieval device is disclosed for treating ischemic stroke and restoring perfusion to the blood vessel. The device can have a collapsed delivery configuration and an expanded deployed configuration. The device can include an inner tubular body having a plurality of openings, a collapsed delivery configuration, and an expanded deployed configuration; and an outer tubular body at least partially overlying the inner tubular body and having a plurality of closed cells. The outer tubular body can include a first scaffolding segment including a plurality of the closed cells, a second scaffolding segment including a plurality of the closed cells and located distally of the first scaffolding segment, the inner tubular body extending inside the first and second scaffolding segments; and a hinge connecting the first and second scaffolding segments, the hinge including a pair of connecting elements, each connecting element connected at a proximal end to the first scaffolding segment and at a distal end to the second scaffolding segment. The clot retrieval device can be configured to restore perfusion to the blood vessel by passing the clot retrieval device by, through, or about the clot and removing the clot retrieval device to achieve at least a 75% final clinically effective revascularization rate mTICI=3 after procedure completion using the clinically effective clot retrieval device with the clot.

In some examples, a clinically effective clot retrieval device is disclosed for treating ischemic stroke and restoring perfusion to the blood vessel. The device can have a collapsed delivery configuration and an expanded deployed configuration. The device can include an inner tubular body having a plurality of openings, a collapsed delivery configuration, and an expanded deployed configuration; and an outer tubular body at least partially overlying the inner tubular body and having a plurality of closed cells. The outer tubular body can include a first scaffolding segment including a plurality of the closed cells, a second scaffolding segment including a plurality of the closed cells and located distally of the first scaffolding segment, the inner tubular body extending inside the first and second scaffolding segments; and a hinge connecting the first and second scaffolding segments, the hinge including a pair of connecting elements, each connecting element connected at a proximal end to the first scaffolding segment and at a distal end to the second scaffolding segment. The clot retrieval device can be configured to restore perfusion to the blood vessel by passing the clot retrieval device by, through, or about the clot and removing the clot retrieval device to achieve at least a 50% revascularization rate mTICI=3 in the blood vessel by passing the clot retriever device by, through, or about the clot one or more times and retracting proximally the clot retriever device.

In some examples, a clinically effective clot retrieval device is disclosed for treating ischemic stroke and restoring perfusion to the blood vessel. The device can have a collapsed delivery configuration and an expanded deployed configuration. The device can include an inner tubular body having a plurality of openings, a collapsed delivery configuration, and an expanded deployed configuration; and an outer tubular body at least partially overlying the inner tubular body and having a plurality of closed cells. The outer tubular body can include a first scaffolding segment including a plurality of the closed cells, a second scaffolding segment including a plurality of the closed cells and located distally of the first scaffolding segment, the inner tubular body extending inside the first and second scaffolding segments; and a hinge connecting the first and second scaffolding segments, the hinge including a pair of connecting elements, each connecting element connected at a proximal end to the first scaffolding segment and at a distal end to the second scaffolding segment. The clot retrieval device can be configured to restore perfusion to the blood vessel by passing the clot retrieval device by, through, or about the clot and removing the clot retrieval device to achieve a final revascularization rate mTICI≥2c in the blood vessel after three passes of the clot retrieval device by, through, or about the clot that is approximately a 5% improvement from the closest comparable clinical data.

In some examples, a clinically effective clot retrieval device is disclosed for treating ischemic stroke and restoring perfusion to the blood vessel. The device can have a collapsed delivery configuration and an expanded deployed configuration. The device can include an inner tubular body having a plurality of openings, a collapsed delivery configuration, and an expanded deployed configuration; and an outer tubular body at least partially overlying the inner tubular body and having a plurality of closed cells. The outer tubular body can include a first scaffolding segment including a plurality of the closed cells, a second scaffolding segment including a plurality of the closed cells and located distally of the first scaffolding segment, the inner tubular body extending inside the first and second scaffolding segments; and a hinge connecting the first and second scaffolding segments, the hinge including a pair of connecting elements, each connecting element connected at a proximal end to the first scaffolding segment and at a distal end to the second scaffolding segment. The clot retrieval device can be configured to restore perfusion to the blood vessel by passing the clot retrieval device by, through, or about the clot and removing the clot retrieval device to achieve a final revascularization rate mTICI≥2c in the blood vessel after three passes of the clot retrieval device by, through, or about the clot that is approximately a 5% clinically effective improvement from the closest comparable clinical data.

In some examples, a clinically effective clot retrieval device is disclosed for treating ischemic stroke and restoring perfusion to the blood vessel. The device can have a collapsed delivery configuration and an expanded deployed configuration. The device can include an inner tubular body having a plurality of openings, a collapsed delivery configuration, and an expanded deployed configuration; and an outer tubular body at least partially overlying the inner tubular body and having a plurality of closed cells. The outer tubular body can include a first scaffolding segment including a plurality of the closed cells, a second scaffolding segment including a plurality of the closed cells and located distally of the first scaffolding segment, the inner tubular body extending inside the first and second scaffolding segments; and a hinge connecting the first and second scaffolding segments, the hinge including a pair of connecting elements, each connecting element connected at a proximal end to the first scaffolding segment and at a distal end to the second scaffolding segment. The clot retrieval device can be configured to restore perfusion to the blood vessel by passing the clot retrieval device by, through, or about the clot and removing the clot retrieval device to achieve a final complete revascularization rate mTICI=3 in the blood vessel after three passes of the clot retrieval device by, through, or about the clot that is approximately a 10% improvement from the closest comparable clinical data.

In some examples, a clinically effective clot retrieval device is disclosed for treating ischemic stroke and restoring perfusion to the blood vessel. The device can have a collapsed delivery configuration and an expanded deployed configuration. The device can include an inner tubular body having a plurality of openings, a collapsed delivery configuration, and an expanded deployed configuration; and an outer tubular body at least partially overlying the inner tubular body and having a plurality of closed cells. The outer tubular body can include a first scaffolding segment including a plurality of the closed cells, a second scaffolding segment including a plurality of the closed cells and located distally of the first scaffolding segment, the inner tubular body extending inside the first and second scaffolding segments; and a hinge connecting the first and second scaffolding segments, the hinge including a pair of connecting elements, each connecting element connected at a proximal end to the first scaffolding segment and at a distal end to the second scaffolding segment. The clot retrieval device can be configured to restore perfusion to the blood vessel by passing the clot retrieval device by, through, or about the clot and removing the clot retrieval device to achieve a final complete revascularization rate mTICI=3 in the blood vessel after three passes of the clot retrieval device by, through, or about the clot that is approximately a 10% clinically effective improvement from the closest comparable clinical data.

In some examples, a clinically effective clot retrieval device is disclosed for treating ischemic stroke and restoring perfusion to the blood vessel. The device can have a collapsed delivery configuration and an expanded deployed configuration. The device can include an inner tubular body having a plurality of openings, a collapsed delivery configuration, and an expanded deployed configuration; and an outer tubular body at least partially overlying the inner tubular body and having a plurality of closed cells. The outer tubular body can include a first scaffolding segment including a plurality of the closed cells, a second scaffolding segment including a plurality of the closed cells and located distally of the first scaffolding segment, the inner tubular body extending inside the first and second scaffolding segments; and a hinge connecting the first and second scaffolding segments, the hinge including a pair of connecting elements, each connecting element connected at a proximal end to the first scaffolding segment and at a distal end to the second scaffolding segment. The clot retrieval device can be configured to restore perfusion to the blood vessel by passing the clot retrieval device by, through, or about the clot and removing the clot retrieval device to achieve a clinically effective outcome for a population size that is at least 200 patients.

In some examples, the hinge forms the only connection of the outer tubular body between the first and second scaffolding segments.

In some examples, the hinge is formed from a pair of opposed connecting members connecting the first and second segments, each connecting member connected at a proximal end to the first segment and at a distal end to the second segment.

In some examples, the unscaffolded clot inlet mouth is a first clot inlet mouth, and the hinge is a first hinge, and the device further includes a third scaffolding segment located distally of the second scaffolding segment, and a second hinge aligned with the first hinge and extending between the second and third scaffolding segments.

In some examples, a clinically effective clot retrieval device is disclosed for treating ischemic stroke and restoring perfusion to the blood vessel. The device can have a collapsed delivery configuration and an expanded deployed configuration. The device can include a shaft extending between a proximal end and a distal end; an inner expandable body including a plurality of struts coupled to the distal end of the shaft, an expandable outer body at least partially overlying the inner expandable body and being expandable to a radial extent greater than the radial extent of the inner expandable body in the deployed configuration to provide, wherein the outer body comprises a plurality of longitudinally spaced clot scaffolding segments comprising closed cells whereby each segment is separated by a clot inlet mouth, wherein at least one closed cell of each clot scaffolding segment terminates in a distal apex free from connection to an adjacent closed cell. The clot retrieval device can be configured to restore perfusion to the blood vessel by passing the clot retrieval device by, through, or about the clot and removing the clot retrieval device to achieve at least a 90% final clinically effective revascularization rate mTICI≥2b.

In some examples, a clinically effective clot retrieval device is disclosed for treating ischemic stroke and restoring perfusion to the blood vessel. The device can have a collapsed delivery configuration and an expanded deployed configuration. The device can include a shaft extending between a proximal end and a distal end; an inner expandable body including a plurality of struts coupled to the distal end of the shaft, an expandable outer body at least partially overlying the inner expandable body and being expandable to a radial extent greater than the radial extent of the inner expandable body in the deployed configuration to provide, wherein the outer body comprises a plurality of longitudinally spaced clot scaffolding segments comprising closed cells whereby each segment is separated by a clot inlet mouth, wherein at least one closed cell of each clot scaffolding segment terminates in a distal apex free from connection to an adjacent closed cell. The clot retrieval device can be configured to restore perfusion to the blood vessel by passing the clot retrieval device by, through, or about the clot and removing the clot retrieval device to achieve at least a 69% clinically effective revascularization rate mTICI≥2b after two passes of the clinically effective clot retrieval device by, through, or about the clot.

In some examples, a clinically effective clot retrieval device is disclosed for treating ischemic stroke and restoring perfusion to the blood vessel. The device can have a collapsed delivery configuration and an expanded deployed configuration. The device can include a shaft extending between a proximal end and a distal end; an inner expandable body including a plurality of struts coupled to the distal end of the shaft, an expandable outer body at least partially overlying the inner expandable body and being expandable to a radial extent greater than the radial extent of the inner expandable body in the deployed configuration to provide, wherein the outer body comprises a plurality of longitudinally spaced clot scaffolding segments comprising closed cells whereby each segment is separated by a clot inlet mouth, wherein at least one closed cell of each clot scaffolding segment terminates in a distal apex free from connection to an adjacent closed cell. The clot retrieval device can be configured to restore perfusion to the blood vessel by passing the clot retrieval device by, through, or about the clot and removing the clot retrieval device to achieve a clinically effective outcome of at least approximately 67%, the clinically effective outcome being mRS of 0-2.

In some examples, a clinically effective clot retrieval device is disclosed for treating ischemic stroke and restoring perfusion to the blood vessel. The device can have a collapsed delivery configuration and an expanded deployed configuration. The device can include a shaft extending between a proximal end and a distal end; an inner expandable body including a plurality of struts coupled to the distal end of the shaft, an expandable outer body at least partially overlying the inner expandable body and being expandable to a radial extent greater than the radial extent of the inner expandable body in the deployed configuration to provide, wherein the outer body comprises a plurality of longitudinally spaced clot scaffolding segments comprising closed cells whereby each segment is separated by a clot inlet mouth, wherein at least one closed cell of each clot scaffolding segment terminates in a distal apex free from connection to an adjacent closed cell. The clot retrieval device can be configured to restore perfusion to the blood vessel by passing the clot retrieval device by, through, or about the clot and removing the clot retrieval device to achieve at least a 75% final clinically effective revascularization rate mTICI=3 after procedure completion using the clinically effective clot retrieval device with the clot.

In some examples, a clinically effective clot retrieval device is disclosed for treating ischemic stroke and restoring perfusion to the blood vessel. The device can have a collapsed delivery configuration and an expanded deployed configuration. The device can include a shaft extending between a proximal end and a distal end; an inner expandable body including a plurality of struts coupled to the distal end of the shaft, an expandable outer body at least partially overlying the inner expandable body and being expandable to a radial extent greater than the radial extent of the inner expandable body in the deployed configuration to provide, wherein the outer body comprises a plurality of longitudinally spaced clot scaffolding segments comprising closed cells whereby each segment is separated by a clot inlet mouth, wherein at least one closed cell of each clot scaffolding segment terminates in a distal apex free from connection to an adjacent closed cell. The clot retrieval device can be configured to restore perfusion to the blood vessel by passing the clot retrieval device by, through, or about the clot and removing the clot retrieval device to achieve at least a 50% revascularization rate mTICI=3 in the blood vessel by passing the clot retriever device by, through, or about the clot one or more times and retracting proximally the clot retriever device.

In some examples, a clinically effective clot retrieval device is disclosed for treating ischemic stroke and restoring perfusion to the blood vessel. The device can have a collapsed delivery configuration and an expanded deployed configuration. The device can include a shaft extending between a proximal end and a distal end; an inner expandable body including a plurality of struts coupled to the distal end of the shaft, an expandable outer body at least partially overlying the inner expandable body and being expandable to a radial extent greater than the radial extent of the inner expandable body in the deployed configuration to provide, wherein the outer body comprises a plurality of longitudinally spaced clot scaffolding segments comprising closed cells whereby each segment is separated by a clot inlet mouth, wherein at least one closed cell of each clot scaffolding segment terminates in a distal apex free from connection to an adjacent closed cell. The clot retrieval device can be configured to restore perfusion to the blood vessel by passing the clot retrieval device by, through, or about the clot and removing the clot retrieval device to achieve a final revascularization rate mTICI≥2c in the blood vessel after three passes of the clot retrieval device by, through, or about the clot that is approximately a 5% improvement from the closest comparable clinical data.

In some examples, a clinically effective clot retrieval device is disclosed for treating ischemic stroke and restoring perfusion to the blood vessel. The device can have a collapsed delivery configuration and an expanded deployed configuration. The device can include a shaft extending between a proximal end and a distal end; an inner expandable body including a plurality of struts coupled to the distal end of the shaft, an expandable outer body at least partially overlying the inner expandable body and being expandable to a radial extent greater than the radial extent of the inner expandable body in the deployed configuration to provide, wherein the outer body comprises a plurality of longitudinally spaced clot scaffolding segments comprising closed cells whereby each segment is separated by a clot inlet mouth, wherein at least one closed cell of each clot scaffolding segment terminates in a distal apex free from connection to an adjacent closed cell. The clot retrieval device can be configured to restore perfusion to the blood vessel by passing the clot retrieval device by, through, or about the clot and removing the clot retrieval device to achieve a final revascularization rate mTICI≥2c in the blood vessel after three passes of the clot retrieval device by, through, or about the clot that is approximately a 5% clinically effective improvement from the closest comparable clinical data.

In some examples, a clinically effective clot retrieval device is disclosed for treating ischemic stroke and restoring perfusion to the blood vessel. The device can have a collapsed delivery configuration and an expanded deployed configuration. The device can include a shaft extending between a proximal end and a distal end; an inner expandable body including a plurality of struts coupled to the distal end of the shaft, an expandable outer body at least partially overlying the inner expandable body and being expandable to a radial extent greater than the radial extent of the inner expandable body in the deployed configuration to provide, wherein the outer body comprises a plurality of longitudinally spaced clot scaffolding segments comprising closed cells whereby each segment is separated by a clot inlet mouth, wherein at least one closed cell of each clot scaffolding segment terminates in a distal apex free from connection to an adjacent closed cell. The clot retrieval device can be configured to restore perfusion to the blood vessel by passing the clot retrieval device by, through, or about the clot and removing the clot retrieval device to achieve a final complete revascularization rate mTICI=3 in the blood vessel after three passes of the clot retrieval device by, through, or about the clot that is approximately a 10% improvement from the closest comparable clinical data.

In some examples, a clinically effective clot retrieval device is disclosed for treating ischemic stroke and restoring perfusion to the blood vessel. The device can have a collapsed delivery configuration and an expanded deployed configuration. The device can include a shaft extending between a proximal end and a distal end; an inner expandable body including a plurality of struts coupled to the distal end of the shaft, an expandable outer body at least partially overlying the inner expandable body and being expandable to a radial extent greater than the radial extent of the inner expandable body in the deployed configuration to provide, wherein the outer body comprises a plurality of longitudinally spaced clot scaffolding segments comprising closed cells whereby each segment is separated by a clot inlet mouth, wherein at least one closed cell of each clot scaffolding segment terminates in a distal apex free from connection to an adjacent closed cell. The clot retrieval device can be configured to restore perfusion to the blood vessel by passing the clot retrieval device by, through, or about the clot and removing the clot retrieval device to achieve a final complete revascularization rate mTICI=3 in the blood vessel after three passes of the clot retrieval device by, through, or about the clot that is approximately a 10% clinically effective improvement from the closest comparable clinical data.

In some examples, a clinically effective clot retrieval device is disclosed for treating ischemic stroke and restoring perfusion to the blood vessel. The device can have a collapsed delivery configuration and an expanded deployed configuration. The device can include a shaft extending between a proximal end and a distal end; an inner expandable body including a plurality of struts coupled to the distal end of the shaft, an expandable outer body at least partially overlying the inner expandable body and being expandable to a radial extent greater than the radial extent of the inner expandable body in the deployed configuration to provide, wherein the outer body comprises a plurality of longitudinally spaced clot scaffolding segments comprising closed cells whereby each segment is separated by a clot inlet mouth, wherein at least one closed cell of each clot scaffolding segment terminates in a distal apex free from connection to an adjacent closed cell. The clot retrieval device can be configured to restore perfusion to the blood vessel by passing the clot retrieval device by, through, or about the clot and removing the clot retrieval device to achieve a clinically effective outcome for a population size that is at least 200 patients.

In some examples, each clot inlet mouth is formed by two connections between adjacent clot scaffolding segments.

In some examples, each clot inlet mouth is formed by two connections between adjacent clot scaffolding segments, and wherein the connections are 180° degrees apart from each other.

In some examples, each clot inlet mouth is formed by two connections that form an articulated joint between adjacent clot scaffolding segments.

In some examples, each clot inlet mouth is formed by two connections that are 180° degrees apart from each other and form an articulated joint between clot scaffolding segments.

In some examples, the outer body is eccentrically coupled to the shaft.

In some examples, the inner expandable body and the outer expandable body are coupled to the shaft at a common location.

In some examples, the inner body includes a cylindrical and tubular portion, and wherein the cylindrical and tubular portion extends completely through a proximal most and a next proximal most scaffolding segment of the at least three clot scaffolding segments.

In some examples, a clinically effective clot retrieval device is disclosed for treating ischemic stroke and restoring perfusion to the blood vessel. The device can have a collapsed delivery configuration and an expanded deployed configuration. The device can include a shaft extending between a proximal end and a distal end; an inner expandable body including a plurality of struts formed with the distal end of the shaft, an expandable outer body at least partially overlying the inner expandable body and being expandable to a radial extent greater than the radial extent of the inner expandable body in the deployed configuration to provide. The clot retrieval device can be configured to restore perfusion to the blood vessel by passing the clot retrieval device by, through, or about the clot and removing the clot retrieval device to achieve at least a 90% final clinically effective revascularization rate mTICI≥2b.

In some examples, a clinically effective clot retrieval device is disclosed for treating ischemic stroke and restoring perfusion to the blood vessel. The device can have a collapsed delivery configuration and an expanded deployed configuration. The device can include a shaft extending between a proximal end and a distal end; an inner expandable body including a plurality of struts formed with the distal end of the shaft, an expandable outer body at least partially overlying the inner expandable body and being expandable to a radial extent greater than the radial extent of the inner expandable body in the deployed configuration to provide. The clot retrieval device can be configured to restore perfusion to the blood vessel by passing the clot retrieval device by, through, or about the clot and removing the clot retrieval device to achieve at least a 69% clinically effective revascularization rate mTICI≥2b after two passes of the clinically effective clot retrieval device by, through, or about the clot.

In some examples, a clinically effective clot retrieval device is disclosed for treating ischemic stroke and restoring perfusion to the blood vessel. The device can have a collapsed delivery configuration and an expanded deployed configuration. The device can include a shaft extending between a proximal end and a distal end; an inner expandable body including a plurality of struts formed with the distal end of the shaft, an expandable outer body at least partially overlying the inner expandable body and being expandable to a radial extent greater than the radial extent of the inner expandable body in the deployed configuration to provide. The clot retrieval device can be configured to restore perfusion to the blood vessel by passing the clot retrieval device by, through, or about the clot and removing the clot retrieval device to achieve a clinically effective outcome of at least approximately 67%, the clinically effective outcome being mRS of 0-2.

In some examples, a clinically effective clot retrieval device is disclosed for treating ischemic stroke and restoring perfusion to the blood vessel. The device can have a collapsed delivery configuration and an expanded deployed configuration. The device can include a shaft extending between a proximal end and a distal end; an inner expandable body including a plurality of struts formed with the distal end of the shaft, an expandable outer body at least partially overlying the inner expandable body and being expandable to a radial extent greater than the radial extent of the inner expandable body in the deployed configuration to provide. The clot retrieval device can be configured to restore perfusion to the blood vessel by passing the clot retrieval device by, through, or about the clot and removing the clot retrieval device to achieve at least a 75% final clinically effective revascularization rate mTICI=3 after procedure completion using the clinically effective clot retrieval device with the clot.

In some examples, a clinically effective clot retrieval device is disclosed for treating ischemic stroke and restoring perfusion to the blood vessel. The device can have a collapsed delivery configuration and an expanded deployed configuration. The device can include a shaft extending between a proximal end and a distal end; an inner expandable body including a plurality of struts formed with the distal end of the shaft, an expandable outer body at least partially overlying the inner expandable body and being expandable to a radial extent greater than the radial extent of the inner expandable body in the deployed configuration to provide. The clot retrieval device can be configured to restore perfusion to the blood vessel by passing the clot retrieval device by, through, or about the clot and removing the clot retrieval device to achieve at least a 50% revascularization rate mTICI=3 in the blood vessel by passing the clot retriever device by, through, or about the clot one or more times and retracting proximally the clot retriever device.

In some examples, a clinically effective clot retrieval device is disclosed for treating ischemic stroke and restoring perfusion to the blood vessel. The device can have a collapsed delivery configuration and an expanded deployed configuration. The device can include a shaft extending between a proximal end and a distal end; an inner expandable body including a plurality of struts formed with the distal end of the shaft, an expandable outer body at least partially overlying the inner expandable body and being expandable to a radial extent greater than the radial extent of the inner expandable body in the deployed configuration to provide. The clot retrieval device can be configured to restore perfusion to the blood vessel by passing the clot retrieval device by, through, or about the clot and removing the clot retrieval device to achieve a final revascularization rate mTICI≥2c in the blood vessel after three passes of the clot retrieval device by, through, or about the clot that is approximately a 5% improvement from the closest comparable clinical data.

In some examples, a clinically effective clot retrieval device is disclosed for treating ischemic stroke and restoring perfusion to the blood vessel. The device can have a collapsed delivery configuration and an expanded deployed configuration. The device can include a shaft extending between a proximal end and a distal end; an inner expandable body including a plurality of struts formed with the distal end of the shaft, an expandable outer body at least partially overlying the inner expandable body and being expandable to a radial extent greater than the radial extent of the inner expandable body in the deployed configuration to provide. The clot retrieval device can be configured to restore perfusion to the blood vessel by passing the clot retrieval device by, through, or about the clot and removing the clot retrieval device to achieve a final revascularization rate mTICI≥2c in the blood vessel after three passes of the clot retrieval device by, through, or about the clot that is approximately a 5% clinically effective improvement from the closest comparable clinical data.

In some examples, a clinically effective clot retrieval device is disclosed for treating ischemic stroke and restoring perfusion to the blood vessel. The device can have a collapsed delivery configuration and an expanded deployed configuration. The device can include a shaft extending between a proximal end and a distal end; an inner expandable body including a plurality of struts formed with the distal end of the shaft, an expandable outer body at least partially overlying the inner expandable body and being expandable to a radial extent greater than the radial extent of the inner expandable body in the deployed configuration to provide. The clot retrieval device can be configured to restore perfusion to the blood vessel by passing the clot retrieval device by, through, or about the clot and removing the clot retrieval device to achieve a final complete revascularization rate mTICI=3 in the blood vessel after three passes of the clot retrieval device by, through, or about the clot that is approximately a 10% improvement from the closest comparable clinical data.

In some examples, a clinically effective clot retrieval device is disclosed for treating ischemic stroke and restoring perfusion to the blood vessel. The device can have a collapsed delivery configuration and an expanded deployed configuration. The device can include a shaft extending between a proximal end and a distal end; an inner expandable body including a plurality of struts formed with the distal end of the shaft, an expandable outer body at least partially overlying the inner expandable body and being expandable to a radial extent greater than the radial extent of the inner expandable body in the deployed configuration to provide. The clot retrieval device can be configured to restore perfusion to the blood vessel by passing the clot retrieval device by, through, or about the clot and removing the clot retrieval device to achieve a final complete revascularization rate mTICI=3 in the blood vessel after three passes of the clot retrieval device by, through, or about the clot that is approximately a 10% clinically effective improvement from the closest comparable clinical data.

In some examples, a clinically effective clot retrieval device is disclosed for treating ischemic stroke and restoring perfusion to the blood vessel. The device can have a collapsed delivery configuration and an expanded deployed configuration. The device can include a shaft extending between a proximal end and a distal end; an inner expandable body including a plurality of struts formed with the distal end of the shaft, an expandable outer body at least partially overlying the inner expandable body and being expandable to a radial extent greater than the radial extent of the inner expandable body in the deployed configuration to provide. The clot retrieval device can be configured to restore perfusion to the blood vessel by passing the clot retrieval device by, through, or about the clot and removing the clot retrieval device to achieve a clinically effective outcome for a population size that is at least 200 patients.

In some examples, a clinically effective clot retrieval device is disclosed for treating ischemic stroke and restoring perfusion to the blood vessel. The device can have a collapsed delivery configuration and an expanded deployed configuration. The device can include an inner tubular body having a plurality of openings, a collapsed delivery configuration, and an expanded deployed configuration; and an outer tubular body at least partially overlying the inner tubular body and having a plurality of closed cells. The outer tubular body can include a first scaffolding segment including a plurality of the closed cells, a second scaffolding segment including a plurality of the closed cells and located distally of the first scaffolding segment, the inner tubular body extending inside the first and second scaffolding segments; a first clot inlet mouth located between the first scaffolding segment and the second scaffolding segment for receiving the clot or fragments thereof; a third scaffolding segment located distally of the second scaffolding segment and including a plurality of the closed cells; and a second clot inlet mouth located between the second and third scaffolding segments for receiving the clot or fragments thereof. The clot retrieval device can be configured to restore perfusion to the blood vessel by passing the clot retrieval device by, through, or about the clot and removing the clot retrieval device to achieve at least a 90% final clinically effective revascularization rate mTICI≥2b.

In some examples, a clinically effective clot retrieval device is disclosed for treating ischemic stroke and restoring perfusion to the blood vessel. The device can have a collapsed delivery configuration and an expanded deployed configuration. The device can include an inner tubular body having a plurality of openings, a collapsed delivery configuration, and an expanded deployed configuration; and an outer tubular body at least partially overlying the inner tubular body and having a plurality of closed cells. The outer tubular body can include a first scaffolding segment including a plurality of the closed cells, a second scaffolding segment including a plurality of the closed cells and located distally of the first scaffolding segment, the inner tubular body extending inside the first and second scaffolding segments; a first clot inlet mouth located between the first scaffolding segment and the second scaffolding segment for receiving the clot or fragments thereof; a third scaffolding segment located distally of the second scaffolding segment and including a plurality of the closed cells; and a second clot inlet mouth located between the second and third scaffolding segments for receiving the clot or fragments thereof. The clot retrieval device can be configured to restore perfusion to the blood vessel by passing the clot retrieval device by, through, or about the clot and removing the clot retrieval device to achieve at least a 69% clinically effective revascularization rate mTICI≥2b after two passes of the clinically effective clot retrieval device by, through, or about the clot.

In some examples, a clinically effective clot retrieval device is disclosed for treating ischemic stroke and restoring perfusion to the blood vessel. The device can have a collapsed delivery configuration and an expanded deployed configuration. The device can include an inner tubular body having a plurality of openings, a collapsed delivery configuration, and an expanded deployed configuration; and an outer tubular body at least partially overlying the inner tubular body and having a plurality of closed cells. The outer tubular body can include a first scaffolding segment including a plurality of the closed cells, a second scaffolding segment including a plurality of the closed cells and located distally of the first scaffolding segment, the inner tubular body extending inside the first and second scaffolding segments; a first clot inlet mouth located between the first scaffolding segment and the second scaffolding segment for receiving the clot or fragments thereof; a third scaffolding segment located distally of the second scaffolding segment and including a plurality of the closed cells; and a second clot inlet mouth located between the second and third scaffolding segments for receiving the clot or fragments thereof. The clot retrieval device can be configured to restore perfusion to the blood vessel by passing the clot retrieval device by, through, or about the clot and removing the clot retrieval device to achieve a clinically effective outcome of at least approximately 67%, the clinically effective outcome being mRS of 0-2.

In some examples, a clinically effective clot retrieval device is disclosed for treating ischemic stroke and restoring perfusion to the blood vessel. The device can have a collapsed delivery configuration and an expanded deployed configuration. The device can include an inner tubular body having a plurality of openings, a collapsed delivery configuration, and an expanded deployed configuration; and an outer tubular body at least partially overlying the inner tubular body and having a plurality of closed cells. The outer tubular body can include a first scaffolding segment including a plurality of the closed cells, a second scaffolding segment including a plurality of the closed cells and located distally of the first scaffolding segment, the inner tubular body extending inside the first and second scaffolding segments; a first clot inlet mouth located between the first scaffolding segment and the second scaffolding segment for receiving the clot or fragments thereof; a third scaffolding segment located distally of the second scaffolding segment and including a plurality of the closed cells; and a second clot inlet mouth located between the second and third scaffolding segments for receiving the clot or fragments thereof. The clot retrieval device can be configured to restore perfusion to the blood vessel by passing the clot retrieval device by, through, or about the clot and removing the clot retrieval device to achieve at least a 75% final clinically effective revascularization rate mTICI=3 after procedure completion using the clinically effective clot retrieval device with the clot.

In some examples, a clinically effective clot retrieval device is disclosed for treating ischemic stroke and restoring perfusion to the blood vessel. The device can have a collapsed delivery configuration and an expanded deployed configuration. The device can include an inner tubular body having a plurality of openings, a collapsed delivery configuration, and an expanded deployed configuration; and an outer tubular body at least partially overlying the inner tubular body and having a plurality of closed cells. The outer tubular body can include a first scaffolding segment including a plurality of the closed cells, a second scaffolding segment including a plurality of the closed cells and located distally of the first scaffolding segment, the inner tubular body extending inside the first and second scaffolding segments; a first clot inlet mouth located between the first scaffolding segment and the second scaffolding segment for receiving the clot or fragments thereof; a third scaffolding segment located distally of the second scaffolding segment and including a plurality of the closed cells; and a second clot inlet mouth located between the second and third scaffolding segments for receiving the clot or fragments thereof. The clot retrieval device can be configured to restore perfusion to the blood vessel by passing the clot retrieval device by, through, or about the clot and removing the clot retrieval device to achieve at least a 50% revascularization rate mTICI=3 in the blood vessel by passing the clot retriever device by, through, or about the clot one or more times and retracting proximally the clot retriever device.

In some examples, a clinically effective clot retrieval device is disclosed for treating ischemic stroke and restoring perfusion to the blood vessel. The device can have a collapsed delivery configuration and an expanded deployed configuration. The device can include an inner tubular body having a plurality of openings, a collapsed delivery configuration, and an expanded deployed configuration; and an outer tubular body at least partially overlying the inner tubular body and having a plurality of closed cells. The outer tubular body can include a first scaffolding segment including a plurality of the closed cells, a second scaffolding segment including a plurality of the closed cells and located distally of the first scaffolding segment, the inner tubular body extending inside the first and second scaffolding segments; a first clot inlet mouth located between the first scaffolding segment and the second scaffolding segment for receiving the clot or fragments thereof; a third scaffolding segment located distally of the second scaffolding segment and including a plurality of the closed cells; and a second clot inlet mouth located between the second and third scaffolding segments for receiving the clot or fragments thereof. The clot retrieval device can be configured to restore perfusion to the blood vessel by passing the clot retrieval device by, through, or about the clot and removing the clot retrieval device to achieve a final revascularization rate mTICI≥2c in the blood vessel after three passes of the clot retrieval device by, through, or about the clot that is approximately a 5% improvement from the closest comparable clinical data.

In some examples, a clinically effective clot retrieval device is disclosed for treating ischemic stroke and restoring perfusion to the blood vessel. The device can have a collapsed delivery configuration and an expanded deployed configuration. The device can include an inner tubular body having a plurality of openings, a collapsed delivery configuration, and an expanded deployed configuration; and an outer tubular body at least partially overlying the inner tubular body and having a plurality of closed cells. The outer tubular body can include a first scaffolding segment including a plurality of the closed cells, a second scaffolding segment including a plurality of the closed cells and located distally of the first scaffolding segment, the inner tubular body extending inside the first and second scaffolding segments; a first clot inlet mouth located between the first scaffolding segment and the second scaffolding segment for receiving the clot or fragments thereof; a third scaffolding segment located distally of the second scaffolding segment and including a plurality of the closed cells; and a second clot inlet mouth located between the second and third scaffolding segments for receiving the clot or fragments thereof. The clot retrieval device can be configured to restore perfusion to the blood vessel by passing the clot retrieval device by, through, or about the clot and removing the clot retrieval device to achieve a final revascularization rate mTICI≥2c in the blood vessel after three passes of the clot retrieval device by, through, or about the clot that is approximately a 5% clinically effective improvement from the closest comparable clinical data.

In some examples, a clinically effective clot retrieval device is disclosed for treating ischemic stroke and restoring perfusion to the blood vessel. The device can have a collapsed delivery configuration and an expanded deployed configuration. The device can include an inner tubular body having a plurality of openings, a collapsed delivery configuration, and an expanded deployed configuration; and an outer tubular body at least partially overlying the inner tubular body and having a plurality of closed cells. The outer tubular body can include a first scaffolding segment including a plurality of the closed cells, a second scaffolding segment including a plurality of the closed cells and located distally of the first scaffolding segment, the inner tubular body extending inside the first and second scaffolding segments; a first clot inlet mouth located between the first scaffolding segment and the second scaffolding segment for receiving the clot or fragments thereof; a third scaffolding segment located distally of the second scaffolding segment and including a plurality of the closed cells; and a second clot inlet mouth located between the second and third scaffolding segments for receiving the clot or fragments thereof. The clot retrieval device can be configured to restore perfusion to the blood vessel by passing the clot retrieval device by, through, or about the clot and removing the clot retrieval device to achieve a final complete revascularization rate mTICI=3 in the blood vessel after three passes of the clot retrieval device by, through, or about the clot that is approximately a 10% improvement from the closest comparable clinical data.

In some examples, a clinically effective clot retrieval device is disclosed for treating ischemic stroke and restoring perfusion to the blood vessel. The device can have a collapsed delivery configuration and an expanded deployed configuration. The device can include an inner tubular body having a plurality of openings, a collapsed delivery configuration, and an expanded deployed configuration; and an outer tubular body at least partially overlying the inner tubular body and having a plurality of closed cells. The outer tubular body can include a first scaffolding segment including a plurality of the closed cells, a second scaffolding segment including a plurality of the closed cells and located distally of the first scaffolding segment, the inner tubular body extending inside the first and second scaffolding segments; a first clot inlet mouth located between the first scaffolding segment and the second scaffolding segment for receiving the clot or fragments thereof; a third scaffolding segment located distally of the second scaffolding segment and including a plurality of the closed cells; and a second clot inlet mouth located between the second and third scaffolding segments for receiving the clot or fragments thereof. The clot retrieval device can be configured to restore perfusion to the blood vessel by passing the clot retrieval device by, through, or about the clot and removing the clot retrieval device to achieve a final complete revascularization rate mTICI=3 in the blood vessel after three passes of the clot retrieval device by, through, or about the clot that is approximately a 10% clinically effective improvement from the closest comparable clinical data.

In some examples, a clinically effective clot retrieval device is disclosed for treating ischemic stroke and restoring perfusion to the blood vessel. The device can have a collapsed delivery configuration and an expanded deployed configuration. The device can include an inner tubular body having a plurality of openings, a collapsed delivery configuration, and an expanded deployed configuration; and an outer tubular body at least partially overlying the inner tubular body and having a plurality of closed cells. The outer tubular body can include a first scaffolding segment including a plurality of the closed cells, a second scaffolding segment including a plurality of the closed cells and located distally of the first scaffolding segment, the inner tubular body extending inside the first and second scaffolding segments; a first clot inlet mouth located between the first scaffolding segment and the second scaffolding segment for receiving the clot or fragments thereof; a third scaffolding segment located distally of the second scaffolding segment and including a plurality of the closed cells; and a second clot inlet mouth located between the second and third scaffolding segments for receiving the clot or fragments thereof. The clot retrieval device can be configured to restore perfusion to the blood vessel by passing the clot retrieval device by, through, or about the clot and removing the clot retrieval device to achieve a clinically effective outcome for a population size that is at least 200 patients.

In some examples, a clinically effective clot retrieval device is disclosed for treating ischemic stroke and restoring perfusion to the blood vessel. The device can have a collapsed delivery configuration and an expanded deployed configuration. The device can include a shaft extending between a proximal end and a distal end having a step-up; a first body having a plurality of struts and a proximally extending partial circumferential member disposed about the shaft and extended proximally from at least one of the plurality of struts, the proximally extending partial circumferential member being proximal of the step-up and couplable against the step-up; and a second body having a plurality of struts and a collar on a proximal end of at least one of the plurality of struts, the partial circumferential member and the shaft being positioned within a lumen extending through the collar. The clot retrieval device can be configured to restore perfusion to the blood vessel by passing the clot retrieval device by, through, or about the clot and removing the clot retrieval device to achieve at least a 90% final clinically effective revascularization rate mTICI≥2b.

In some examples, a clinically effective clot retrieval device is disclosed for treating ischemic stroke and restoring perfusion to the blood vessel. The device can have a collapsed delivery configuration and an expanded deployed configuration. The device can include a shaft extending between a proximal end and a distal end having a step-up; a first body having a plurality of struts and a proximally extending partial circumferential member disposed about the shaft and extended proximally from at least one of the plurality of struts, the proximally extending partial circumferential member being proximal of the step-up and couplable against the step-up; and a second body having a plurality of struts and a collar on a proximal end of at least one of the plurality of struts, the partial circumferential member and the shaft being positioned within a lumen extending through the collar. The clot retrieval device can be configured to restore perfusion to the blood vessel by passing the clot retrieval device by, through, or about the clot and removing the clot retrieval device to achieve at least a 69% clinically effective revascularization rate mTICI≥2b after two passes of the clinically effective clot retrieval device by, through, or about the clot.

In some examples, a clinically effective clot retrieval device is disclosed for treating ischemic stroke and restoring perfusion to the blood vessel. The device can have a collapsed delivery configuration and an expanded deployed configuration. The device can include a shaft extending between a proximal end and a distal end having a step-up; a first body having a plurality of struts and a proximally extending partial circumferential member disposed about the shaft and extended proximally from at least one of the plurality of struts, the proximally extending partial circumferential member being proximal of the step-up and couplable against the step-up; and a second body having a plurality of struts and a collar on a proximal end of at least one of the plurality of struts, the partial circumferential member and the shaft being positioned within a lumen extending through the collar. The clot retrieval device can be configured to restore perfusion to the blood vessel by passing the clot retrieval device by, through, or about the clot and removing the clot retrieval device to achieve a clinically effective outcome of at least approximately 67%, the clinically effective outcome being mRS of 0-2.

In some examples, a clinically effective clot retrieval device is disclosed for treating ischemic stroke and restoring perfusion to the blood vessel. The device can have a collapsed delivery configuration and an expanded deployed configuration. The device can include a shaft extending between a proximal end and a distal end having a step-up; a first body having a plurality of struts and a proximally extending partial circumferential member disposed about the shaft and extended proximally from at least one of the plurality of struts, the proximally extending partial circumferential member being proximal of the step-up and couplable against the step-up; and a second body having a plurality of struts and a collar on a proximal end of at least one of the plurality of struts, the partial circumferential member and the shaft being positioned within a lumen extending through the collar. The clot retrieval device can be configured to restore perfusion to the blood vessel by passing the clot retrieval device by, through, or about the clot and removing the clot retrieval device to achieve at least a 75% final clinically effective revascularization rate mTICI=3 after procedure completion using the clinically effective clot retrieval device with the clot.

In some examples, a clinically effective clot retrieval device is disclosed for treating ischemic stroke and restoring perfusion to the blood vessel. The device can have a collapsed delivery configuration and an expanded deployed configuration. The device can include a shaft extending between a proximal end and a distal end having a step-up; a first body having a plurality of struts and a proximally extending partial circumferential member disposed about the shaft and extended proximally from at least one of the plurality of struts, the proximally extending partial circumferential member being proximal of the step-up and couplable against the step-up; and a second body having a plurality of struts and a collar on a proximal end of at least one of the plurality of struts, the partial circumferential member and the shaft being positioned within a lumen extending through the collar. The clot retrieval device can be configured to restore perfusion to the blood vessel by passing the clot retrieval device by, through, or about the clot and removing the clot retrieval device to achieve at least a 50% revascularization rate mTICI=3 in the blood vessel by passing the clot retriever device by, through, or about the clot one or more times and retracting proximally the clot retriever device.

In some examples, a clinically effective clot retrieval device is disclosed for treating ischemic stroke and restoring perfusion to the blood vessel. The device can have a collapsed delivery configuration and an expanded deployed configuration. The device can include a shaft extending between a proximal end and a distal end having a step-up; a first body having a plurality of struts and a proximally extending partial circumferential member disposed about the shaft and extended proximally from at least one of the plurality of struts, the proximally extending partial circumferential member being proximal of the step-up and couplable against the step-up; and a second body having a plurality of struts and a collar on a proximal end of at least one of the plurality of struts, the partial circumferential member and the shaft being positioned within a lumen extending through the collar. The clot retrieval device can be configured to restore perfusion to the blood vessel by passing the clot retrieval device by, through, or about the clot and removing the clot retrieval device to achieve a final revascularization rate mTICI≥2c in the blood vessel after three passes of the clot retrieval device by, through, or about the clot that is approximately a 5% improvement from the closest comparable clinical data.

In some examples, a clinically effective clot retrieval device is disclosed for treating ischemic stroke and restoring perfusion to the blood vessel. The device can have a collapsed delivery configuration and an expanded deployed configuration. The device can include a shaft extending between a proximal end and a distal end having a step-up; a first body having a plurality of struts and a proximally extending partial circumferential member disposed about the shaft and extended proximally from at least one of the plurality of struts, the proximally extending partial circumferential member being proximal of the step-up and couplable against the step-up; and a second body having a plurality of struts and a collar on a proximal end of at least one of the plurality of struts, the partial circumferential member and the shaft being positioned within a lumen extending through the collar. The clot retrieval device can be configured to restore perfusion to the blood vessel by passing the clot retrieval device by, through, or about the clot and removing the clot retrieval device to achieve a final revascularization rate mTICI≥2c in the blood vessel after three passes of the clot retrieval device by, through, or about the clot that is approximately a 5% clinically effective improvement from the closest comparable clinical data.

In some examples, a clinically effective clot retrieval device is disclosed for treating ischemic stroke and restoring perfusion to the blood vessel. The device can have a collapsed delivery configuration and an expanded deployed configuration. The device can include a shaft extending between a proximal end and a distal end having a step-up; a first body having a plurality of struts and a proximally extending partial circumferential member disposed about the shaft and extended proximally from at least one of the plurality of struts, the proximally extending partial circumferential member being proximal of the step-up and couplable against the step-up; and a second body having a plurality of struts and a collar on a proximal end of at least one of the plurality of struts, the partial circumferential member and the shaft being positioned within a lumen extending through the collar. The clot retrieval device can be configured to restore perfusion to the blood vessel by passing the clot retrieval device by, through, or about the clot and removing the clot retrieval device to achieve of the clot retrieval device by, through, or about the clot that is approximately a 10% improvement from the closest comparable clinical data.

In some examples, a clinically effective clot retrieval device is disclosed for treating ischemic stroke and restoring perfusion to the blood vessel. The device can have a collapsed delivery configuration and an expanded deployed configuration. The device can include a shaft extending between a proximal end and a distal end having a step-up; a first body having a plurality of struts and a proximally extending partial circumferential member disposed about the shaft and extended proximally from at least one of the plurality of struts, the proximally extending partial circumferential member being proximal of the step-up and couplable against the step-up; and a second body having a plurality of struts and a collar on a proximal end of at least one of the plurality of struts, the partial circumferential member and the shaft being positioned within a lumen extending through the collar. The clot retrieval device can be configured to restore perfusion to the blood vessel by passing the clot retrieval device by, through, or about the clot and removing the clot retrieval device to achieve a final complete revascularization rate mTICI=3 in the blood vessel after three passes of the clot retrieval device by, through, or about the clot that is approximately a 10% clinically effective improvement from the closest comparable clinical data.

In some examples, a clinically effective clot retrieval device is disclosed for treating ischemic stroke and restoring perfusion to the blood vessel. The device can have a collapsed delivery configuration and an expanded deployed configuration. The device can include a shaft extending between a proximal end and a distal end having a step-up; a first body having a plurality of struts and a proximally extending partial circumferential member disposed about the shaft and extended proximally from at least one of the plurality of struts, the proximally extending partial circumferential member being proximal of the step-up and couplable against the step-up; and a second body having a plurality of struts and a collar on a proximal end of at least one of the plurality of struts, the partial circumferential member and the shaft being positioned within a lumen extending through the collar. The clot retrieval device can be configured to restore perfusion to the blood vessel by passing the clot retrieval device by, through, or about the clot and removing the clot retrieval device to achieve a clinically effective outcome for a population size that is at least 200 patients.

In some examples, a clinically effective clot retrieval device is disclosed for treating ischemic stroke and restoring perfusion to the blood vessel. The device can have a collapsed delivery configuration and an expanded deployed configuration. The device can include a shaft extending between a proximal end and a distal end having a step-up; a first body having a plurality of struts and a proximally extending partial circumferential member disposed about the shaft and extended proximally from at least one of the plurality of struts, the proximally extending partial circumferential member being proximal of the step-up and couplable against the step-up; and a second body having a plurality of struts and a collar on a proximal end of at least one of the plurality of struts, the partial circumferential member and the shaft being positioned within a lumen extending through the collar. The clot retrieval device can be configured to restore perfusion to the blood vessel by passing the clot retrieval device by, through, or about the clot and removing the clot retrieval device to achieve at least a 90% final clinically effective revascularization rate mTICI≥2b.

In some examples, a clinically effective clot retrieval device is disclosed for treating ischemic stroke and restoring perfusion to the blood vessel. The device can have a collapsed delivery configuration and an expanded deployed configuration. The device can include a shaft extending between a proximal end and a distal end having a step-up; a first body having a plurality of struts and a proximally extending partial circumferential member disposed about the shaft and extended proximally from at least one of the plurality of struts, the proximally extending partial circumferential member being proximal of the step-up and couplable against the step-up; and a second body having a plurality of struts and a collar on a proximal end of at least one of the plurality of struts, the partial circumferential member and the shaft being positioned within a lumen extending through the collar. The clot retrieval device can be configured to restore perfusion to the blood vessel by passing the clot retrieval device by, through, or about the clot and removing the clot retrieval device to achieve at least a 69% clinically effective revascularization rate mTICI≥2b after two passes of the clinically effective clot retrieval device by, through, or about the clot.

In some examples, a clinically effective clot retrieval device is disclosed for treating ischemic stroke and restoring perfusion to the blood vessel. The device can have a collapsed delivery configuration and an expanded deployed configuration. The device can include a shaft extending between a proximal end and a distal end having a step-up; a first body having a plurality of struts and a proximally extending partial circumferential member disposed about the shaft and extended proximally from at least one of the plurality of struts, the proximally extending partial circumferential member being proximal of the step-up and couplable against the step-up; and a second body having a plurality of struts and a collar on a proximal end of at least one of the plurality of struts, the partial circumferential member and the shaft being positioned within a lumen extending through the collar. The clot retrieval device can be configured to restore perfusion to the blood vessel by passing the clot retrieval device by, through, or about the clot and removing the clot retrieval device to achieve a clinically effective outcome of at least approximately 67%, the clinically effective outcome being mRS of 0-2.

In some examples, a clinically effective clot retrieval device is disclosed for treating ischemic stroke and restoring perfusion to the blood vessel. The device can have a collapsed delivery configuration and an expanded deployed configuration. The device can include a shaft extending between a proximal end and a distal end having a step-up; a first body having a plurality of struts and a proximally extending partial circumferential member disposed about the shaft and extended proximally from at least one of the plurality of struts, the proximally extending partial circumferential member being proximal of the step-up and couplable against the step-up; and a second body having a plurality of struts and a collar on a proximal end of at least one of the plurality of struts, the partial circumferential member and the shaft being positioned within a lumen extending through the collar. The clot retrieval device can be configured to restore perfusion to the blood vessel by passing the clot retrieval device by, through, or about the clot and removing the clot retrieval device to achieve at least a 75% final clinically effective revascularization rate mTICI=3 after procedure completion using the clinically effective clot retrieval device with the clot.

In some examples, a clinically effective clot retrieval device is disclosed for treating ischemic stroke and restoring perfusion to the blood vessel. The device can have a collapsed delivery configuration and an expanded deployed configuration. The device can include a shaft extending between a proximal end and a distal end having a step-up; a first body having a plurality of struts and a proximally extending partial circumferential member disposed about the shaft and extended proximally from at least one of the plurality of struts, the proximally extending partial circumferential member being proximal of the step-up and couplable against the step-up; and a second body having a plurality of struts and a collar on a proximal end of at least one of the plurality of struts, the partial circumferential member and the shaft being positioned within a lumen extending through the collar. The clot retrieval device can be configured to restore perfusion to the blood vessel by passing the clot retrieval device by, through, or about the clot and removing the clot retrieval device to achieve at least a 50% revascularization rate mTICI=3 in the blood vessel by passing the clot retriever device by, through, or about the clot one or more times and retracting proximally the clot retriever device.

In some examples, a clinically effective clot retrieval device is disclosed for treating ischemic stroke and restoring perfusion to the blood vessel. The device can have a collapsed delivery configuration and an expanded deployed configuration. The device can include a shaft extending between a proximal end and a distal end having a step-up; a first body having a plurality of struts and a proximally extending partial circumferential member disposed about the shaft and extended proximally from at least one of the plurality of struts, the proximally extending partial circumferential member being proximal of the step-up and couplable against the step-up; and a second body having a plurality of struts and a collar on a proximal end of at least one of the plurality of struts, the partial circumferential member and the shaft being positioned within a lumen extending through the collar. The clot retrieval device can be configured to restore perfusion to the blood vessel by passing the clot retrieval device by, through, or about the clot and removing the clot retrieval device to achieve a final revascularization rate mTICI≥2c in the blood vessel after three passes of the clot retrieval device by, through, or about the clot that is approximately a 5% improvement from the closest comparable clinical data.

In some examples, a clinically effective clot retrieval device is disclosed for treating ischemic stroke and restoring perfusion to the blood vessel. The device can have a collapsed delivery configuration and an expanded deployed configuration. The device can include a shaft extending between a proximal end and a distal end having a step-up; a first body having a plurality of struts and a proximally extending partial circumferential member disposed about the shaft and extended proximally from at least one of the plurality of struts, the proximally extending partial circumferential member being proximal of the step-up and couplable against the step-up; and a second body having a plurality of struts and a collar on a proximal end of at least one of the plurality of struts, the partial circumferential member and the shaft being positioned within a lumen extending through the collar. The clot retrieval device can be configured to restore perfusion to the blood vessel by passing the clot retrieval device by, through, or about the clot and removing the clot retrieval device to achieve a final revascularization rate mTICI≥2c in the blood vessel after three passes of the clot retrieval device by, through, or about the clot that is approximately a 5% clinically effective improvement from the closest comparable clinical data.

In some examples, a clinically effective clot retrieval device is disclosed for treating ischemic stroke and restoring perfusion to the blood vessel. The device can have a collapsed delivery configuration and an expanded deployed configuration. The device can include a shaft extending between a proximal end and a distal end having a step-up; a first body having a plurality of struts and a proximally extending partial circumferential member disposed about the shaft and extended proximally from at least one of the plurality of struts, the proximally extending partial circumferential member being proximal of the step-up and couplable against the step-up; and a second body having a plurality of struts and a collar on a proximal end of at least one of the plurality of struts, the partial circumferential member and the shaft being positioned within a lumen extending through the collar. The clot retrieval device can be configured to restore perfusion to the blood vessel by passing the clot retrieval device by, through, or about the clot and removing the clot retrieval device to achieve a final complete revascularization rate mTICI=3 in the blood vessel after three passes of the clot retrieval device by, through, or about the clot that is approximately a 10% improvement from the closest comparable clinical data.

In some examples, a clinically effective clot retrieval device is disclosed for treating ischemic stroke and restoring perfusion to the blood vessel. The device can have a collapsed delivery configuration and an expanded deployed configuration. The device can include a shaft extending between a proximal end and a distal end having a step-up; a first body having a plurality of struts and a proximally extending partial circumferential member disposed about the shaft and extended proximally from at least one of the plurality of struts, the proximally extending partial circumferential member being proximal of the step-up and couplable against the step-up; and a second body having a plurality of struts and a collar on a proximal end of at least one of the plurality of struts, the partial circumferential member and the shaft being positioned within a lumen extending through the collar. The clot retrieval device can be configured to restore perfusion to the blood vessel by passing the clot retrieval device by, through, or about the clot and removing the clot retrieval device to achieve a final complete revascularization rate mTICI=3 in the blood vessel after three passes of the clot retrieval device by, through, or about the clot that is approximately a 10% clinically effective improvement from the closest comparable clinical data.

In some examples, a clinically effective clot retrieval device is disclosed for treating ischemic stroke and restoring perfusion to the blood vessel. The device can have a collapsed delivery configuration and an expanded deployed configuration. The device can include a shaft extending between a proximal end and a distal end having a step-up; a first body having a plurality of struts and a proximally extending partial circumferential member disposed about the shaft and extended proximally from at least one of the plurality of struts, the proximally extending partial circumferential member being proximal of the step-up and couplable against the step-up; and a second body having a plurality of struts and a collar on a proximal end of at least one of the plurality of struts, the partial circumferential member and the shaft being positioned within a lumen extending through the collar. The clot retrieval device can be configured to restore perfusion to the blood vessel by passing the clot retrieval device by, through, or about the clot and removing the clot retrieval device to achieve a clinically effective outcome for a population size that is at least 200 patients.

In some examples, the clot is located in one of the following locations: a carotid artery, a M1 middle cerebral artery, a M2 middle cerebral artery, a basilar artery, and a vertebral artery.

In some examples, the device is further configured to achieve at least a 93% final revascularization rate mTICI≥2b in the blood vessel by passing the clot retriever device by, through, or about the clot one or more times and retracting proximally the clot retriever device.

In some examples, the device is further configured to achieve at least a 51.5% final revascularization rate mTICI=3 in the blood vessel after three passes of the clot retrieval device by, through, or about the clot.

In some examples, the device is further configured to achieve at least a 60% revascularization rate mTICI≥2b in the blood vessel after three passes of the clot retrieval device by, through, or about the clot.

In some examples, the device is further configured to achieve at least a 60% revascularization rate mTICI≥2c in the blood vessel by passing the clot retriever device by, through, or about the clot one or more times and retracting proximally the clot retriever device.

In some examples, the device is further configured to achieve at least a 65% revascularization rate mTICI≥2c in the blood vessel by passing the clot retriever device by, through, or about the clot one or more times and retracting proximally the clot retriever device.

In some examples, the device is further configured to achieve at least a 50% revascularization rate mTICI≥2b in the blood vessel after one pass of the clot retrieval device by, through, or about the clot.

In some examples, the device is further configured to achieve at least a 51.5% revascularization rate mTICI≥2b after one pass of the clot retrieval device by, through, or about the clot.

In some examples, the device is further configured to achieve at least an 80% revascularization rate mTICI≥2b in the blood vessel after three passes of the clot retrieval device by, through, or about the clot.

In some examples, the device is further configured to achieve at least a 75% final revascularization rate mTICI≥2c in the blood vessel after procedure completion with the clot retrieval device by, through, or about the clot.

In some examples, the device is further configured to achieve at least a 92.5% final revascularization rate mTICI≥2b in the blood vessel after procedure completion with the clot retrieval device by, through, or about the clot.

In some examples, the device is further configured to achieve at least a 93% final revascularization rate mTICI≥2b in the blood vessel after procedure completion with the clot retrieval device by, through, or about the clot.

In some examples, the device is further configured to achieve at least a 43% revascularization rate mTICI=3 in the blood vessel after three passes of the clot retrieval device by, through, or about the clot.

In some examples, the device is further configured to achieve at least a 52% revascularization rate mTICI=3 in the blood vessel by passing the clot retriever device by, through, or about the clot one or more times.

In some examples, the device is further configured to achieve at least a 10% revascularization rate mTICI≥2b in the blood vessel after one pass of the clot retrieval device by, through, or about the clot.

In some examples, the device is further configured to achieve at least a 30% revascularization rate mTICI≥2b in the blood vessel after one pass of the clot retrieval device by, through, or about the clot.

In some examples, a method of restoring perfusion to a blood vessel with a clot. The method can include determining inclusion criteria for a patient such as a prestroke modified Rankin Scale (mRS) ≤2; a baseline National Institutes of Health stroke scale (NIHSS) score ≥8 and ≤25; an Alberta Stroke Program early computed tomography (AS-PECT) score ≥6; a core infarct volume <50 mL on magnetic resonance imaging or computed tomography-based imaging (for anterior circulation strokes); and a treatment with intravenous tissue-type plasminogen activator (tPA); if yes, passing a clinically effective clot retriever device of any preceding claim by, through, or about the clot one or more times and retracting proximally the clot retriever device to achieve at least one of at least a 90% final clinically effective revascularization rate mTICI≥2b; at least a 69% clinically effective revascularization rate mTICI≥2b after two passes of the clinically effective clot retrieval device by, through, or about the clot; a clinically effective outcome of at least approximately 67%, the clinically effective outcome being mRS of 0-2; at least a 75% final clinically effective revascularization rate mTICI=3 after procedure completion using the clinically effective clot retrieval device with the clot; and achieving at least a 50% revascularization rate mTICI=3 in the blood vessel by passing the clot retriever device by, through, or about the clot one or more times and retracting proximally the clot retriever device.

In some examples, inclusion criteria for the patient of the method can consist of a time to deliver the clot retrieval device from onset of the ischemic stroke is less than eight (8) hours.

In some examples, inclusion criteria for the patient of the method can consist of a time to deliver the clot retrieval device from onset of the ischemic stroke is less than twelve (12) hours.

In some examples, inclusion criteria for the patient of the method can consist of a time to deliver the clot retrieval device from onset of the ischemic stroke is less than twenty-four (24) hours.

In some examples, a method of restoring perfusion to a blood vessel with a clot within 8 hours of stroke onset, the method can include passing a clinically effective clot retriever device of any preceding claim by, through, or about the clot one or more times and retracting proximally the clot retriever device to achieve at least a 90% final clinically effective revascularization rate mTICI≥2b.

In some examples, a method of restoring perfusion to a blood vessel with a clot within 8 hours of stroke onset, the method can include passing a clinically effective clot retriever device of any preceding claim by, through, or about the clot one or more times and retracting proximally the clot retriever device to achieve at least a 69% clinically effective revascularization rate mTICI≥2b after two passes of the clinically effective clot retrieval device by, through, or about the clot.

In some examples, a method of restoring perfusion to a blood vessel with a clot within 8 hours of stroke onset, the method can include passing a clinically effective clot retriever device of any preceding claim by, through, or about the clot one or more times and retracting proximally the clot retriever device to achieve a clinically effective outcome of at least approximately 67%, the clinically effective outcome being mRS of 0-2.

In some examples, a method of restoring perfusion to a blood vessel with a clot within 8 hours of stroke onset, the method can include passing a clinically effective clot retriever device of any preceding claim by, through, or about the clot one or more times and retracting proximally the clot retriever device to achieve at least a 75% final clinically effective revascularization rate mTICI=3 after procedure completion using the clinically effective clot retrieval device with the clot.

In some examples, a method of restoring perfusion to a blood vessel with a clot within 8 hours of stroke onset, the method can include passing a clinically effective clot retriever device of any preceding claim by, through, or about the clot one or more times and retracting proximally the clot retriever device to achieve at least a 50% revascularization rate mTICI=3 in the blood vessel by passing the clot retriever device by, through, or about the clot one or more times and retracting proximally the clot retriever device.

In some examples, a method of restoring perfusion to a blood vessel with a clot within 8 hours of stroke onset, the method can include passing a clinically effective clot retriever device of any preceding claim by, through, or about the clot one or more times and retracting proximally the clot retriever device to achieve a final revascularization rate mTICI≥2c in the blood vessel after three passes of the clot retrieval device by, through, or about the clot that is approximately a 5% improvement from the closest comparable clinical data.

In some examples, a method of restoring perfusion to a blood vessel with a clot within 8 hours of stroke onset, the method can include passing a clinically effective clot retriever device of any preceding claim by, through, or about the clot one or more times and retracting proximally the clot retriever device to achieve a final revascularization rate mTICI≥2c in the blood vessel after three passes of the clot retrieval device by, through, or about the clot that is approximately a 5% clinically effective improvement from the closest comparable clinical data.

In some examples, a method of restoring perfusion to a blood vessel with a clot within 8 hours of stroke onset, the method can include passing a clinically effective clot retriever device of any preceding claim by, through, or about the clot one or more times and retracting proximally the clot retriever device to achieve a final complete revascularization rate mTICI=3 in the blood vessel after three passes of the clot retrieval device by, through, or about the clot that is approximately a 10% improvement from the closest comparable clinical data.

In some examples, a method of restoring perfusion to a blood vessel with a clot within 8 hours of stroke onset, the method can include passing a clinically effective clot retriever device of any preceding claim by, through, or about the clot one or more times and retracting proximally the clot retriever device to achieve a final complete revascularization rate mTICI=3 in the blood vessel after three passes of the clot retrieval device by, through, or about the clot that is approximately a 10% clinically effective improvement from the closest comparable clinical data.

In some examples, a method of restoring perfusion to a blood vessel with a clot within 8 hours of stroke onset, the method can include passing a clinically effective clot retriever device of any preceding claim by, through, or about the clot one or more times and retracting proximally the clot retriever device to achieve a clinically effective outcome for a population size that is at least 200 patients.

In some examples, the method is administered to the patient within 12 hours of stroke onset.

In some examples, the method is administered to the patient within 24 hours of stroke onset.

In some examples, the method can include leaving the clot retrieval device in, about, or in communication with the clot for at least 3 minutes for embedding of the clot to the clot retrieval device.

In some examples, the method can include imaging the patient; determining whether the patient exhibits at least one of the following risk factors a prestroke modified Rankin Scale (mRS)≤2; a baseline National Institutes of Health stroke scale (NIHSS) score ≥8 and ≤25; an Alberta Stroke Program early computed tomography (ASPECT) score ≥6; a core infarct volume <50 mL on magnetic resonance imaging or computed tomography-based imaging (for anterior circulation strokes); and a treatment with intravenous tissue-type plasminogen activator (tPA); administering the device to the blood vessel; and retrieving the clot.

In some examples, the restoring perfusion to the blood vessel is caused by withdrawing some or all of the clot after passing the clot retrieval device by, through, or about the clot.

In some examples, the restoring perfusion to the blood vessel is caused by retracting the clot retrieval device after the clot has embedded with the clot retrieval device.

In some examples, a pass of the clot retrieval device includes positioning the distal end of the clot retrieval device distal of the clot; and retracting proximally the clot retrieval device to a distal end of a microcatheter.

In some examples, the clot is disposed in the internal carotid artery.

In some examples, the clot is disposed in the M1 segment of the middle cerebral artery.

In some examples, the clot is disposed in the M2 segment of the middle cerebral artery.

In some examples, the clot is disposed in the vertebral artery.

In some examples, the clot is disposed in the basilar arteries.

In some examples, the method includes embedding the clot retrieval device with the clot for one minute or less and retracting the clot retrieval device.

In some examples, the method includes embedding the clot retrieval device with the clot for two minutes or less and retracting the clot retrieval device.

In some examples, the method includes embedding the clot retrieval device with the clot for three minutes or less and retracting the clot retrieval device.

In some examples, the method includes embedding the clot retrieval device with the clot for four minutes or less and retracting the clot retrieval device.

In some examples, the method includes passing the clinically effective clot retrieval device two (2) or fewer passes by, through, or about the clot and retracting the clinically effective clot retrieval device; and restoring perfusion in 54 minutes or less time from initial delivery of the clinically effective clot retrieval device.

In some examples, the method includes advancing the clinically effective clot retrieval device so that a distal end of a microcatheter is positioned distal of the occlusion and then passing the clot retrieval device by, through, or about the clot and retracting the clinically effective clot retrieval device.

In some examples, the final revascularization rate is achieved with rescue therapy.

In some examples, the final revascularization rate is achieved by using the clot retrieval device without rescue therapy.

In some examples, the restoring perfusion to the blood vessel further includes applying aspiration to the blood vessel through one or more catheters of a delivery system used to deliver the clot retrieval device to the blood vessel.

In some examples, a reperfusion system is disclosed for restoring perfusion to a blood vessel having an occlusion. The system can include a clinically effective clot retrieval device according to this disclosure; an aspiration system in communication with the clinically effective clot retrieval device; and a delivery system configured to deliver the clinically effective clot retrieval device to the occlusion and in communication with the aspiration system. The aspiration system can be configured to restore perfusion to the blood vessel through a microcatheter of the delivery system.

An example method of treating ischemic stroke can include delivering a clot retrieval device to a blood vessel of the patient for retrieving a clot and restoring perfusion to the blood vessel by passing, two passes or less, the clot retrieval device by, through, or about the clot and removing the clot retrieval device to modify a clot composition of the clot to be more red blood cell rich.

Another example method of treating ischemic stroke can include administering a clinically effective clot retrieval device to a blood vessel of the patient for retrieving the clot and restoring perfusion to the blood vessel to achieve by passing, two passes or less, the clot retrieval device by, through, or about the clot and removing the clot retrieval device to modify a clot composition of the clot to be more red blood cell rich.

Another example method of treating an ischemic stroke can include delivering and passing at least one clot retrieval device two or fewer passes through an occluded blood vessel to modify a clot composition of the clot to be more red blood cell rich.

Another example method of treating an ischemic stroke can include any combination of steps of example methods as shown and described herein that are compatible as understood by a person skilled in the pertinent art.

An example device for a clot can include any combination of features of example devices as shown and described herein that are compatible as understood by a person skilled in the pertinent art.

An example system for a clot can include any combination of features of example systems as shown and described herein that are compatible as understood by a person skilled in the pertinent art.

To the accomplishment of the foregoing and related ends, certain illustrative aspects are described herein in connection with the following description and the appended drawings. These aspects are indicative, however, of but a few of the various ways in which the principles of the claimed subject matter may be employed and the claimed subject matter is intended to include all such aspects and their equivalents. Other advantages and novel features may become apparent from the following detailed description when considered in conjunction with the drawings.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIG. 5 is a table summarizing baseline characteristics for the first study of this disclosure.

FIG. 6 is a table summarizing intra-procedural characteristics for the study of this disclosure.

FIG. 7 is a table of recanalization rates of the first study of this disclosure.

FIG. 9 is a table summarizing the influence of balloon guide catheter usage versus non-balloon guide catheter usage on outcomes.

FIG. 13 is a table summarizing baseline characteristics for the second study of this disclosure.

FIG. 14 is a table summarizing angiographic and clinical outcomes for the second study of this disclosure.

FIG. 15 is a table summarizing safety outcome results for the second study of this disclosure.

FIG. 22 depicts a graphical overview of one method of treating ischemic stroke according to this disclosure.

FIG. 23 depicts a graphical overview of one method of treating ischemic stroke according to this disclosure.

FIG. 24 depicts a graphical overview of one method of treating ischemic stroke according to this disclosure.

FIG. 25 depicts a graphical overview of one method of treating ischemic stroke according to this disclosure.

FIG. 26 depicts a graphical overview of one method of treating ischemic stroke according to this disclosure.

FIG. 27 is a table summarizing information from a study of this disclosure.

FIG. 28 is a table summarizing information from a study of this disclosure.

FIG. 29 is a table summarizing information from a study of this disclosure.

FIG. 30 is a table summarizing information from a study of this disclosure.

FIG. 31A is a table summarizing per-patient long-term costs based on functional outcomes of a study of this disclosure.

FIG. 31B is a table summarizing per-patient procedural healthcare resource use costs for a study of this disclosure.

FIG. 36A depicts a table summarizing per pass improved mTICI information from the study of this disclosure.

FIG. 36B depicts a table summarizing per pass mTICI and 90-day mRS information from the study of this disclosure.

DETAILED DESCRIPTION

Figure 1:
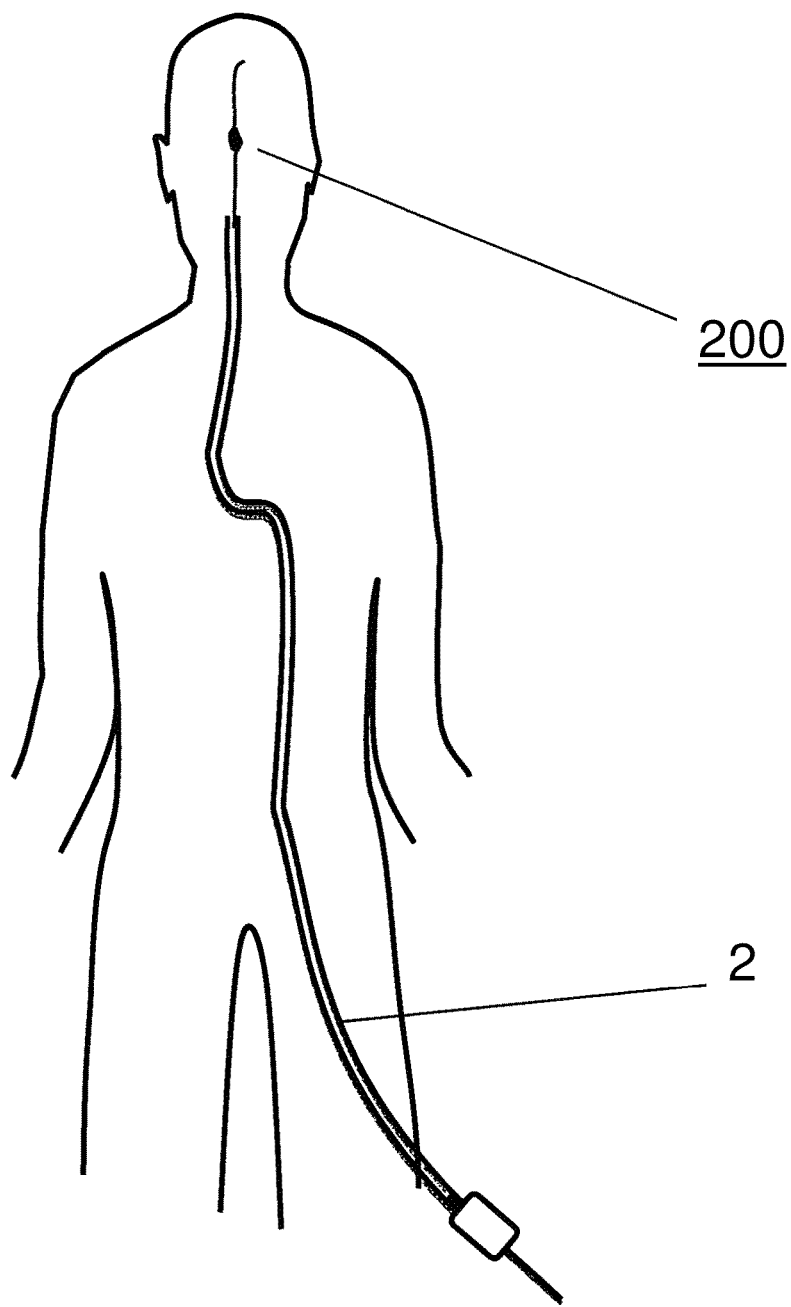
FIG. 1 shows a patient catheterized via femoral access with an example clot retrieval device positioned in a cerebral vessel using the arterial system for its delivery.

Although example embodiments of the disclosed technology are explained in detail herein, it is to be understood that other embodiments are contemplated. Accordingly, it is not intended that the disclosed technology be limited in its scope to the details of construction and arrangement of components set forth in the following description or illustrated in the drawings. The disclosed technology is capable of other embodiments and of being practiced or carried out in various ways.

It must also be noted that, as used in the specification and the appended claims, the singular forms "a," "an" and "the" include plural referents unless the context clearly dictates otherwise. By "comprising" or "containing" or "including" it is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the disclosed technology. Similarly, it is also to be understood that the mention of one or more components in a device or system does not preclude the presence of additional components or intervening components between those components expressly identified.

As discussed herein, vasculature of a "subject" or "patient" may be vasculature of a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to a human (e.g., rat, dog, pig, monkey, or the like). It should be appreciated that the subject may be any applicable human patient, for example.

As discussed herein, "operator" may include a doctor, surgeon, or any other individual or delivery instrumentation associated with delivery of a clot retrieval device to the vasculature of a subject.

As discussed herein, "thrombus" can be understood as a clot in the circulatory system that remains in a site of the vasculature hindering or otherwise obstructing flow in a blood vessel. The terms, "clot", "thrombus", "obstruction", "occlusion", "blockage", and/or the like, can be and are often used interchangeably throughout this disclosure.

Delivery of a "revascularization device" is typically accomplished via delivery of one or more catheters into the femoral artery and/or the radial artery, guided into the arteries of the brain, vascular bypass, angioplasty, and/or the like. "Revascularization devices" can include, but not be limited to, one or more stents, stentrievers, clot removal devices, clot retrieval devices, aspiration systems, one or more combinations thereof, and/or the like, each of which are often used interchangeably throughout this disclosure.

As discussed herein, "mTICI" means modified thrombolysis in cerebral infarction (TICI) score. An mTICI score of 0 means no perfusion. An mTICI score of 1 means antegrade reperfusion past the initial occlusion but limited distal branch filling with little or slow distal reperfusion. An mTICI score of 2 generally means incomplete antegrade reperfusion wherein the contrast passes the occlusion and opacifies the distal arterial bed but there are residual antegrade perfusion deficits. More particularly, an mTICI score of 2a means antegrade reperfusion of less than half of the occluded target artery previously ischemic territory (e.g., in 1 major division of the MCA and its territory). An mTICI score of 2b means antegrade reperfusion of more than half of the previously occluded target artery ischemic territory (e.g., in 2 major divisions of the MCA and their territories). An mTICI score of 2c means antegrade reperfusion of >90% but less than TICI 3 or near complete reperfusion. An mTICI score of 3 means full perfusion with filling of all distal branches.

It is noted, however, that other measures of cerebral scoring standards, such as expanded TICI (eTICI), other known and/or to-be-developed cerebral scoring standards, provide measures of cerebral scoring and are thus directly and/or indirectly applicable in understanding scope of the presently disclosed solution. eTICI scale is a 7-point compilation of TICI grades that reflects all previously reported thresholds used to define reperfusion after endovascular stroke therapy. For example, eTICI grade 0, just as mTICI, can be equivalent to no reperfusion or 0% filling of the downstream territory. eTICI 1 can indicate thrombus reduction without any reperfusion of distal arteries, including reperfusion of less than half or 1-49%. eTICI of 2b50 can be 50-66% reperfusion. eTICI 2b67 can be 67-89% reperfusion, exceeding TICI but below TICI2C. eTICI 2c can be equivalent to TICI 2C or 90-99% reperfusion. eTICI 3 can be complete or 100% reperfusion, such as TICI 3. It is understood that one of ordinary skill in the art can also correlate between currently known cerebral scoring standards and/or to-be-developed cerebral scoring standards (e.g., from mTICI to eTICI).

As discussed herein, "NIHSS Score" means The National Institutes of Health Stroke Scale, or NIH Stroke Scale (NIHSS) and is a tool used by healthcare providers to objectively quantify the impairment caused by a stroke. The NIHSS is composed of 11 items, each of which scores a specific ability between a 0 and 4. For each item, a score of 0 typically indicates normal function in that specific ability, while a higher score is indicative of some level of impairment. The individual scores from each item are summed in order to calculate a patient's total NIHSS score. The maximum possible score is 42, with the minimum score being a 0.

As discussed herein, "mRS" means the modified Rankin Scale (mRS) that is a commonly used scale for measuring the degree of disability or dependence in the daily activities of people who have suffered a stroke or other causes of neurological disability. The mRS scale runs from 0-6, running from perfect health without symptoms to death. An mRS score of 0 is understood as no symptoms being observed. An mRS score of 1 is understood as no significant disability is observed and the patient is able to carry out all usual activities, despite some symptoms. An mRS score of 2 is understood as slight disability and the patient is able to look after own affairs without assistance, but unable to carry out all previous activities. An mRS score of 3 is understood as moderate disability whereby the patient can require some help but is able to walk unassisted. An mRS score of 4 is understood as moderate severe disability and the patient is unable to attend to own bodily needs without assistance or walk unassisted. An mRS score of 5 is understood as severe disability and the patient requires constant nursing care and attention, bedridden, incontinent. An mRS score of 6 is understood as the patient being deceased.

As discussed herein, the term "safety", as it relates to a clot retrieval device, delivery system, or method of treatment refers to a relatively low severity of adverse events, including adverse bleeding events, infusion or hypersensitivity reactions. Adverse bleeding events can be the primary safety endpoint and include, for example, major bleeding, minor bleeding, and the individual components of the composite endpoint of any bleeding event.

As discussed herein, unless otherwise noted, the term "clinically effective" (used independently or to modify the term "effective") can mean that it has been proven by a clinical trial wherein the clinical trial has met the approval standards of U.S. Food and Drug Administration, EMEA or a corresponding national regulatory agency. For example, a clinical study may be an adequately sized, randomized, double-blinded controlled study used to clinically prove the effects of the reperfusion device and related systems of this disclosure. Most preferably to clinically prove the effects of the reperfusion device with respect to an ischemic event, for example, to achieve a clinically effective outcome in for the patient suffering the ischemic event (e.g., mRS less than or equal to 2) and/or achieve reperfusion the vessel(s) afflicted by the ischemic event.

As discussed herein, "sICH" is any extravascular blood in the brain or within the cranium associated with clinical deterioration, as defined by an increase of 4 points or more in the score on the NIHSS, or that leads to death and is identified as the predominant cause of the neurologic deterioration. For the purpose of this disclosure, subjects with sICH identified through all post-treatment scans up to the 24-hour time-point (including those performed due to clinical deterioration), were considered in the study discussed herein.

As discussed herein, the term "computed tomography" or CT means one or more scans that make use of computer-processed combinations of many X-ray measurements taken from different angles to produce cross-sectional (tomographic) images (virtual "slices") of specific areas of a scanned object, allowing the user to see inside the object without cutting. Such CT scans of this disclosure can refer to X-ray CT as well as many other types of CT, such as positron emission tomography (PET) and single-photon emission computed tomography (SPECT).

The present disclosure is related to systems, methods and devices restoring perfusion in blood vessels, and in particular clots from cerebral vessels. Certain features, such as a capture net, can be designed to trap a wide range of clot compositions inside the device, and an inner channel to stabilize the clot during retrieval. Certain feature of the retriever of this disclosure can allow the segments to remain open and opposed to the vessel wall while retracted through challenging vessels.

As an example, FIG. 1 depicts a schematic representation of the catheterization of a patient with a clot retrieval device 200, also known as a reperfusion device, via the femoral artery with a catheter 2. Example device 200 is a clinically approved FDA clot retrieval device that can restore blood flow in the neurovasculature by removing thrombus in patients experiencing ischemic stroke within 8 hours of symptom onset. However, it is understood that example device 200 could be used to restore blood flow in less than 8 hours of symptom onset (e.g., 6 hours) or up to 24 hours from symptom onset. As applicable procedure guidelines change with respect to the use of clot retrieval devices for treatment of ischemic events, it is also conceivable that device 200 could be used more than 24 hours from symptom onset. Device 200 can be understood as including features ore clearly described in Appendix 1 as incorporated by reference in its entirety from the U.S. Provisional applications from which this application claims priority, which includes U.S. Pat. Nos. 8,777,976; 8,852,205; 9,402,707; 9,445,829; and 9,642,639, each of which are incorporated by reference in their entirety as if set forth verbatim herein. Note that reperfusion devices can also be introduced through the wrist artery (radial access) or directly through the carotid artery. While both radial and carotid access avoids the aortic arches, there are other drawbacks. However, all three approaches are considered to be known to ones of skill in this art.

Figure 2:
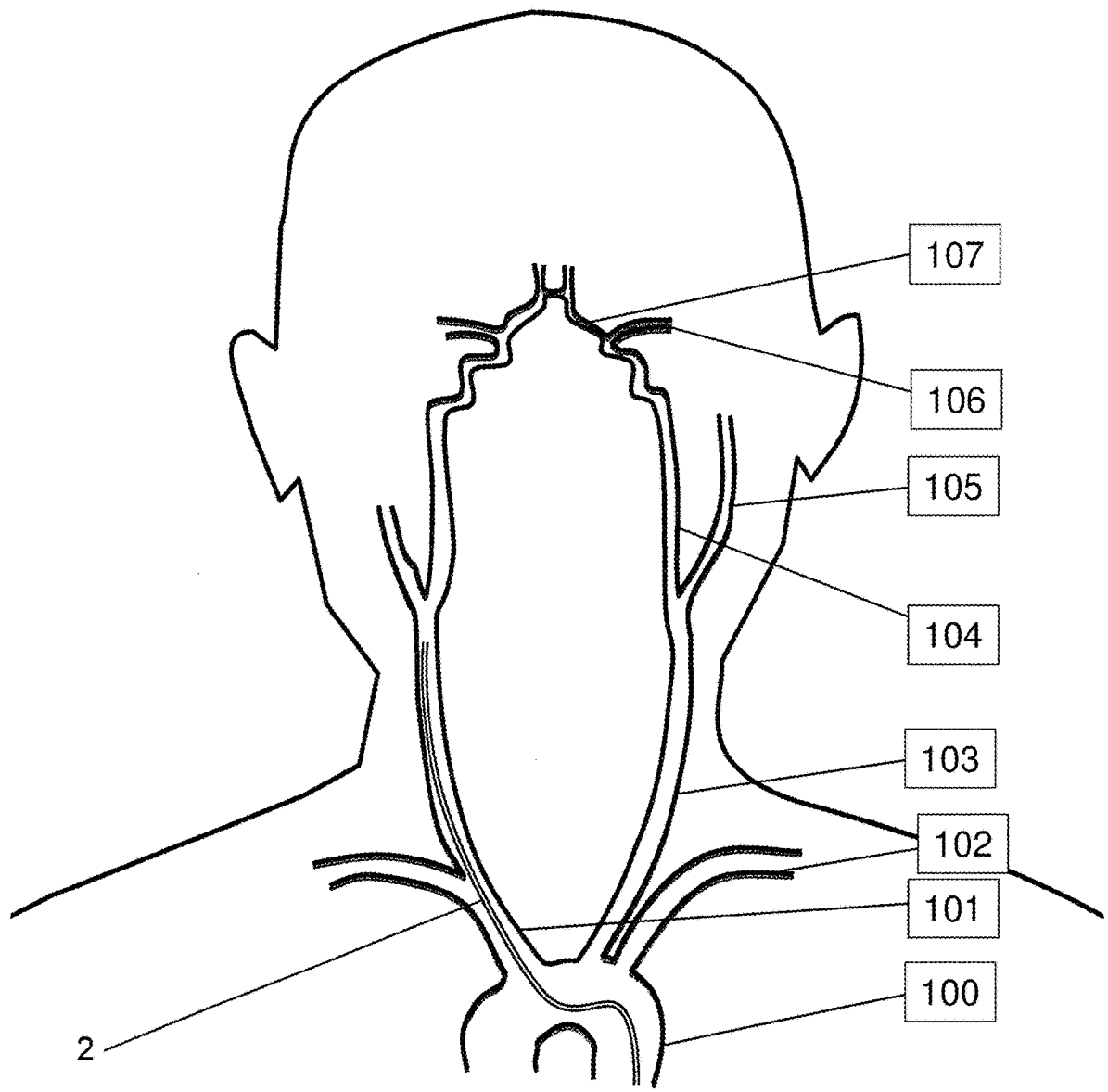
FIG. 2 shows certain anatomy of cerebral arteries above the aortic arch leading to the brain.

FIG. 2 shows a schematic representation of certain example cerebral vessels. Vessel 100 is the Aorta. Vessel 101 is the brachiocephalic artery. Vessel 102 is the subclavian artery. Vessel 103 is the common carotid artery. Vessel 104 is the internal carotid artery. Vessel 105 is the external carotid artery. Vessel 106 is the middle cerebral artery. Vessel 107 is the anterio-cerebral artery. The catheter 2 from FIG. 1 is shown with its distal end in the common carotid artery. In the more detailed drawings of the invention the details of the access site will not be shown but in general access and delivery is in accordance with FIGS. 1 and 2. Device 200 can be designed for use in the anterior and posterior neurovasculature in vessels such as the internal carotid artery, the M1 and M2 segments of the middle cerebral artery, the vertebral artery, and the basilar arteries. Device 200 can be delivered endovascularly under fluoroscopic guidance in a similar manner to that of other neurovascular clot-retrieval systems.

Figure 3:
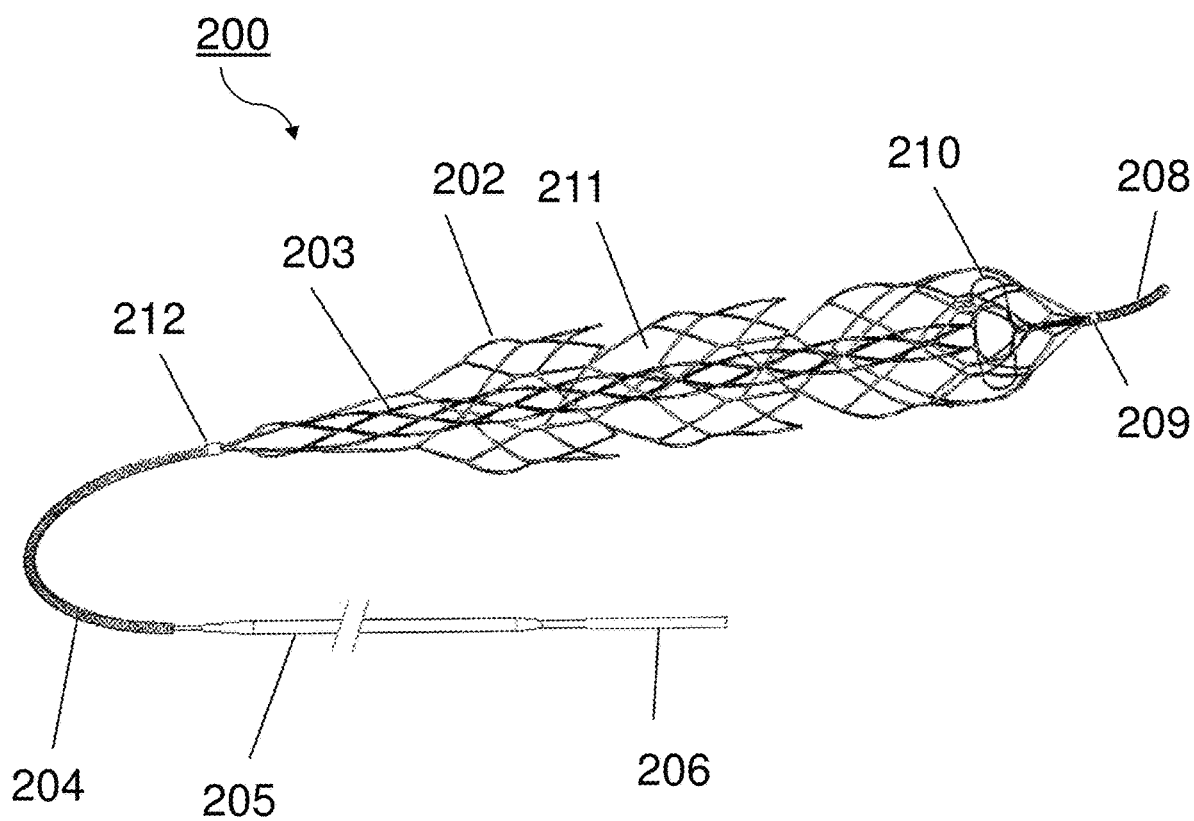
FIG. 3 shows an isometric view of an example stent retriever device of this disclosure.

Once across the site of vessel occlusion, the stent-like element of device 200 is deployed to entrap the clot and allow it to be retrieved, hence restoring blood flow. Device 200 can be a dual-layer stent retriever, with articulating petals, and a distal capture zone for effectively trapping, retaining, and removing various clot types to restore blood flow in patients with AIS secondary to large-vessel occlusion. Examples of the device 200 can be available in two lengths, 5×21 mm and 5×33 mm. It is understood that device 200 of this disclosure would be used with a delivery system to the site of the clot, including a guide catheter, a microcatheter, and/or a guidewire. It is also contemplated that device 200 of this disclosure could be used in connection with an aspiration system to further facilitate restoring perfusion to the vasculature. FIG. 3 shows one embodiment of an example clot retrieval device of this disclosure. Device 200 can have an elongate shaft 206. Shaft 206 can have a distal end that extends interior of the artery and a proximal end that extends exterior of the artery. Shaft 206 can also have a clot engaging portion configured at its distal end having an outer expandable member 202 and an inner expandable member 203 to facilitate restoration of blood flow through the clot after device 200 is deployed. Members 202 and 203 can be configured to have a collapsed configuration for delivery and an expanded configuration for clot retrieval, restoration of perfusion, and fragmentation protection in general.

Shaft 206 may be a tapered wire shaft, and may be made of stainless steel, MP35N, Nitinol or other material of a suitably high modulus and tensile strength. Shaft 206 has a coil 204 adjacent its distal end and proximal of the outer member and inner tubular member. The coil may be coated with a low friction material or have a polymeric jacket positioned on the outer surface. Sleeve 205 may be positioned on shaft 206 adjacent coil 204. Sleeve 205 may be polymeric and may be positioned over the tapered section of shaft 206.

The outer member 202 is configured to self-expand upon release from a microcatheter to a diameter larger than that of the inner tubular member 203. Expansion of the outer member 202 causes compression and/or displacement of the clot during expansion for purposes of restoring perfusion to the vessel. A radiopaque coil 208 (which may be platinum or gold or an alloy of same) is positioned over the distal end of member 203 and butts against the distal collar 209 of the outer member 202, where it is connected by an adhesive joint to the collar 209. In some examples, the distal end of device 200 at or adjacent collar 209 can be closed by way of struts 210 being joined. In some examples, the outer member 202 can have a closed distal clot capture structure whereby a plurality of struts converge at a terminal connection. In some examples, the distal end of the outer member 202 can have its struts terminate at a distal end in a junction to define a closed end that can prevent egress of clot (or clot fragments that have entered thereof) between the inner 203 and outer 202 members. Inlet openings of outer member 202 can provide the primary movement freedom available to the clot and so the expansion of the outer member 202 urges the clot into the reception space 211 and outer member 202 can have multiple inlet mouths to accept the clot. Optionally expanded distal struts 210 can be included with the inner member 203 and function as an additional three-dimensional filter to prevent the egress of clot or clot fragments.

Study Overview

This disclosure is more clearly understood with two corresponding studies discussed more particularly below with respect to treatment of ischemic stroke, each of which is in Appendices 2-4, each incorporated by reference in their entirety as if set forth verbatim herein from the U.S. Provisional applications from which this application claims priority. It is understood that data is presented herein for purposes of illustration and should not be construed as limiting the scope of the disclosed technology in any way or excluding any alternative or additional embodiments.

In each study, device 200 was prepared for delivery to the occlusion site with standard interventional techniques to access the arterial system and using angiography in order to determine the location of the occluded vessel. Once determined, a guide catheter, sheath, or balloon guide catheter was advanced as close to the occlusion as possible. A rotating hemostasis valve (RHV) was connected to the proximal end of the catheter and connected to a continuous flush system. An appropriate microcatheter was then selected and an RHV was connected to the proximal end of the microcatheter and connected to a continuous flush system. With the aid of a suitable guidewire, and using standard catheterization techniques and fluoroscopic guidance, the microcatheter was advanced up to and across the occlusion so that the distal end of the microcatheter is positioned distal of the occlusion. The guidewire was removed from the microcatheter and optionally contrast media was gently infused through the microcatheter to visualize the distal end of the occlusion. The insertion tool with the preloaded retrieval device 200 was then removed from the packaging hoop. The distal end of the insertion tool was inserted through the RHV of the microcatheter and then waited until fluid was seen exiting the proximal end of the insertion tool, confirming that device 200 was flushed. The insertion tool was then advanced until it contacted the hub of the microcatheter and the RHV was fully tightened to hold the insertion tool securely in position. The insertion tool was confirmed as being fully seated in the hub of the RHV before proceeding to advance device 200 until at least half of the shaft length of shaft 206 was inserted into the microcatheter, at which point the insertion tool was removed.

Regarding positioning and deployment, device 200 continued to be advanced towards the distal tip of the microcatheter (e.g., until the distal radiopaque tip 208 of the device 200 was aligned with the distal tip). Device 200 optionally included bands positioned on the proximal portion of shaft 206 to assist in minimizing the amount of fluoroscopic exposure required during insertion of device 200. If using a standard microcatheter (total length of 155 cm and a 7 cm RHV), then when the first band on the shaft 206 approached the RHV, while the tip of device 200 was approximately 8 cm from the distal end of the microcatheter. When the second band on the shaft 206 approached the RHV, the tip of device 200 was nearing the distal end of the microcatheter. Device 200 was then advanced in the microcatheter and positioned within the clot and left to embed for 3-5 minutes prior to withdrawal.

Device 200 was optionally supplied preloaded within an insertion tool. In such applications, the physician inserted the insertion tool into the hub of a pre-positioned microcatheter and advances the clot retrieval device forward out of the insertion tool and into the microcatheter.

Figure 4:
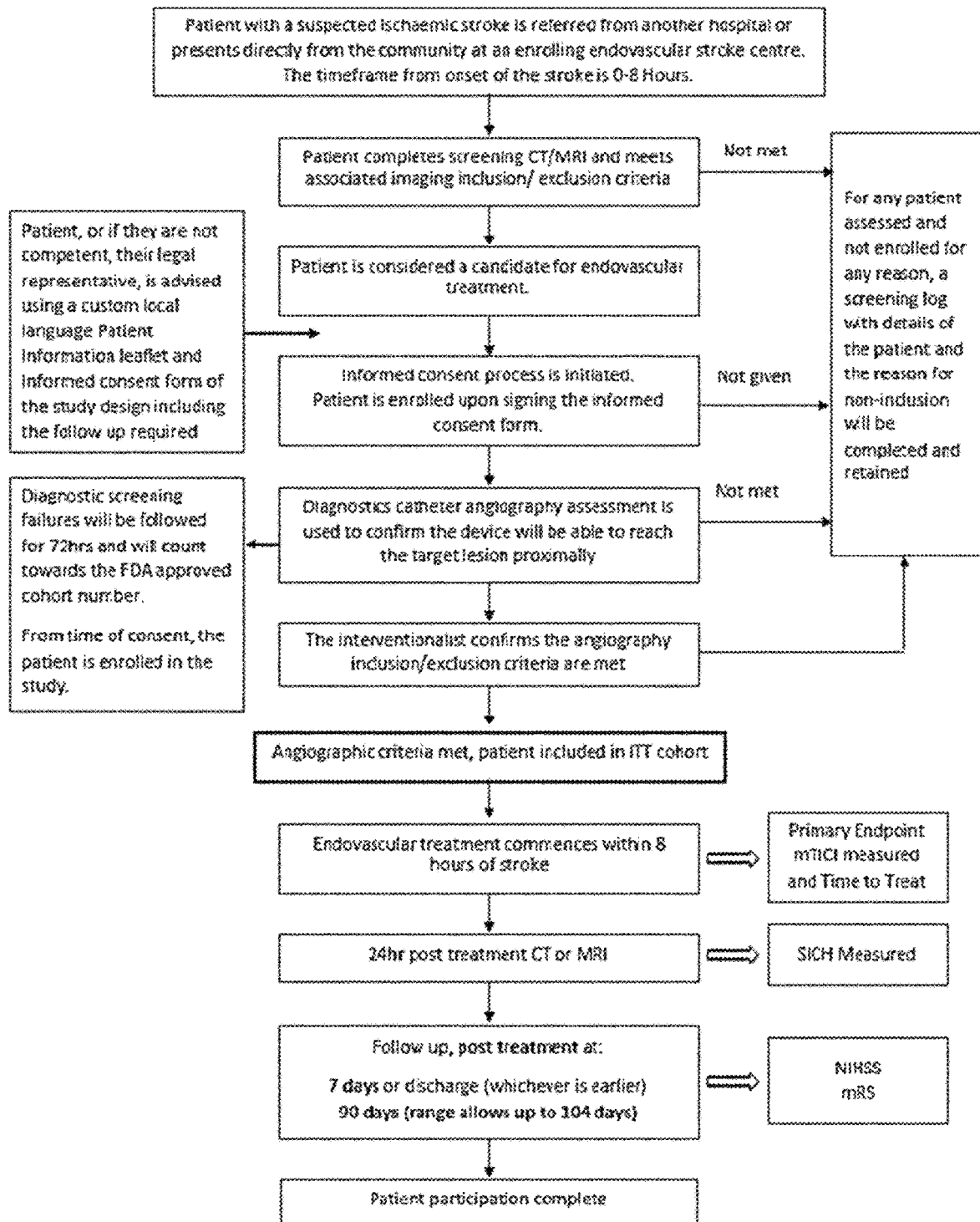
FIG. 4 shows a representative overview of an example of a study flow used for this disclosure.

During each study, device 200 tested was typically used for up to three (3) retrieval attempts. If an additional pass was made with device 200, then any captured thrombus was carefully removed therefrom, and device 200 cleaned in heparinized saline. FIG. 4 of this disclosure shows a representative overview of the study flow using the patients of each study with the clot retrieval device 200.

Patients associated with each study included those with acute ischemic stroke in anterior circulation (including distal internal carotid artery (ICA), carotid T, middle cerebral artery (MCA) segments M1 and M2) treated with endovascular treatment using the stent retriever of this disclosure as first or second line device, were retrospectively included across multiple different centers. According to the availability of the material, there were not any recommendation regarding a preferred type of stent retriever, the clot retrieval device of this disclosure was used randomly in the flow of patients.

Patient Selection

For each included patient, age, gender and cardiovascular risk factors (e.g., diabetes mellitus, obesity, smoking, high blood pressure, hyperlipidemia) were recorded. Initial imaging was brain CT with cervical and intracranial angiography or brain MRI with time of flight angiography, depending on hospital protocol. The ASPECT (Alberta Stroke Program Early CT) score was evaluated by experienced neuroradiologists on either modality, and the NIHSS score by neurologists. Patients were treated up to 12 hours from time of stroke onset or time last known well in case of wake-up stroke.

All patients with confirmed large-vessel occlusion and no hemorrhage on noncontrast CT were treated with the clot retrieval device 200 of this disclosure. If patients arrived within 4.5 hours of stroke onset, IV tPA was administered with a dosage of 0.9 mg/kg of body weight unless contraindicated. Access techniques, including the use of balloon guide catheters, the use of intermediate catheters, and co-aspiration techniques, were left to the discretion of the physician. Typically, a 0.014 inches guidewire and a 0.021 inches microcatheter were advanced through the clot, the guidewire was then removed and device 200 of this disclosure, including one with porous expandable inner and outer bodies measuring one of two lengths, 5×21 mm and 5×33 mm, was advanced through the microcatheter and positioned as distal as possible with the start of the outer cage body aligned with the proximal face of the occlusion. Some operators waited for at least 3 minutes for embedding, while other times the device 200 was retracted into an intermediate or guide catheter without any additional waiting time. The device 200 was used as first-line or second-line device (in only those cases where another first-line device failed to recanalize), and the number of attempts using the device 200 were also left to the discretion of the treating physician The study objective was to examine the recanalization efficacy of the clot retrieval device of this disclosure, associated performance characteristics and clinical outcomes in patients with AIS compared with a performance goal (PG) established by a meta-analysis derived composite endpoint based on other clot retriever devices, Solitaire® and Trevo®.

In the first study, successful achievement of the endpoint was achieving a mTICI score of ≥2b or greater in the target vessel, following 3 or less passes of device 200. In the second study, the primary endpoints for successful recanalization were after one or two attempts of the device 200, defined by the modified mTICI score ≥2b, and successful recanalization independently of the number of attempts. Revascularization was also measured using mTICI of a 2c rating. The mTICI score was evaluated at the end of the procedure by the neuroradiologist who performed the intervention.

When a second clot retrieval device followed the initial device 200, recanalization was considered to be futile (i.e., mTICI<2b). Other endpoints in each study included evaluation of procedural efficacy for successful recanalization of all patients including those treated with a second clot retrieval device, and positive good clinical outcome as defined by a modified Rankin Score (mRS) ≤2 at 3 months.

The primary safety endpoint observed in each study was the rate of Symptomatic Intracerebral hemorrhage (sICH) together with any Serious Adverse Device Effects (SADEs) (excluding those already counted in sICH). It is known to those of skill in the art that the term "rate" is intended to refer to the rate for a particular population of patients according to a particularly clinical investigation rather than information or levels related to a single patient. However, herein the term "rate" and "level" can be used interchangeably. In any study, single patient levels are used to determine "rates". Any one patient's level may be the notable point in a reported rate. Safety was also assessed by recording procedural complications: distal embolism to previously unaffected territory, vessel perforations, vasospasms, and intracranial hemorrhage (ICH). ICH was determined on a CT control at 24 hours, and included all types of hemorrhagic transformations (HI1, HI2, PH1, PH2), and defined as symptomatic if associated with a worsening of the NIHSS score ≥4 points at day 1, as per ECASS-3 criteria. The primary safety endpoint was measured as the occurrence of within 24 hours (−8/+12 hrs) post-procedure, together with any other Serious Adverse Device Effects (excluding those already counted in sICH). Secondary endpoints included an mRS score of ≤2 at 90(+/−14) days.

Neurologic evaluation in each study was performed through repeat NIHSS determinations in line with standard of care at 24 hours (−8/+12 hours) and at 7 days (or discharge whichever is sooner) time points post-procedure. An additional NIHSS score was obtained when any signs of neurologic deterioration occur or in the event of an ICH to assess the degree of deterioration. A certified examiner performed all neurologic evaluations and the 90-day evaluation was used to record the mRS score.

Inclusion criteria for each study included the following:
Aged between 18 years and 85 years (inclusive).
A new focal disabling neurologic deficit consistent with acute cerebral ischemia.
NIHSS score ≥8 and ≤25.
Pre-ictal mRS score of 0 or 1.
The interventionalist estimates that at least one deployment of device 200 can be completed within 8 hours from the onset of symptoms.
Patients for whom IV-tPA is indicated and who are available for treatment, are treated with IV-tPA.
IV-tPA, if used, was initiated within 3 hours of stroke onset (onset time is defined as the last time when the patient was witnessed to be at baseline), with investigator verification that the subject has received/is receiving the correct IV t-PA dose for the estimated weight.
Angiographic confirmation of an occlusion of an ICA (including T or L occlusions), M1 or M2 MCA, VA, or BA with mTICI flow of 0-1.
For strokes in the anterior circulation, either MRI criterion of volume of diffusion restriction visually assessed ≤50 mL or CT criterion: ASPECTS 6 to 10 on baseline CT or CTA-source images, or, volume of significantly lowered CBV≤50 mL.
The patient is indicated for neurothrombectomy treatment by the interventionalist and it is confirmed by diagnostic angiography that the device will be able to reach the target lesion proximally.
Exclusion criteria for each study included the following:
Life expectancy likely less than 6 months.
Females who were pregnant or breastfeeding.
History of severe allergy to contrast medium.
Known nickel allergy at time of treatment.
Known current use of cocaine at time of treatment.

Patient has suffered a stroke in the past 3 months.

The patient presents with an NIHSS score <8 or >25 or is physician assessed as being in a clinically relevant uninterrupted coma.

Subject participating in another study involving an investigational device or drug.

Use of warfarin anticoagulation or any Novel Anticoagulant with International Normalized Ratio (INR)>3.0.

Platelet count <50,000/μL.

Glucose <50 mg/dL.

Any known hemorrhagic or coagulation deficiency.

Unstable renal failure with serum creatinine >3.0 or Glomerular Filtration Rate (GFR)<30.

Patients who received a direct thrombin inhibitor within the last 48 hours; must have a partial thromboplastin time (PTT) less than 1.5 times the normal to be eligible.

All patients with severe hypertension on presentation (SBP>220 mmHg and/or DBP>120 mm Hg). All patients, in whom intravenous therapy with blood pressure medications is indicated, with hypertension that remains severe and sustained despite intravenous antihypertensive therapy (SBP>185 mmHg and/or DBP>110 mmHg).

Known cerebral vasculitis.

Rapidly improving neurological status.

Clinical symptoms suggestive of bilateral stroke or stroke in multiple territories.

Ongoing seizure due to stroke.

Evidence of active systemic infection.

Known cancer with metastases.

Computed tomography (CT) or Magnetic Resonance Imaging (MRI) evidence of recent/fresh hemorrhage on presentation.

Baseline computed tomography (CT) or MRI showing mass effect or intracranial tumor (except small meningioma).

Suspicion of aortic dissection, presumed septic embolus, or suspicion of bacterial endocarditis.

Stenosis, or any occlusion, in a proximal vessel that requires treatment or prevents access to the site of occlusion.

Evidence of dissection in the extra or intracranial cerebral arteries.

Occlusions in multiple vascular territories (e.g., bilateral anterior circulation, or anterior/posterior circulation).

Results of the First Study

In the first study, 80 patients (44 men and 36 women; median age 72 years; range, 34-93 years) were treated with device 200 from June 2015 to December 2016. Baseline characteristics of the first study are also summarized in FIG. 5 while intra-procedural characteristics are summarized in FIG. 6. Median NIHSS at admission was 15 (range 5-30) and median initial ASPECT score was 8 (1-10). Occlusion was proximal i.e. from the ICA in 19 cases (23.7%) and involved the MCA (M1, M2) in 79 cases (99%). 7 patients (9%) had tandem (proximal ICA) occlusions. Forty-five patients (56.2%) received IV tPA before EVT. The median time from symptom onset to groin puncture was 198 min (range 60 min to 630 min). The median time from symptom onset to recanalization was 238 min (range 104 min to 685 min). The median procedure time from groin puncture to recanalization was 35 min (range 8 min to 161 min). The number of thrombectomy attempts ranged from 1 to 9 with a median of 1.

Device 200 in the first study was used as a first line device in 78 out of 80 (97.5%) cases among which a second device was used in 10 cases (12.5%). Outcomes of the first study are summarized in FIG. 7, whereby successful recanalization was achieved with device 200 alone in 81.3% (n=65) of patients (56% mTICI 3, 25% mTICI 2b), and within 1 or 2 passes in 61.3% (n=49) of patients (50% mTICI 3, 11.3% mTICI 2b). Almost half (n=39, 48.8%) of all patients were successfully recanalized in one pass (42.5% mTICI 3, 6.3% mTICI 2b). For the entire series, including use of a second device, the rate of successful recanalization was 90% (n=72). The mRS outcome at 3 months was available for 78 patients and is summarized in FIG. 8. It can be seen that 2 patients were lost to follow-up and among the 78 patients, 49 (62.8%) had an mRS≤2. Median mRS at 3 months was 2. During the procedure, distal emboli in previously unaffected arterial territories were found in 5 (6.3%) cases, no vessel perforations, and 3 vasospasms (3.8%). Intracranial hemorrhage on CT at day 1 was found in 17 (21.3%) cases and among them 76.5% have received IV tPA before EVT, none of them were subarachnoid hemorrhages, and 5 were symptomatic (6.3%).

In the first study, a balloon guide catheter was used in 37 (46%) patients (BGC group), and was associated with better complete recanalization rates of mTICI 3 (76% vs 49%, p=0.021), faster groin to revascularization time (26.7 min vs 54.7 min, p<0.0001), and higher rates of good clinical outcome of mRS≤2 (78% vs 47%, p=0.004). Analysis of balloon guide catheter technique is summarized in FIG. 9

Figure 8:
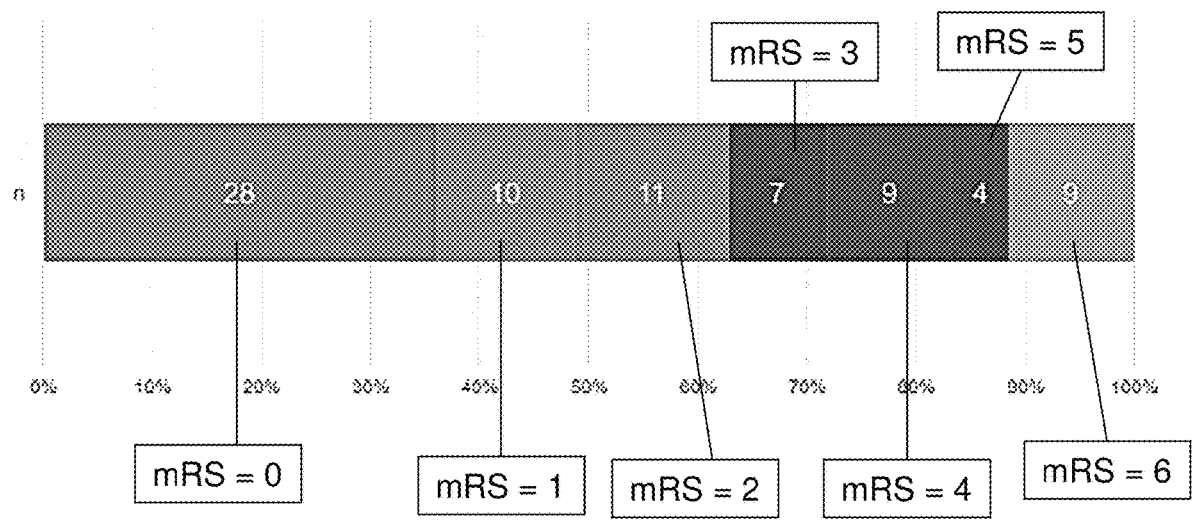
FIG. 8 depicts clinically effective outcomes ranging from mRS 0-6 in the first study of this disclosure.

Successful recanalization (mTICI 2b or greater) in the first study was 81.3%, with a high rate of success within 1 or 2 passes (61.3%). Compared to similarly designed real-world (non-clinical trial) series where mTICI 2b-3 rates of all patients including those treated with rescue techniques is generally reported, the overall successful revascularization rate in our series was 90%. Furthermore, higher good clinical outcomes (evaluable in 78 out of 80 patients) were observed, defined as mRS≤2 in 62.8% of patients, as depicted in FIG. 8 in comparison to prior known devices. Compared to a similarly designed study of 34 patients using the ERIC device (successful recanalization in 79%, good clinical outcomes in 48%) (10), device 200 of the first study had fewer tandem (9% vs 26%) and terminal ICA occlusions (25% vs 32%), which are known to have worse clinical outcomes. See Raoult H, Redjem H, Bourcier R, Gaultier-Lintia A, Daumas-Duport B, Ferré J C, et al. *Mechanical thrombectomy with the ERIC retrieval device: initial experience*. Journal of NeuroInterventional Surgery. 2016; neurintsurg-2016-012379.

Figure 10:
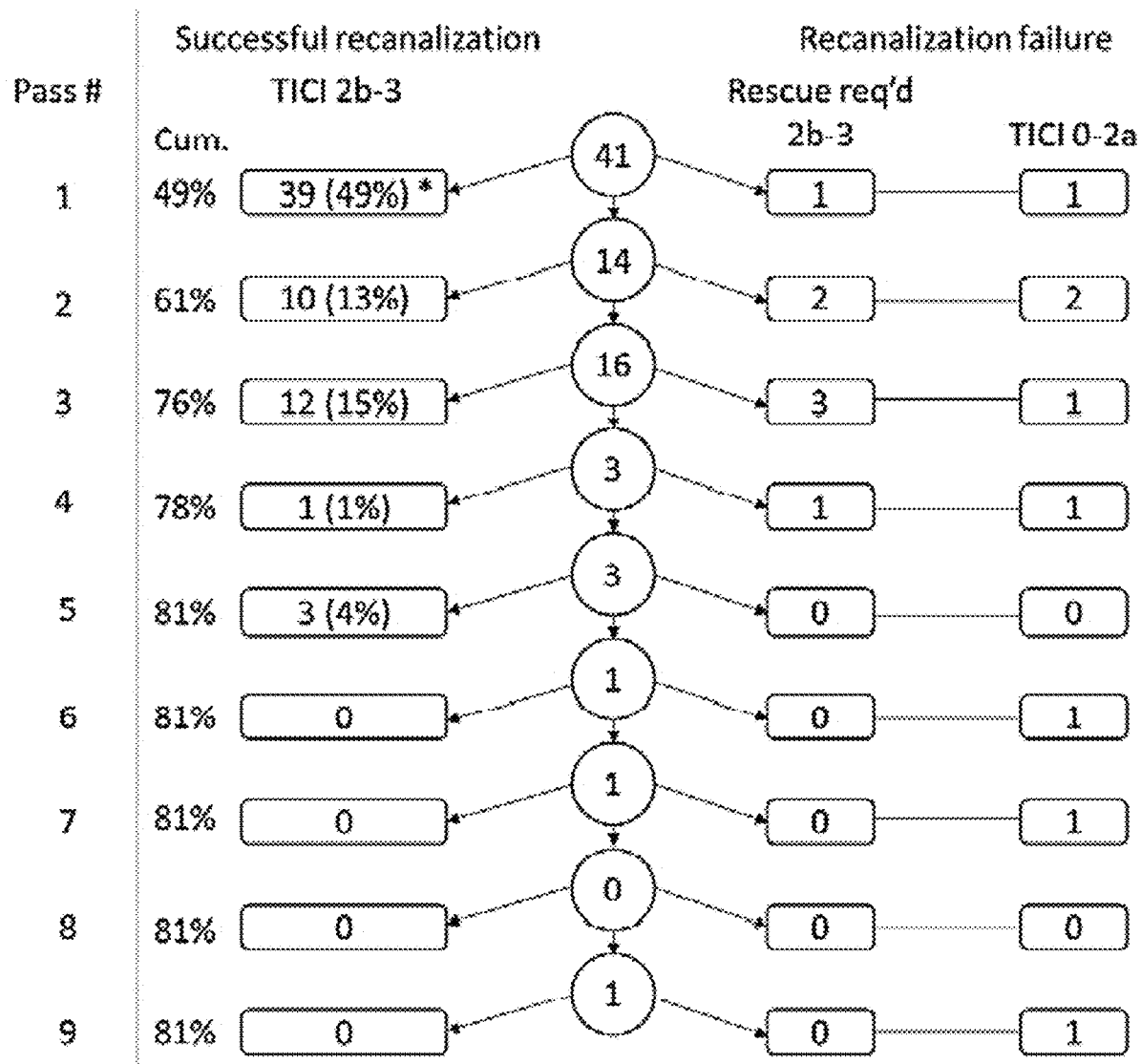
FIG. 10 depicts a summary of recanalization by pass for the first study of this disclosure.
Figure 11:
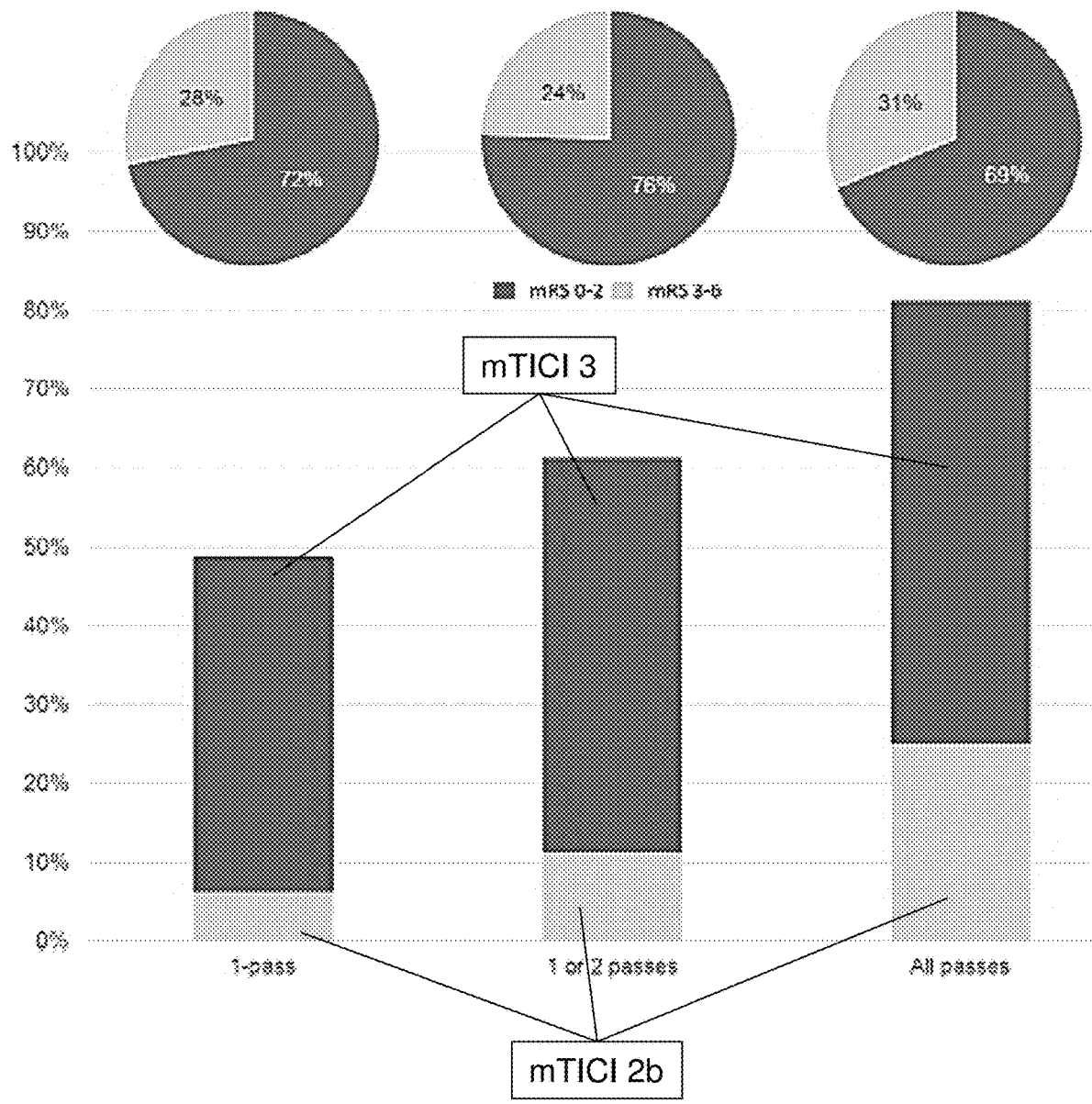
FIG. 11 depicts functional and clinical outcomes by pass for the first study of this disclosure.

In 48.8% of patients, successful recanalization was achieved in 1 pass, with majority achieving complete revascularization mTICI 3 (42.5%) compared to mTICI 2b (6.3%). Subsequent passes allowed for more recanalization, which tended towards a maximum benefit at 3 passes, as shown in FIG. 10 which summarizes recanalization by pass for the first study. In particular, the circle in the center of FIG. 10 represents the number of patients completed after each attempt. Under successful recanalization, there is a cumulative percentage (CUM %) shown to the left. Under recanalization failure, the 7 cases in which mTICI 2b-3 was achieved with the use of a second stent-retriever (rescue required) is shown as a failure. In our series, 71.8% of patients that achieved mTICI 2b-3 in 1 pass had successful outcomes as shown in FIG. 11. In FIG. 11, successful recanalization with device 200 is a pie chart (mTICI 3 and mTICI 2b separately), describing percentage of good clinical outcomes (mRS 0-2) for patients. 61.2% of patients were successfully revascularized with device 200 alone in 1 or 2 passes.

Moreover, in comparison to the same earlier mentioned ERIC study, device 200 in the first study had a shorter time from symptom onset to femoral puncture (median 198 min vs 242 min). Device 200 in the first study was also used with local aspiration (54%) or balloon guide catheter (46%), and sometimes (3%) both. Emboli were observed in previously unaffected territory in 6.3% of cases, no vessel perforations, and vasospasms in 3.8%. Intracranial hemorrhage was observed in 17 (21.3%) patients at 24-hours, none of them were subarachnoid hemorrhages, and 5 were symptomatic (6.3%).

Results of the Second Study

In the second study, primary endpoints for successful recanalization were after one or two attempts of the device 200, defined by the modified Thrombolysis in Cerebral Infarction (mTICI) score ≥2b, and successful recanalization independently of the number of attempts. Revascularization was also measured using modified Thrombolysis in Cerebrovascular Infarction (mTICI inclusive of the 2c rating). Successful achievement of the endpoint is defined as achieving a mTICI score ≥2b in the target vessel, following 3 or fewer passes of the clot retrieval device 200 of this disclosure.

Figure 12:
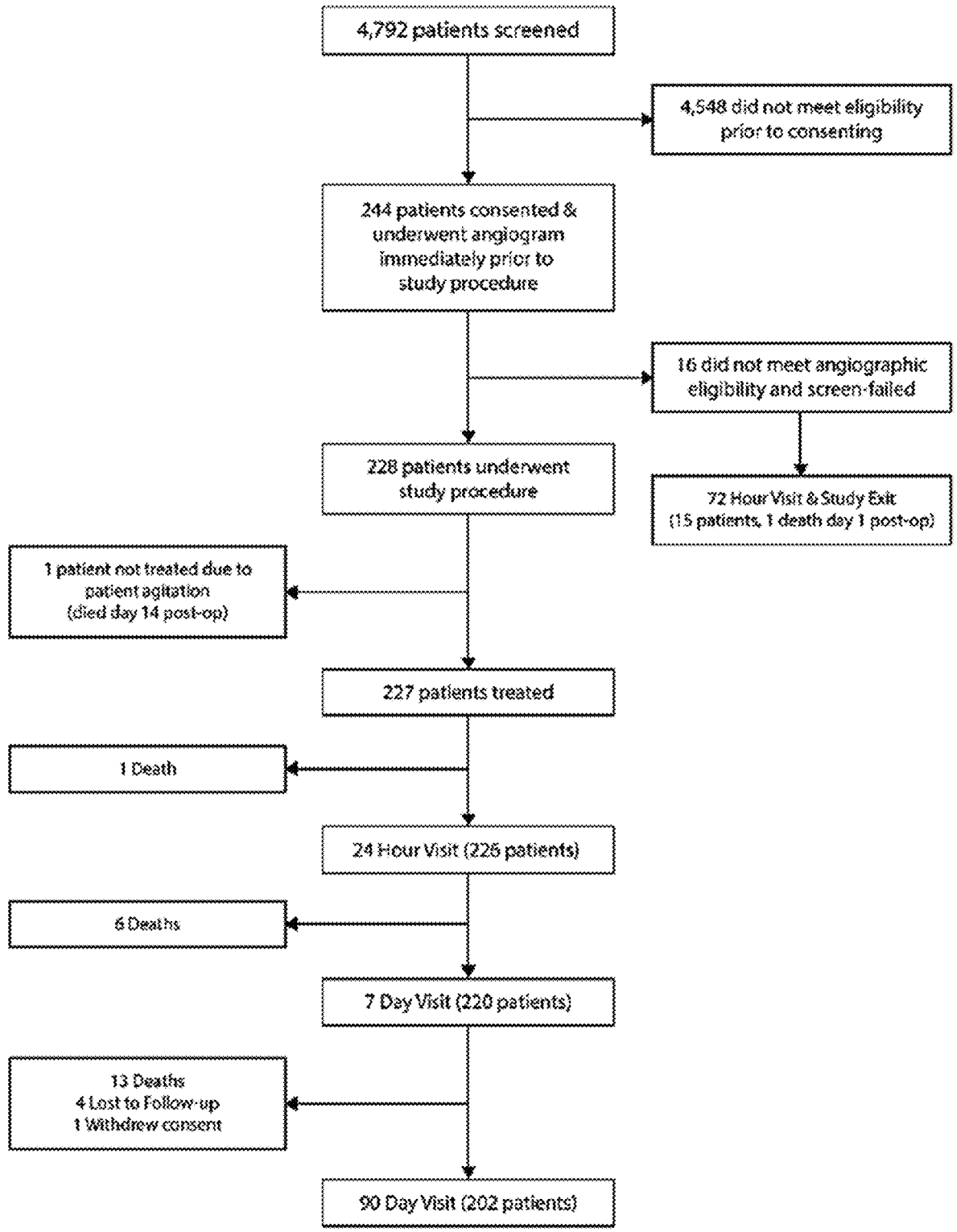
FIG. 12 reproduces an example of data for selecting patients for the second study for this disclosure.

FIG. 12 depicts a representative overview of patient selection data from the second study for this disclosure. Baseline characteristics of the second study are also summarized in FIG. 13. The second study included 176 evaluable patients with up to 228 patients allowed in the event the data is needed to compensate for "roll in" patients, missing or censored outcome data, patient withdrawal, or too small a mITT (modified Intention-To-Treat) population to test the primary endpoint for the hypothesis as designed. As noted elsewhere, the mITT can be configured based on requirement of the study as well as reviewing agencies. The mean age was 68±13 years, 45.8% were men, and the mean baseline NIHSS was 15.8±5. The median interquartile range baseline ASPECT score was 10. Anterior circulation occlusion was encountered in 96% of patients, the most common location being the middle cerebral artery, M1 (55.5%) and M2 (25.1%), followed by internal carotid artery occlusion (15.4%). Over half of the patients (52.9%) received intravenous tPA. A balloon guide catheter was used in 73.6% of patients. The Surveillance, Epidemiology, and End Results (SEER) and HERMES individual patient data pooled analyses reported final mTICI≥2b rates of 71.1% and 71%, respectively, whereas the second study for device 200 of this disclosure reported rates of 80% (within 3 passes) and 92.5% at the end of the procedure. See Goyal M, Menon B K, van Zwam W H, Dippel D W, Mitchell P J, Demchuk A M, et al; *HERMES Collaborators. Endovascular thrombectomy after large-vessel ischaemic stroke: a meta-analysis of individual patient data from five randomised trials*. Lancet. 2016; 387:1723-1731. doi: 10.1016/S0140-6736(16) 00163-X As stated, the objective of the second study was to investigate the performance of the device 200 against a performance goal for efficacy ($PG_{efficacy}$). In order to claim non-inferiority against an efficacy driven performance goal, the lower bound of a (95%) confidence interval was necessary to be greater than a non-inferiority limit (NL) which was the predetermined $PG_{efficacy}$. The Performance Goal (PG) was calculated using a Bayesian Hierarchical Random Effects Meta-Analysis which incorporates a down-weighting of the Merci data by treating patients from the Trevo® and Solitaire® trials only as exchangeable. The test for performance was based on a one-sided test (at the 0.025 significance level) for a binomial proportion with hypotheses, as follows:

$$H_0: PG_{efficacy} \leq N_L \text{ versus } H_1: PG_{efficacy} > N_L$$

The sample size of 176 revascularization results was needed in order to have 90% power to demonstrate non-inferiority against a non-inferiority limit ($N_L$) with an efficacy level of 0.56, based on a one-sided exact test for a binomial proportion at the 0.025 significance level and assuming that the proportion of adjudicated successes with the device 200 was 0.68.

Descriptive statistics were used to summarize the clinical outcome variables collected on all vessels treated in this investigation overall. The typical value for each continuous response variables were estimated using the mean and median while the variability was estimated using the range, interquartile range and standard deviation. All categorical variables were reported as counts and percentages. Box and bean plots will be generated for each continuous response variables while bar charts will be generated for each categorical variable. At study completion summaries of each clinical outcome variable include corresponding 95% confidence intervals in order to provide an estimate of the corresponding population means, medians and proportions.

FIG. 14 is a table summarizing angiographic and clinical outcome results for device 200 in connection with the investigation of this disclosure. As can be seen, the primary efficacy endpoint in the second study with device 200 (mTICI≥2b within 3 passes) was observed as 80.2% (95% confidence interval, 74%-85% versus 56% performance goal criterion; P value, <0.0001), and mTICI≥2c was 65%. After all interventions, mTICI≥2c was achieved in 76%, and mTICI≥2b was 92.5%, which was a significant improvement over 88% seen in the SWIFT trial (i.e. approximately a 5% improvement from the closest comparable clinical data).

The rate of first pass (mTICI≥2b following a single pass with device 200) was 51.5%. The primary safety endpoint composite rate of symptomatic intracerebral hemorrhage or serious adverse device effects was 5.3%. Functional independence and all-cause mortality at days were observed at 67% and 9%, respectively. Device 200 also showed favorable performance on several measures indicating faster or more complete reperfusion, beyond successful reperfusion (mTICI, ≥2b). FP successful reperfusion (mTICI, ≥2b) was achieved in 50% and FP excellent reperfusion (mTICI, ≥2c) in 4 of every 10 patients and these rates compared favorably to prior devices, including the Solitaire and Trevo device. Device 200 also showed high rates of mTICI≥2c in 64.8% of patients within 3 passes.

FIG. 15 is a table summarizing angiographic and clinical outcome results for device 200 in connection with the investigation of this disclosure. Functional independence (mRS, at 90 days was achieved in at least approximately 67% (146/217; 95% CI, 61%-73%).

Figure 16:
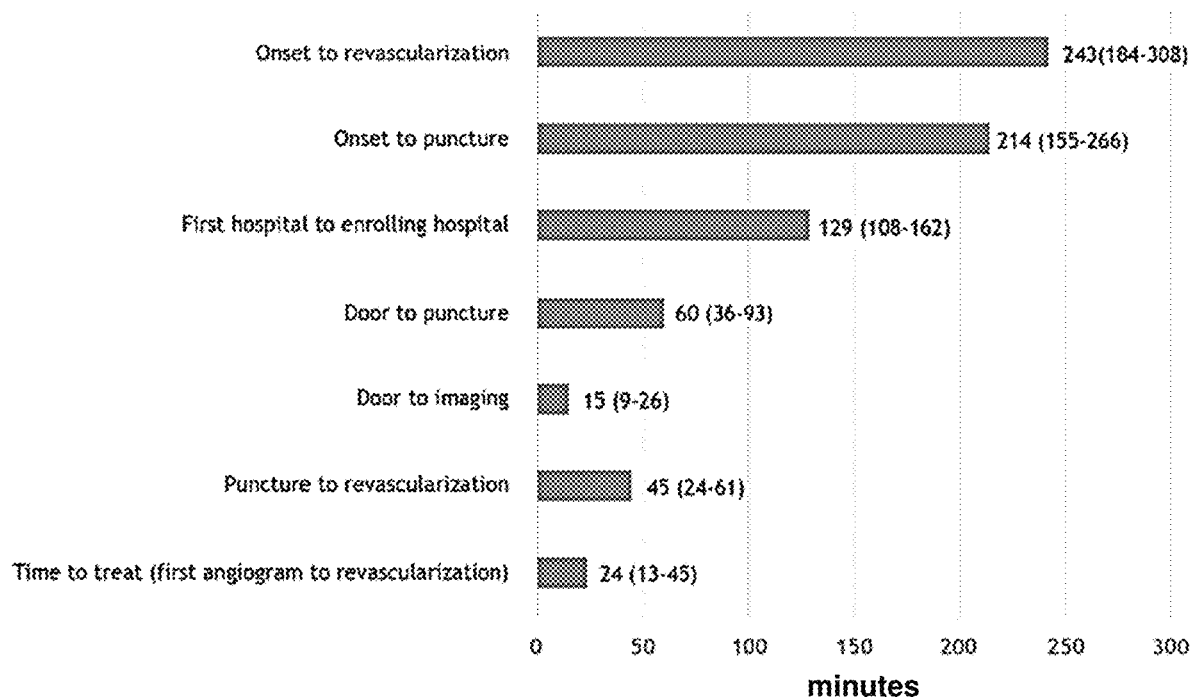
FIG. 16 depicts work-flow time metrics in minutes, median interquartile range for the study of this disclosure.

FIG. 16 depicts work-flow time metrics minutes. It is understood that time from puncture to revascularization was time to modified thrombolysis in cerebral ischemia (mTICI) ≥2b or final angiogram (for those who did not achieve mTICI≥2b) minus puncture time. The median time from symptom onset/last known well to puncture was 214 (IQR—interquartile range, 155-266) minutes and door-to-puncture was 60 (IQR, 36-93) minutes.

Figure 17:
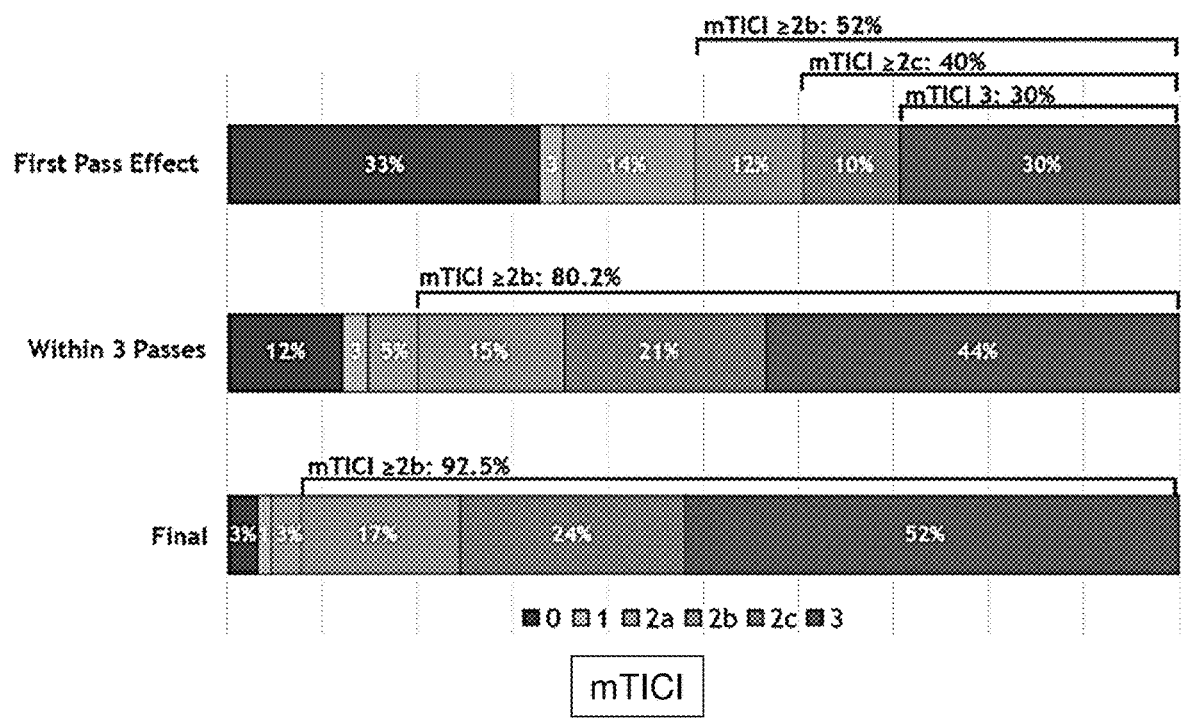
FIG. 17 depicts an overview of revascularization in ischemic stroke with the retrieval device of this disclosure at 90-day clinical outcome for the study of this disclosure.

FIG. 17 depicts a summary of revascularization in ischemic stroke with device 200 of this disclosure at 90-days under the mRS distribution. Neurological deterioration by ≥4 NIHSS points at 24 hours occurred for device 200 at 4.5% (95% CI, 2%-9%). Procedure-related mortality rate at day 7 was 0% and all-cause mortality at day 90 was 9% (95% CI, 6%-14%). The device 200 achieved the primary efficacy end point of successful reperfusion (mTICI≥2b within 3 passes and without use of rescue therapy) in 182 of 227 (80.2%; 95% CI, 74%-85%) and demonstrated superiority to the pre-set PG criterion of 56% for efficacy (P value, <0.0001. see also FIG. 14). The rate of mTICI≥2c reperfusion within 3 passes of the device of this disclosure was 64.8%.

Figure 18:
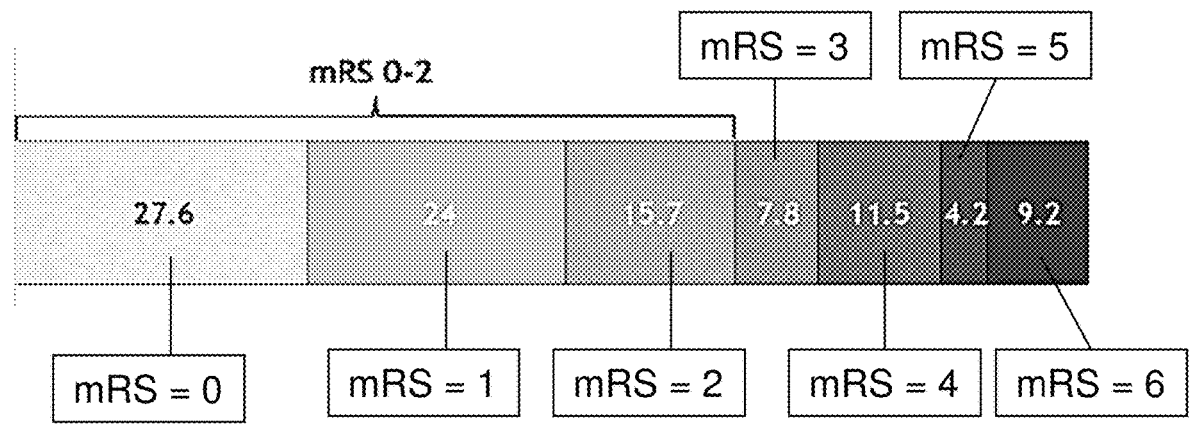
FIG. 18 depicts clinically effective outcomes ranging from mRS 0-6 for the second study of this disclosure.

The full distribution of procedure outcomes is shown in FIG. 18. FP effect (mTICI≥2c after a single pass) was seen in 91 of 227 (40.1%) and modified FP effect (mTICI≥2b after a single pass) was seen in 117 of 227 (51.5%) patients. Final angiographic reperfusion rates after all interventions were 92.5% mTICI≥2b, 75.8% mTICI≥2c, and 52.0% mTICI 3. The primary safety composite end point rate of sICH post-procedure or serious adverse device effects was 5.3% (95% CI, 3%-9%; FIG. 15) and all events were sICH. The rate of embolization into new territory on angiography was 6.6%. All adverse events from the second study of this disclosure are listed in FIG. 15. The median time to treat (interval from baseline angiogram to final angiogram after device 200) was observed as 24 minutes (IQR, 13-46), whereas the procedure time was 36 minutes (IQR, 24-61; FIG. 16).

Figure 19:
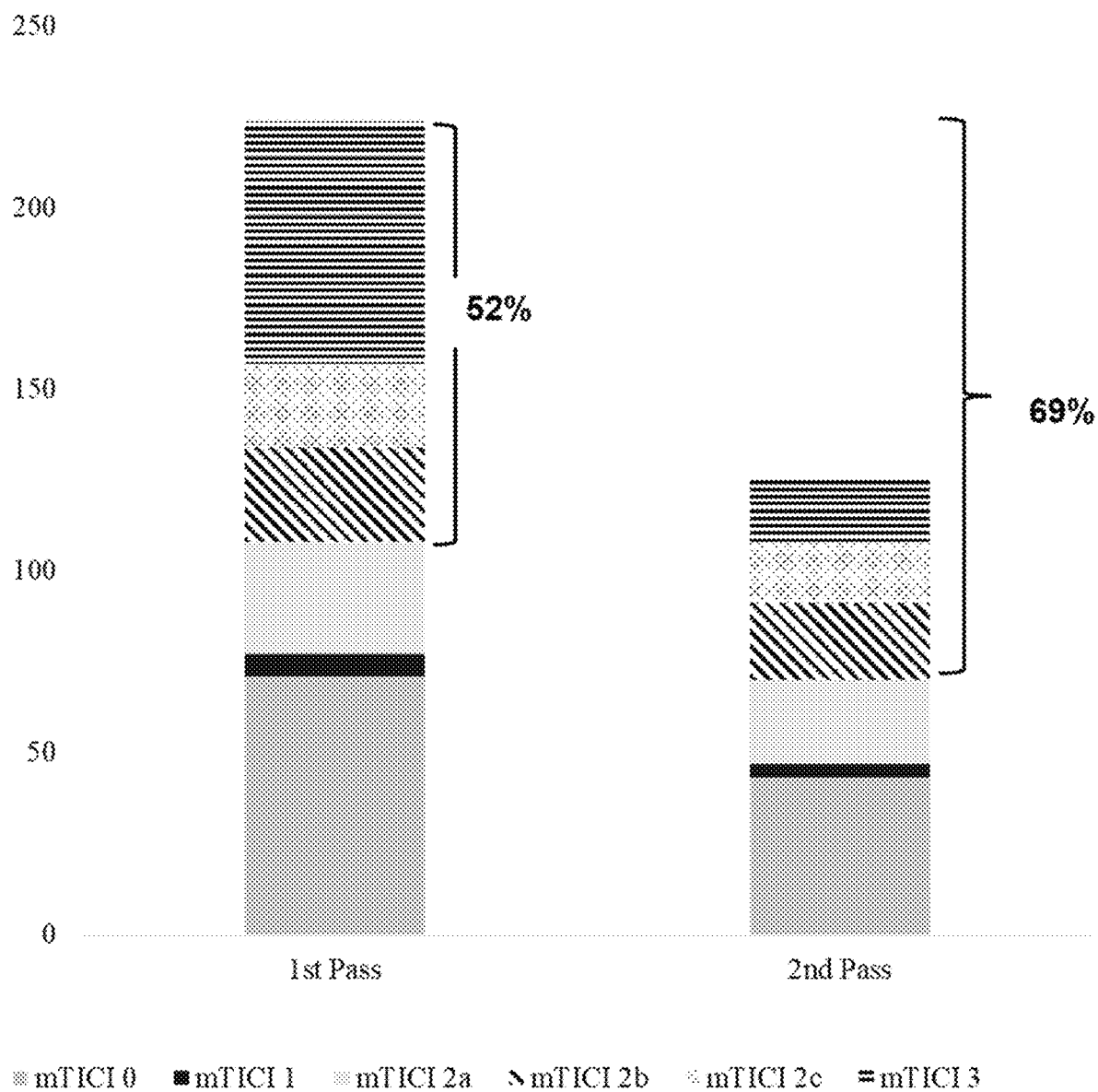
FIG. 19 depicts a graphical summary of revascularization rate per pass of the device for the study of this disclosure.

FIG. 19 depicts a graphical summary of revascularization rate (mTICI) per one pass and two passes, respectively, by device 200 with patients of the second study. It can be seen that 52% of patients achieved a mTICI≥2b after one pass of the device 200 and that 69% of patients achieved mTICI≥2b after two passes.

Figure 20:
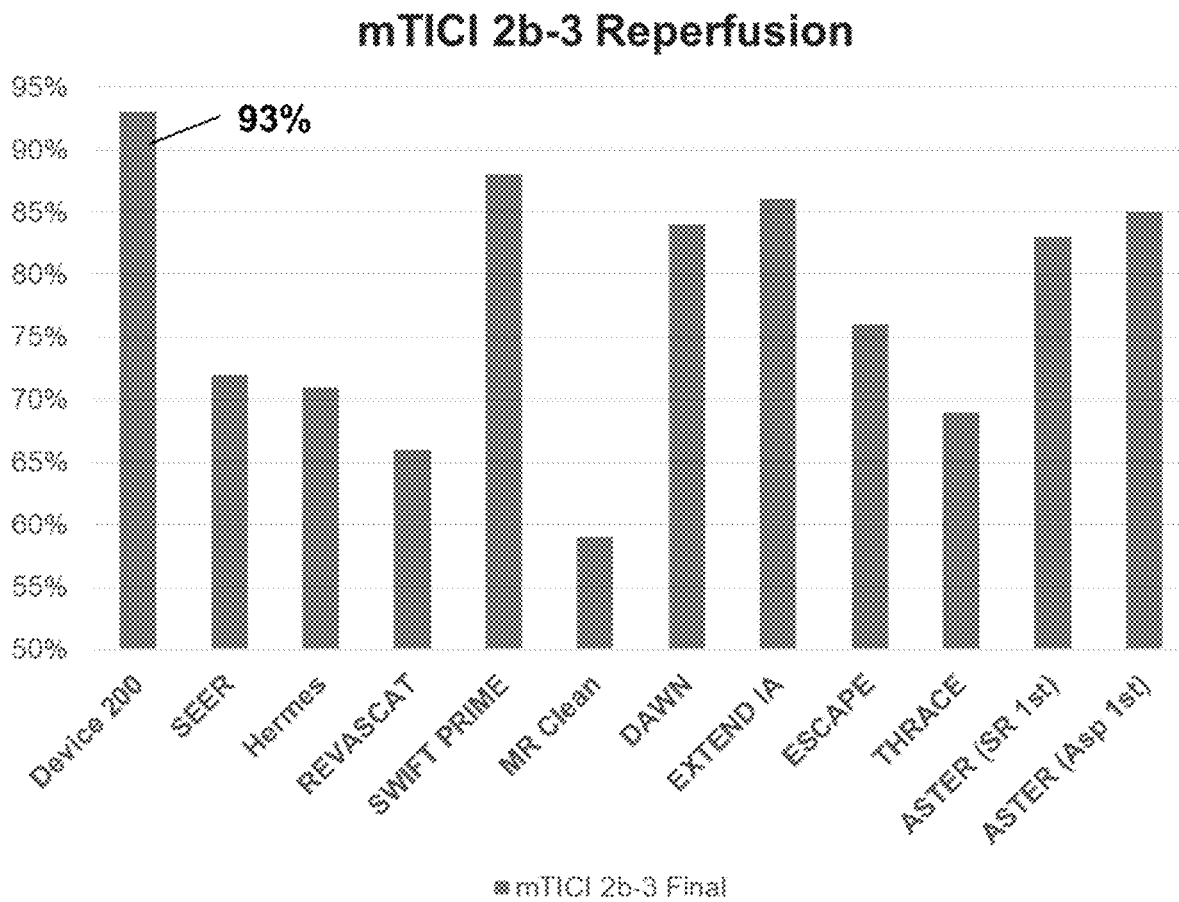
FIG. 20 is a graphical summary comparing final revascularization success rate (mTICI 2b-3) of other stent retrieval devices with the device from the study of this disclosure.

FIG. 20 is a graphical summary comparing final revascularization success rate (mTICI 2b-3) of device 200 with other devices, including SEER, Hermes, REVASCAT, SWIFT PRIME, MR CLEAN, DAWN, EXTEND IA, ESCAPE, THRACE, ASTER (SR 1$^{st}$), and ASTER (Asp. 1$^{st}$), whereby device 200 of this disclosure outperformed the prior devices with a 93% final reperfusion of mTICI 2b-3. As can be seen in FIG. 20 and in FIG. 18, the successful reperfusion rate for device 200 exceeded the threshold required to demonstrate superiority when compared with the second study set PG criterion derived from reperfusion rates achieved by the Trevo and Solitaire retriever devices in their respective regulatory registration trials.

Figure 21:
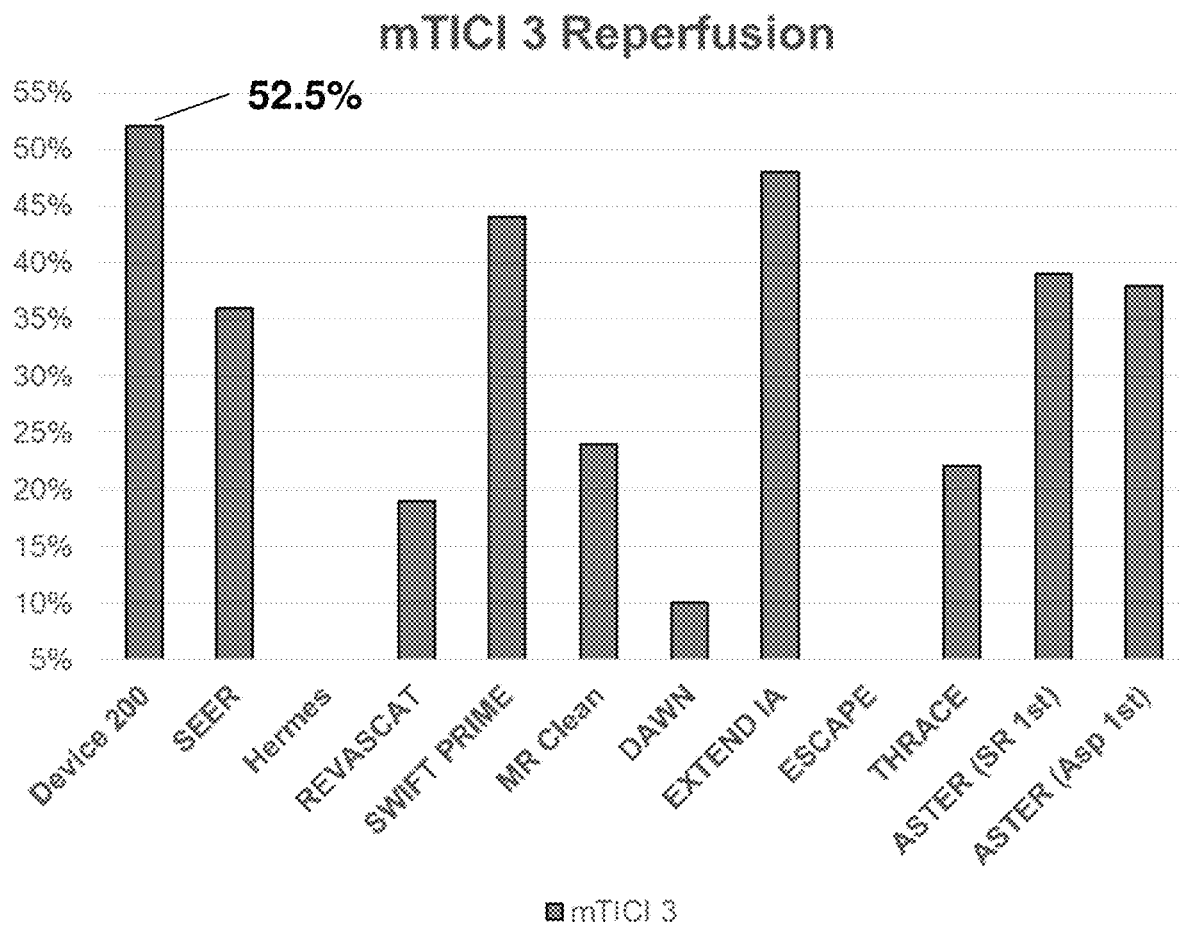
FIG. 21 is a graphical summary comparing final complete revascularization rate mTICI=3 of other retrieval devices with the device from the study of this disclosure.

FIG. 21 is a graphical summary comparing final complete revascularization rate mTICI=3 of device 200 with other devices, including SEER, Hermes, REVASCAT, SWIFT PRIME, MR CLEAN, DAWN, EXTEND IA, ESCAPE, THRACE, ASTER (SR 1$^{st}$), and ASTER (Asp. 1$^{st}$), whereby device 200 of this disclosure outperformed the prior devices with a 52.5% final complete reperfusion mTICI=3, which was a significant improvement over 48% seen in the EXTEND IA trial (i.e. approximately a 10% improvement from the closest comparable clinical data).

FIG. 22 depicts a method 300 is disclosed for treating ischemic stroke. The method 300 can include 310 delivering a clot retrieval device to a blood vessel of the patient for retrieving a clot; and 320 restoring perfusion to the blood vessel by passing the clot retrieval device by, through, or about the clot and then removing the clot retrieval device to achieve at least a 90% final revascularization rate mTICI≥2b.

FIG. 23 depicts method 400 is disclosed for treating ischemic stroke. The method 400 can include 410 delivering a clot retrieval device to a blood vessel of the patient; and 420 restoring perfusion to the blood vessel by passing the clot retrieval device by, through, or about a clot of the blood vessel and then removing the clot retrieval device with a clinically effective outcome of at least approximately 67%, a clinically effective outcome being an mRS of 0-2.

FIG. 24 depicts a method 500 for treating ischemic stroke. The method 500 can include 510 administering a clot retrieval device to a blood vessel of the patient for retrieving the clot; and 520 restoring perfusion to the blood vessel to achieve at least a 50% final revascularization rate mTICI=3 after one or more passes of the clot retrieval device by, through, or about the clot and then removing the clot retrieval device.

FIG. 25 depicts a method 600 for treating ischemic stroke. The method 600 can include 610 delivering a clot retrieval device to a blood vessel of the patient for retrieving a clot; and 620 restoring perfusion to the blood vessel after two passes of the clot retrieval device by, through, or about the clot and then removing the clot retrieval device to achieve at least a 69% revascularization rate mTICI≥2b.

FIG. 26 depicts a method 700 for treating ischemic stroke. The method 700 can include 710 delivering a clot retrieval device to a blood vessel of the patient for retrieving a clot; and 720 restoring perfusion to the blood vessel by passing the clot retrieval device by, through, or about the clot and retracting the clot retrieval device to achieve at least a 90% final revascularization rate (mTICI of 2b-3); a clinically effective outcome of at least approximately 67%, the clinically effective outcome being an mRS of 0-2; and/or at least a 50% final revascularization rate (mTICI of 3) after one or more passes of the clot retrieval device by, through, or about the clot and then removing the clot retrieval device.

Turning to FIG. 27, a table is provided that summarizes efficacy and safety of the second study of this disclosure. Patients with a large-vessel occlusion who could be treated within 8 hours of stroke symptom onset were eligible for enrolment and 191 patients met all inclusion and exclusion criteria. The Primary Efficacy Endpoint was successful revascularization defined as an mTICI score of at least 2b in the target vessel, following three or less passes the device without rescue, using Core Laboratory adjudicated data. For the FDA ITT cohort, successful revascularization was modified to count any case in whom rescue therapy was used, after the device, as a failure to meet the primary efficacy endpoint. The Primary Safety Endpoint was the occurrence of symptomatic intracerebral hemorrhage (sICH) within 24 hours of the procedure, together with any serious adverse device effects (SADE), excluding those already counted as sICH. The Primary Safety Endpoint was a statistical calculation based on data adjudicated by the Clinical Events Committee (CEC).

FIG. 28 depicts a table that summarizes primary efficacy by region. FIG. 29 depicts a table that summarizes serious adverse events (SAE) from the second study of this disclosure. Turning to FIG. 30, a table is provided that summarizes information corresponding to patients who were excluded from the second study. One of ordinary skill is aware that all data can be modified using certain parameters. In particular, data from the Second Study was submitted to a government agency requiring different parameters then set forth in the study. These government set requirements can alter certain results by changing certain presumptions, including modifying certain totals affecting the patient population and/or the results therefrom. These changes can affect the statistical analysis used to determine certain criteria noted above. FIGS. 27-30 depict some of these changes. Further, any analysis performed in light of these parameters, can be encompassed in the scope of the invention and the claims.

In another analysis, information from prior studies of other clinically evaluated reperfusion devices was analyzed. Specifically, economic outcomes was analyzed in 150 patients treated in a "current scenario" (device mix of 9% device 200 of this disclosure, 52% Solitaire, 30% Trevo) to a "future scenario" with increased adoption of device 200 (30% device 200, 40% Solitaire, 30% Trevo) over a 90-day time-horizon. Procedural costs were limited to device costs, as other costs were assumed to be similar. Acute healthcare costs based on 90-day functional outcomes using mRS were analyzed. The proportions of patients achieving each mRS level with device 200, Solitaire, and Trevo were obtained from methodologically-comparable trials (device 200 [n=227], SWIFT [n=58], and TREVO-2 [n=88], respectively); acute costs per mRS level were based on a 2018 U.S. cost-effectiveness publication. Case volume, device mix, and device costs were obtained from market research. Costs were reported as 2018 U.S. dollars.

Among 150 patients in this analysis, 61 and 70 patients achieved good functional outcomes (mRS 0-2) in the "current" and "future scenarios", respectively. Both device and acute healthcare costs were lower in the "future scenario"; total costs (all patients) were $3,650,120 in the "current" and $3,597,475 in the "future" scenarios, translating to savings of $351 per patient over 90-days. Comparison of a scenario without device 200 use to a scenario with 30% use led to 13 additional patients achieving good outcomes and savings of $530 per patient. It was therefore concluded that in addition to clinical benefits discussed herein, increased adoption of device 200 for large vessel strokes can lead to cost-savings for the U.S. payer with respect to healthcare and hospitalization.

In another analysis, the first pass effect (FPE) was investigated with respect to device 200 of this disclosure. It is understood that FPE is the ability to restore near or complete revascularization (mTICI≥2c) of acutely blocked cerebral artery in a single thrombectomy device pass. The FPE has been shown to be an independent predictor of good functional outcomes (mRS≤2), a goal of stroke therapy that impacts healthcare costs, and is associated with reduced 90-day mortality and fewer adverse events. This analysis showed that the FPE of device 200 was associated with reduced procedural healthcare resource use, including length of stay, days in the intensive care unit, standard bed days, and devices used. FPE of device 200 was also associated with accompanying short-term costs. Among those who achieved complete revascularization in the second study of this disclosure, the proportion of patients achieving each mRS score was assessed, stratified by the FPE status. Long-term costs per mRS score, obtained from a 2015 U.S. cost-effectiveness analysis that projected annual post-hospitalization inpatient/outpatient and nursing home costs using data from the National Death Index and Centers for Medicare and Medicaid Services (CMS), were applied to all patients. Post-hospitalization costs, in 2018 USD, were then compared between patients that did or did not achieve the FPE and incremental differences were calculated for a 1-year time horizon.

The analysis revealed that 76% of patients (n=172) achieved complete revascularization; among these patients, 53% achieved the FPE. A significantly higher percentage of patients that achieved the FPE had good functional outcomes vs. those that did not achieve the FPE (80.46% vs. 61.04%, p=0.006). Estimated annual post-hospitalization costs were lower among patients that achieved the FPE vs. those that did not achieve the FPE, leading to estimated per-patient cost-savings of $3,876. In the absence of cost data reported in the second study, costs for healthcare resource use were obtained from the literature. Additionally, the cost-effectiveness analysis used to inform the long-term costs per mRS score did not report costs for death (i.e., mRS 6), which had a lower incidence among patients that achieved the FPE vs. those that did not achieve the FPE (5.75% vs. 14.29%); as such, further cost-savings may be realized if costs related to death are considered. In addition to clinical benefits and short-term cost-savings, achieving the FPE of device 200 can lead to long-term per-patient cost-savings of $3,876 due to improved functional outcomes. FIG. 31A is a table summarizing per-patient long-term costs of this analysis based on functional outcomes of the second study of this disclosure.

Healthcare resource use was also lower among patients that achieved the FPE. While patients that achieved the FPE required only a single device 200, 35% of the patients that did not achieve the FPE required both the device 200 and an additional device to achieve complete revascularization. Patients that achieved the FPE had a significantly shorter LOS (6.10 vs. 9.48 days, p=0.004) and fewer days spent in a standard bed (3.05 vs. 6.13, p=0.004) vs. those that did not achieve the FPE. Overall, the reduction in healthcare resource use associated with achieving the FPE led to estimated per-patient cost-savings of $6,355 (See, e.g., FIG. 31B which summarizes per-patient procedural healthcare resource). This analysis did not include all components of health resource use that may impact costs (e.g., procedure time, surgical evacuation for sICH).

In another analysis of the study of this disclosure, FPE and mTICI were used as predictors of patient functional outcome with Anterior circulation LVO [ACLVO-internal carotid (ICA)] ("ACLVO ICA") and MCA-M1 strokes from the study of this disclosure. In the analysis, FPE and modified FPE (mFPE) were defined as first pass achievement of TICI 2C/3 and TICI≥2B, respectively. Demographic, clinical and radiographic parameters were analyzed. Multivariable logistic regression was performed to identify predictors. A total of 161 ACLVOs underwent thrombectomy in the ARISE II study. Mean age was 67±13 years and 43% (n=69) were male. Mean NIHSS and median ASPECTS were 16±5 and 10, respectively. While FPE was achieved in 37% (n=59), mFPE was seen 43% (n=69) patients. Multivariable logistic regression was performed using age, sex, use of IV-tpA, BMI, NIHSS, vascular risk factors, ASPECTS, collateral status (ASITN), occlusion location and use of balloon-guided catheter as variables. While absence of ICA occlusion (p=0.07, OR-8.6, 0.8-90) can predict FPE, there were no independent predictors of mFPE. Independent predictors of TICI 3 after 3 passes include use of balloon guide catheter (p=0.01, OR-0.033, 0.003-0.535) and higher ASITN score (p=0.04, OR-10.2, 1-100). The analysis revealed that absence of ICA occlusion predicts FPE and the use of balloon guide catheter ("BGC") and favorable collaterals predicts complete revascularization. The solution of this disclosure therefore incorporates routine BGC use with device 200 to achieve complete revascularization.

In another analysis of the study of this disclosure, a univariate and multivariate logistic regression was performed to determine the independent predictors of unfavorable outcomes at 90 days (defined as mRS 3-6). The variables tested as predictors in the analysis included Age, Gender, Collateral grade, ASPECTS, mode of transfer, NIHSS score, use of intravenous tissue plasminogen activator, number of passes, clot location, final mTICI and sICH. Odds ratio (OR) with 95% CI were reported. In the analysis, unfavorable outcomes (mRS=3-6) at 3 months were seen in 29.6% patients. M1 was the most common site of occlusion with 54.55% followed by M2 (25.0%) and ICA (15.91%). Delay from stroke onset to the deployment of stent retriever was 3.97±1.44 hours. On univariate logistic regression analysis age, ASPECTS, collateral grade, time from stroke onset to the deployment of stent retriever, duration of procedure, NIHSS score, and sICH were found to be significant predictors of unfavorable outcomes. On multivariate analysis collateral grade (OR, 0.24, 95% CI 0.06-0.94, p value 0.04), NIHSS score (OR 1.28, 95% CI 1.15-1.43, p value <0.001), and number of passes (OR, 2.08, 95% CI 1.40-3.10, p value 0.0003) were found to be independent predictors of unfavorable outcomes in patients with successful recanalization. Accordingly, collateral grade, NIHSS score at presentation, and number of passes are therefore independent predictors of unfavorable outcomes at 90-days in the use and method of device 200 according to this disclosure, In another analysis of the study of this disclosure, outcomes were investigated of patients admitted during night time or weekends versus those of patients admitted during regular working hours. Of the study of this disclosure, of the available data it was seen that approximately about 45% of patients were admitted during regular working hours to the treating hospital (e.g., 8 am-5 pm) and while approximately about 55% were admitted during non-office hours, weekends (Saturday and Sunday) or holidays. Time from admission to groin puncture for access of device 200 was shorter during office hours (1 hr vs 1.2 hrs, p=0.007). Revascularization was the approximately about the same in both groups, i.e. mTICI 2c-3 after first pass was 38% vs 42% (p=0.58), mTICI 3 after first pass 28% vs 32% (p=0.55), mTICI 2c-3 after 3 passes 64% vs 60% (p=0.58), mTICI 3 after 3 passes 45% vs 44% (p=0.80), final mTICI 2c-3 72% vs 79% (p=0.27) and final TICI 3 was 52% vs 51% (p=0.97). Clinical outcome assessed as mRS 0-1 was 50% vs 53% (p=0.72) and mRS 0-2 was 65% vs 70% (p=0.42). Accordingly, the analysis revealed that time from admission to delivery of device 200 to the patient (e.g., groin puncture) was shorter in patients treated during office hours compared to treatment during non-office hours. However, time of treatment being administered had no effect on quality of reperfusion or clinical outcomes, other than the impact on time to delivery to the patient.

Figure 32:
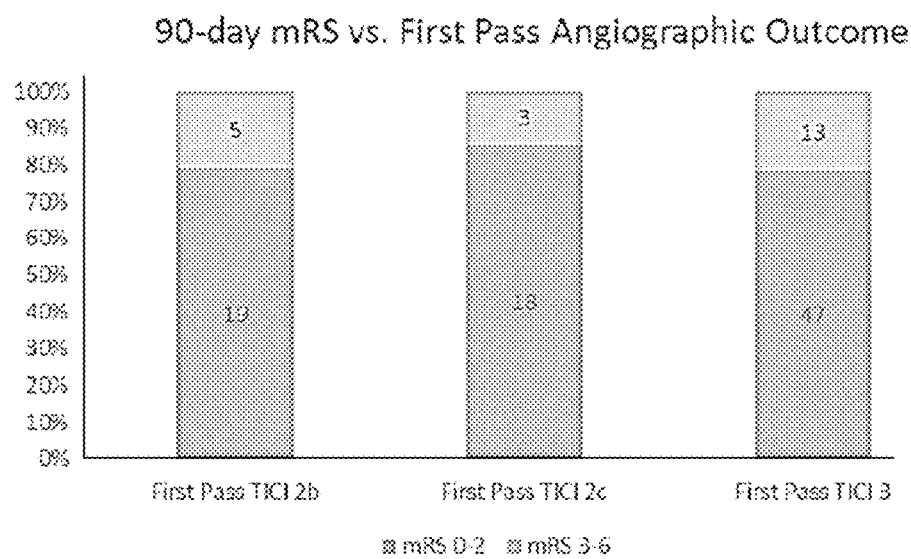
FIG. 32 depicts a graphical summary of revascularization rate per first pass of the device for the study of this disclosure.

Turning to FIG. 32, a graphical summary is shown of revascularization rate per first pass of the device 200 for the study of this disclosure at 90-days following the procedure associated with device 200. In particular, FIG. 32 shows that mRS 0-2 was seen in 78% to 86% in all groups mTICI 2b, TICI 2c, or TICI 3 after one pass of the device 200.

Figure 33:
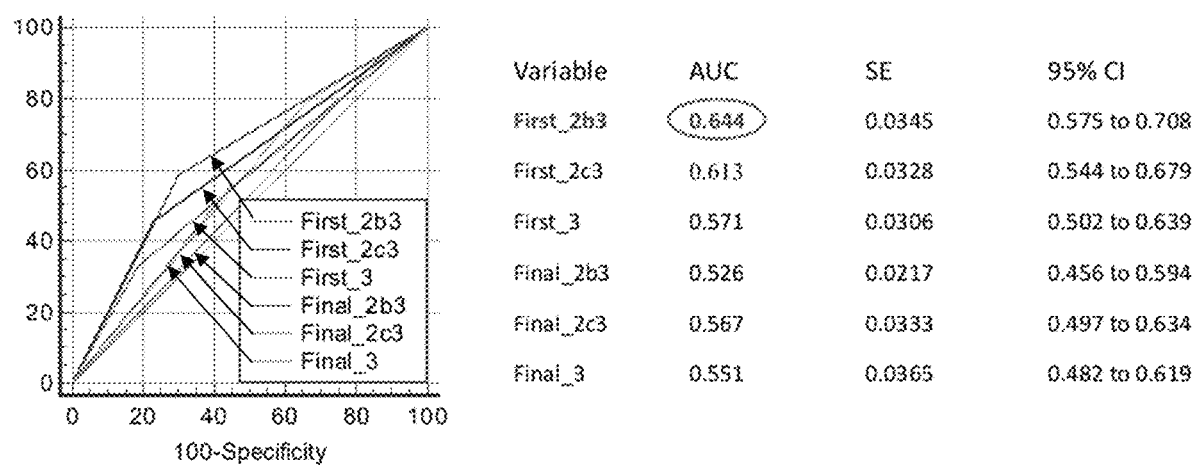
FIG. 33 depicts a graphical summary of Receiver-Operating Characteristic (ROC) analysis for prediction of 90-day mRS 0-2 of the study of this disclosure.

FIG. 33 depicts a graphical summary of ROC analysis for prediction of 90-day mRS 0-2 of the study of this disclosure. ROC analyses were used to compare first pass and final mTICI scores greater than or equal to 2b for optimal prediction of 90-day mRS 0-2, 24-hour NIHSS improvement of greater than or equal to 8 points, and 90-day mortality. Stated differently, ROC analysis drew from FPE information and then used this to determine the best cut-off for dichotomizing a predictor such that the combination of sensitivity and specificity is maximized when that variable is used to predict outcome. Area under the curve (AUC) 0.5 means no diagnostic ability and AUC=1.0 means perfect diagnostic ability for the dichotomized variable. Further, in ROC analyses, first pass TICI 2b-3 was the best angiographic endpoint for predicting 90-day mRS 0-2 (AUC=0.644), greater than or equal to 8-point improvement in 24-hour NIHSS (AUC=0.625) and 90-day mortality (AUC=0.634).

Figure 34:
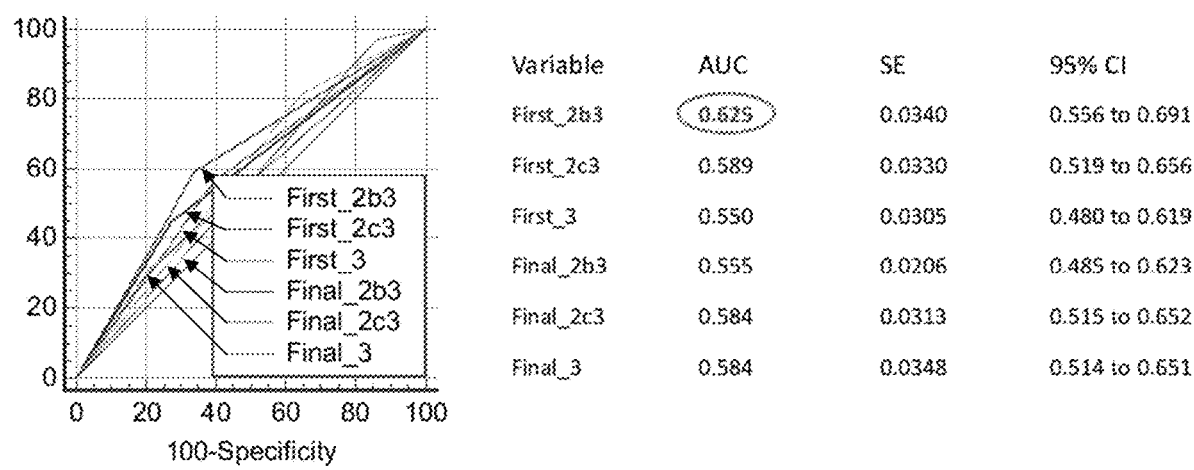
FIG. 34 depicts a graphical summary of ROC analysis for prediction of 24-hour 8+ NIHSS improvement of the study of this disclosure.

FIG. 34 depicts a graphical summary of ROC analysis for prediction of 24-hour 8+ NIHSS improvement of the study of this disclosure.

Figure 35:
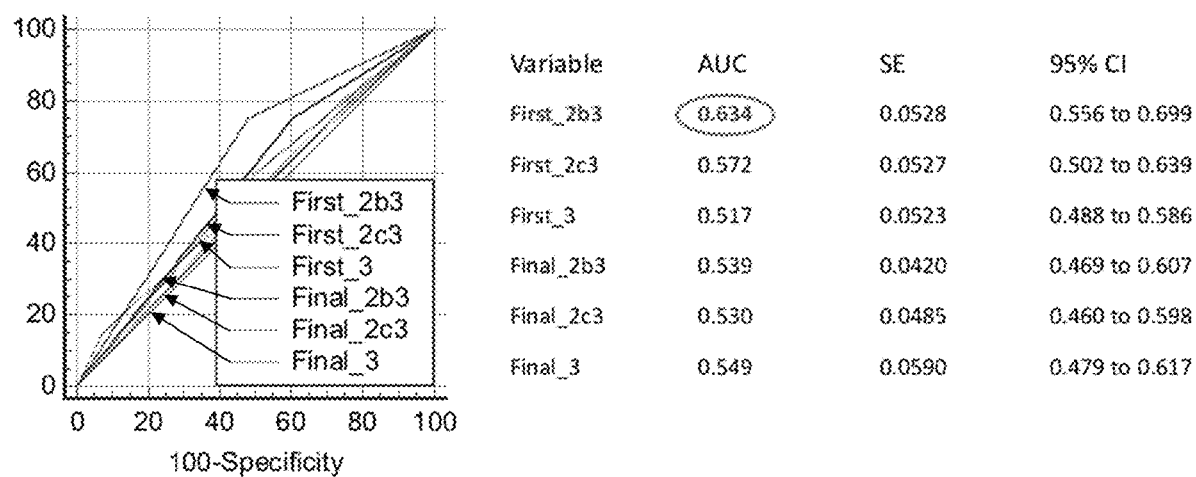
FIG. 35 depicts a graphical summary of ROC analysis for prediction of 90-day mortality of the study of this disclosure.

FIG. 35 depicts a graphical summary of ROC analysis for prediction of 90-day mortality of the study of this disclosure. Clearly, among subjects with final mTICI being greater than or equal to 2b, the subgroup with first pass of device 200 being greater than or equal to greater than 2b had lower median 90-day mRS, lower mortality (4.8% v. 13.2%), and lower rate of symptomatic intracranial hemorrhage (1.8% v. 7.6%). Stated differently, substantial reperfusion with the first pass of device 200 during the procedure described herein demonstrates clear causal and correlative indications significantly improving safety and functional outcomes as compared to outcomes after all interventions such that the first pass TICI 2b-3 is the preferred angiographic endpoint for predicting clinical and safety outcomes.

FIG. 36A depicts a table summarizing per pass improved mTICI information from the study of this disclosure. FIG. 36B depicts a table summarizing per pass mTICI and 90-day mRS information from the study of this disclosure. In particular, good mRS outcome was not significantly associated with the number of passes in patients with final mTICI of 2c-3 (Chi-square p=0.0714). There was generally an incremental reperfusion benefit of going to the next pass. Successful recanalization with the final pass, defined as mTICI 2c-3, was predictive of a successful mRS (0-2) outcome (chi-square p=0.0031). For more than 3 passes in FIG. 36A, the number of patients per pass was too low to make any conclusions. Patients with successful reperfusion at pass 6 and 8 had good mRS outcomes. The clinical benefit (90 day mRS of 0-2) with good reperfusion was maintained between the first and second pass (FIG. 36B), and decreased with the third pass of device 200. The rate of good clinical outcome, defined as mRS≤2 at 90 days, decreased with the total number of passes (81.3%, 71.1%, 52.1%, and in patients with 1, 2, 3, and 4+ passes).

It can be seen in FIGS. 36A-B that successful reperfusion within the first two passes gives the best chance of good clinical outcome (80%), successful stepwise reperfusion with mechanical thrombectomy is associated with good clinical outcomes, and that good clinical outcomes are possible even with a high number of device passes. Further, in single-predictor logistic regression models, the number of passes (p=0.0001) was more highly associated with mRS than the final TICI score (p=0.0013).

In another study, five hundred thirty-three (533) clot specimens from three hundred and seventy-six (376) subjects were collected by twenty (20) sites and sent for analysis, whereby each specimen was retrieved from a subject with device 200. Clot composition data, for two-hundred and thirty-four (234) clots from one-hundred and sixty-three (163) subjects, was evaluated in the study.

In particular, vessel susceptibility sign can indicate acute occlusion in more RBC rich clots that may result in more favorable clinical outcomes in patients treated with device 200. The presence ("SVS+") or absence ("SVS−") of vessel susceptibility sign can be recorded via MR imaging before mechanical thrombectomy. In the results of the analysis, it was discovered that cardioembolic etiology (n=100) was associated with lower red blood cell (RBC) (40.2% in susceptible vessel sign—("SVS−") vs 47.2% in susceptible vessel sign+ ("SVS+")) and higher fibrin content (31.7% SVS− vs 26.7% SVS+) compared to large artery disease (n=12). Hyperdense/vessel susceptibility sign (78+, 24−, per independent imaging core lab) corresponded to higher mean RBC content (44.4% SVS+vs 34.9% SVS−). Treatment with IV tPA (60 SVS+, 91 SVS−) had no clear impact on clot composition (42.3% SVS+vs SVS− RBC; 30.4% SVS+vs 30.0% SVS− fibrin). Notably, clots retrieved with the first 2 passes by device 200 were more RBC rich (42.1% SVS+vs 28.0% SVS−) and clots retrieved in higher passes had a higher average fibrin content (35.5% SVS+vs 29.6% SVS−) suggesting that higher fibrin content leads to greater refractoriness, or clot fracturing.

The device 200 and related methods of use of this disclosure demonstrated high rates of substantial reperfusion and functional independence in patients with acute ischemic stroke secondary to large-vessel occlusions. The specific configurations, choice of materials and the size and shape of various elements can be varied according to particular design specifications or constraints requiring a system or method constructed according to the principles of the disclosed technology. Such changes are intended to be embraced within the scope of the disclosed technology. The presently disclosed embodiments, therefore, are considered in all respects to be illustrative and not restrictive. It will therefore be apparent from the foregoing that while particular forms of the disclosure have been illustrated and described, various modifications can be made without departing from the spirit and scope of the disclosure and all changes that come within the meaning and range of equivalents thereof are intended to be embraced therein.

What is claimed is:

1. A method of restoring blood flow in neurovasculature by removing thrombus in human patients experiencing ischemic stroke, the method comprising:
    delivering a dual-layer clot retrieval device to a blood vessel of a respective human patient of a plurality of human patients for retrieving a clot;
    passing the dual layer clot retrieval device by, through, or about the clot in two passes or less; and
    removing the dual layer clot retrieval device after two passes or less, to improve a final revascularization rate under a modified treatment in cerebral infarction score (mTICI) for approximately 42% of the human patients in the plurality of human patients.

2. The method of claim 1, further comprising achieving a good clinical outcome of mRS from approximately 71.1% to approximately 81.3% under a modified Rankin Scale (mRS) score of 0-2 within a predetermined time period comprising 90-days following restoring perfusion to the blood vessel.

3. The method of claim 1, further comprising achieving a reduced clot fracturing after two passes of the dual layer clot retrieval device by, through, or about the clot.

4. The method of claim 1, further comprising achieving approximately an 80% final revascularization rate mTICI greater than 2b after two passes of the dual layer clot retrieval device by, through, or about the clot.

5. The method of claim 4, wherein further comprising restoring perfusion to the blood vessel after a single pass of the dual layer clot retrieval device by, through, or about the clot and removing the dual layer clot retrieval device to achieve a final revascularization rate mTICI≥2c-3 in approximately 80% of human patients in the plurality of human patients.

6. The method of claim 1, wherein the clot is located in one of the following locations: a carotid artery, a MI middle cerebral artery, a M2 middle cerebral artery, a basilar artery, and a vertebral artery.

7. The method of claim 1, wherein the dual-layer clot retrieval device comprises:
    a first framework of struts forming a tubular main body portion; and
    a second framework of struts forming an outer tubular body at least partially surrounding the tubular main body portion, wherein the outer tubular body is expandable to a radial extent to define a clot reception space.

8. The method of claim 7, wherein
    the tubular main body portion further comprises a porous inner body, and
    the outer tubular body comprises a plurality of longitudinally spaced clot scaffolding segments comprising closed cells whereby each of the plurality of longitudinally spaced clot scaffolding segment is separated by a clot inlet mouth and at least one closed cell of each of the plurality of longitudinally spaced clot scaffolding segment terminates in a distal apex free from connection to an adjacent closed cell.

* * * * *